United States Patent
Beach

(10) Patent No.: US 10,912,922 B2
(45) Date of Patent: Feb. 9, 2021

(54) MODULAR MEDICAL DEVICE CATHETER SYSTEM

(71) Applicant: COVELLUS LLC, Belmar, NJ (US)

(72) Inventor: Bradley Beach, Belmar, NJ (US)

(73) Assignee: COVELLUS LLC, Belmar, NJ (US)

( * ) Notice: Subject to any disclaimer, the term of this patent is extended or adjusted under 35 U.S.C. 154(b) by 0 days.

(21) Appl. No.: 16/181,805

(22) Filed: Nov. 6, 2018

(65) Prior Publication Data

US 2019/0151613 A1   May 23, 2019

Related U.S. Application Data

(63) Continuation-in-part of application No. 15/730,946, filed on Oct. 12, 2017, which is a continuation-in-part of application No. 15/196,952, filed on Jun. 29, 2016, now Pat. No. 10,328,250.

(60) Provisional application No. 62/581,998, filed on Nov. 6, 2017, provisional application No. 62/453,669, filed on Feb. 2, 2017, provisional application No. 62/407,557, filed on Oct. 13, 2016, provisional application No. 62/325,700, filed on Apr. 21, 2016, provisional application No. 62/279,858, filed on Jan. 18, 2016, provisional application No. 62/249,482, filed on Nov. 2, 2015, provisional application No. 62/188,363, filed on Jul. 2, 2015.

(51) Int. Cl.
*A61M 25/00* (2006.01)
*A61M 25/10* (2013.01)

(52) U.S. Cl.
CPC .... *A61M 25/0052* (2013.01); *A61M 25/0069* (2013.01); *A61M 25/1011* (2013.01); *A61M 25/0097* (2013.01)

(58) Field of Classification Search
CPC ............ A61M 39/105; A61M 39/1011; A61M 2039/1077; A61M 25/0138; A61M 25/0012; A61M 25/0052; A61M 25/0069; A61M 25/0097
See application file for complete search history.

(56) References Cited

U.S. PATENT DOCUMENTS

| 4,068,660 | A | * | 1/1978 | Beck | ............... A61M 25/0111 604/158 |
|---|---|---|---|---|---|
| 4,634,432 | A | | 1/1987 | Kocak | |
| 4,932,419 | A | | 6/1990 | Toledo | |
| 4,955,862 | A | | 9/1990 | Sepetka | |

(Continued)

FOREIGN PATENT DOCUMENTS

| JP | H08243169 A | 9/1996 |
|---|---|---|
| JP | H10503673 A | 4/1998 |

(Continued)

OTHER PUBLICATIONS

International Search Report and Written Opinion of PCT/US2020/0117149 dated May 7, 2020.

(Continued)

*Primary Examiner* — Manuel A Mendez
*Assistant Examiner* — Justin L Zamory
(74) *Attorney, Agent, or Firm* — Campbell IP Law LLC

(57) ABSTRACT

A modular medical device catheter system comprises a parent module and an adapter module. The adapter module is configured to engage an inner lumen of a distal end of the parent module to couple the adapter module with the parent module.

19 Claims, 31 Drawing Sheets

(56) References Cited

U.S. PATENT DOCUMENTS

| | | |
|---|---|---|
| 5,571,073 A | 11/1996 | Castillo |
| 5,788,653 A | 8/1998 | Lorenzo |
| 5,830,189 A | 11/1998 | Chang |
| 6,117,106 A | 9/2000 | Wasicek et al. |
| 6,547,766 B1 | 4/2003 | Fitz |
| 7,976,557 B2 | 7/2011 | Kunis |
| 8,100,884 B2 | 1/2012 | Schweikert et al. |
| 8,523,840 B2 | 9/2013 | Powers et al. |
| 8,690,859 B2 | 4/2014 | Drake et al. |
| 8,905,998 B2 | 12/2014 | Stephens |
| 9,174,008 B1 | 11/2015 | Kramer |
| 9,204,928 B2 | 12/2015 | Erdman et al. |
| 9,282,991 B2 | 3/2016 | Schur et al. |
| 9,550,046 B1 | 1/2017 | Allen et al. |
| 9,808,276 B2 | 11/2017 | Silvestro |
| 2002/0095102 A1 | 7/2002 | Winters |
| 2003/0195428 A1 | 10/2003 | Brockway et al. |
| 2004/0082879 A1* | 4/2004 | Klint ............... A61B 17/12022 600/585 |
| 2004/0260271 A1 | 12/2004 | Huyser et al. |
| 2005/0027282 A1 | 2/2005 | Schweikert et al. |
| 2005/0261664 A1 | 11/2005 | Rome et al. |
| 2006/0259005 A1 | 11/2006 | Konstantino et al. |
| 2007/0049960 A1 | 3/2007 | Stephens et al. |
| 2007/0244440 A1 | 10/2007 | Pal et al. |
| 2007/0265597 A1 | 11/2007 | Schweikert et al. |
| 2008/0275427 A1 | 11/2008 | Sage |
| 2009/0163915 A1 | 6/2009 | Potter |
| 2011/0275894 A1 | 11/2011 | Mackin |
| 2013/0184654 A1 | 7/2013 | Drake et al. |
| 2014/0046194 A1 | 2/2014 | Erdman et al. |
| 2014/0094688 A1 | 4/2014 | Tegg et al. |
| 2014/0191501 A1 | 7/2014 | Brugger et al. |
| 2014/0296888 A1 | 10/2014 | Schur et al. |
| 2014/0324079 A1 | 10/2014 | Silvestro |
| 2015/0105771 A1 | 4/2015 | Sim et al. |
| 2015/0283372 A1 | 10/2015 | Maritan et al. |
| 2017/0119428 A1 | 5/2017 | Boyle et al. |

FOREIGN PATENT DOCUMENTS

| | | |
|---|---|---|
| WO | 2009045793 A1 | 4/2009 |
| WO | 2015007650 A1 | 1/2015 |

OTHER PUBLICATIONS

Machine Translated Office Action of Japanese Application No. 2017-568259 dated May 15, 2020.

* cited by examiner

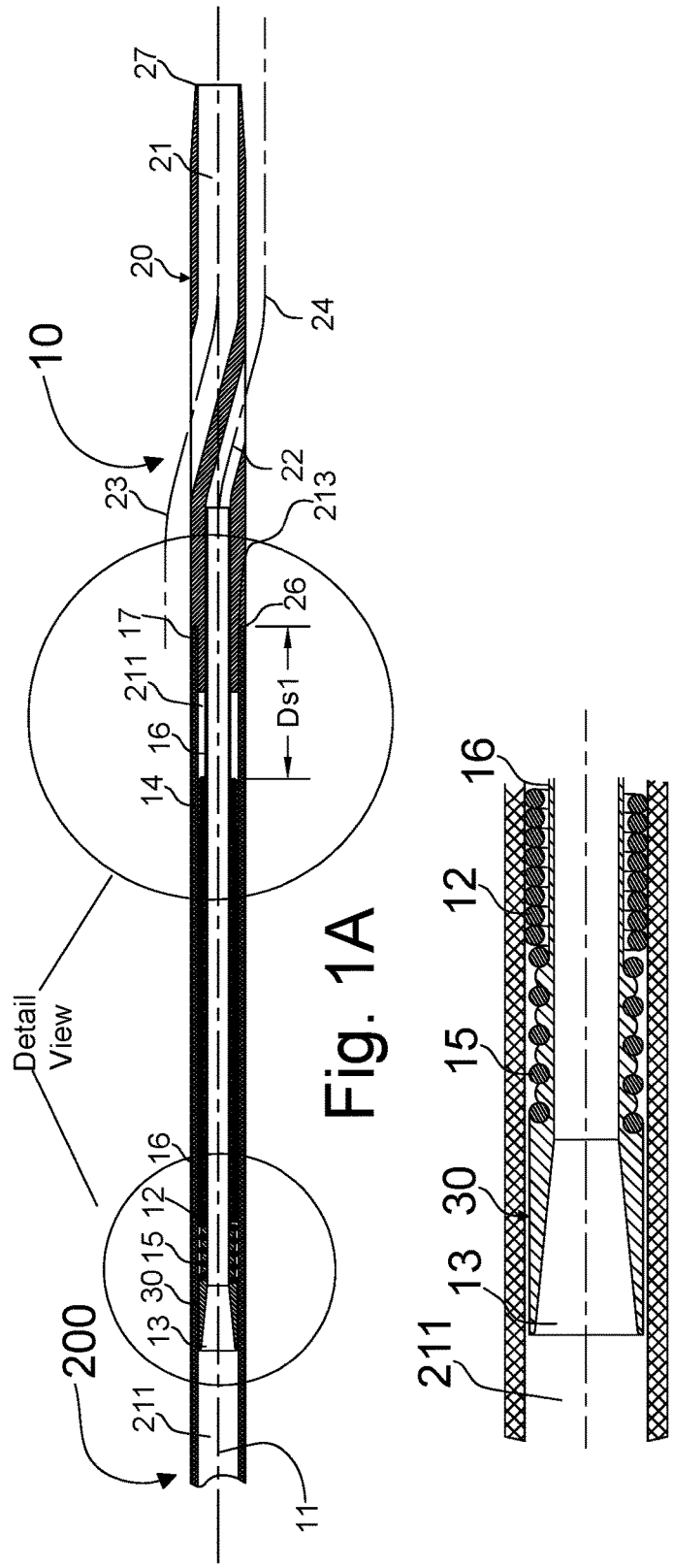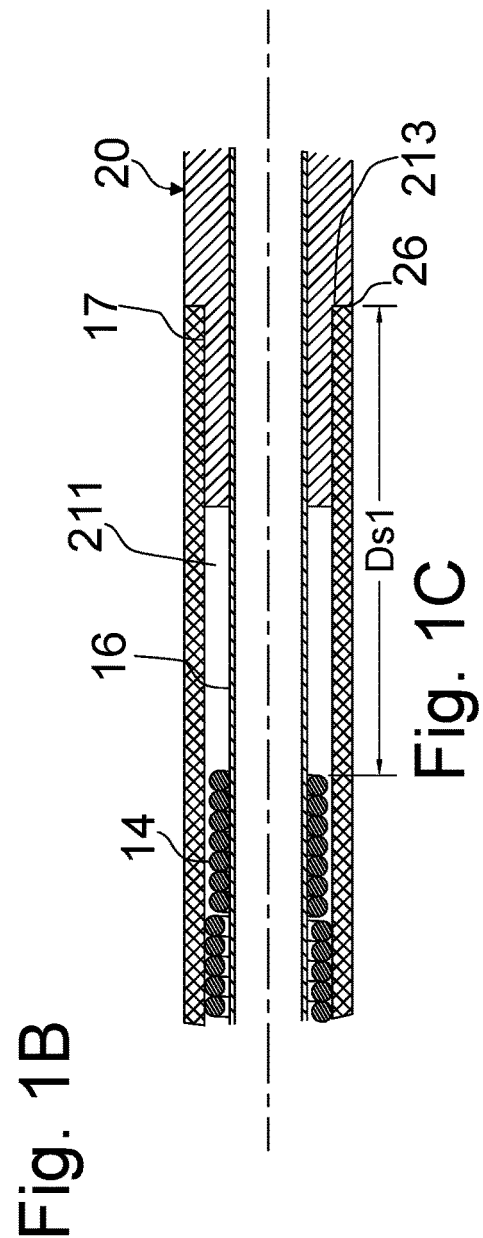

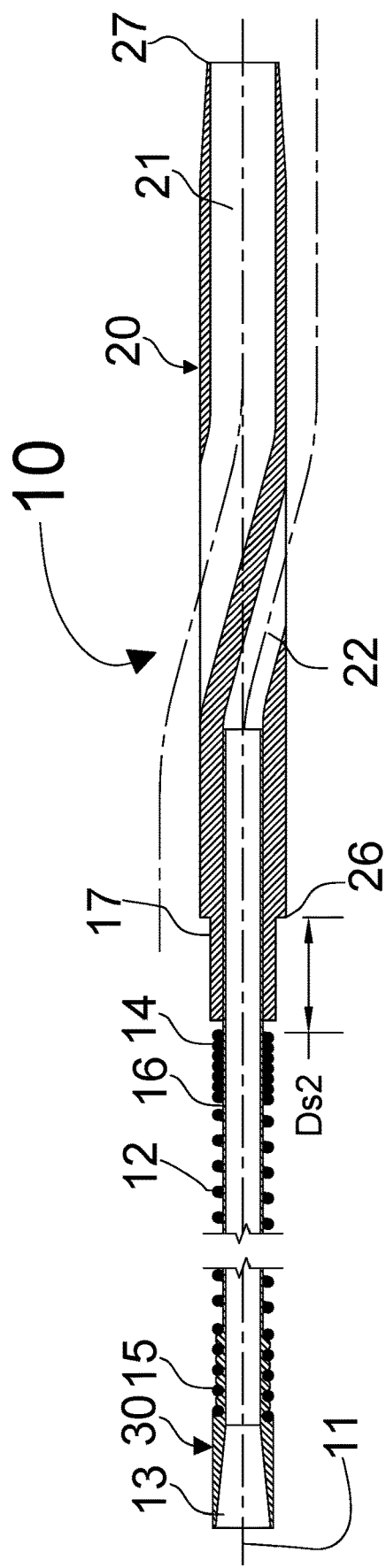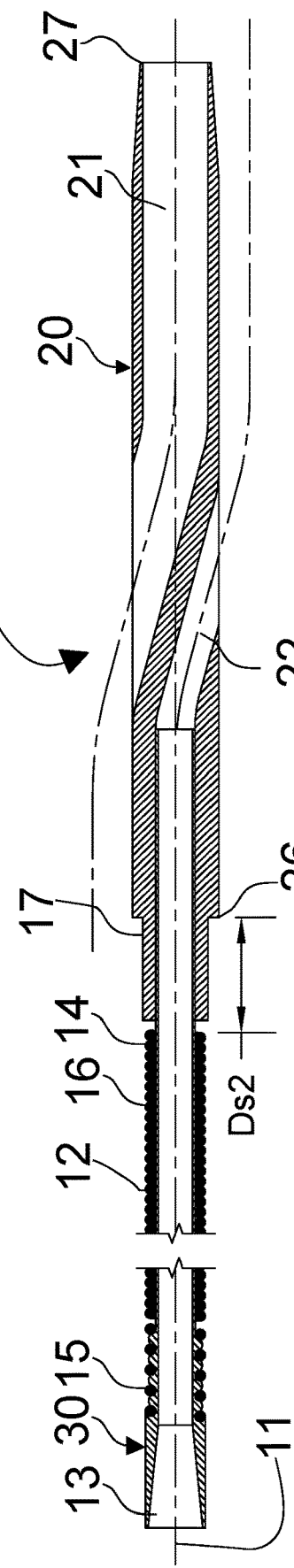

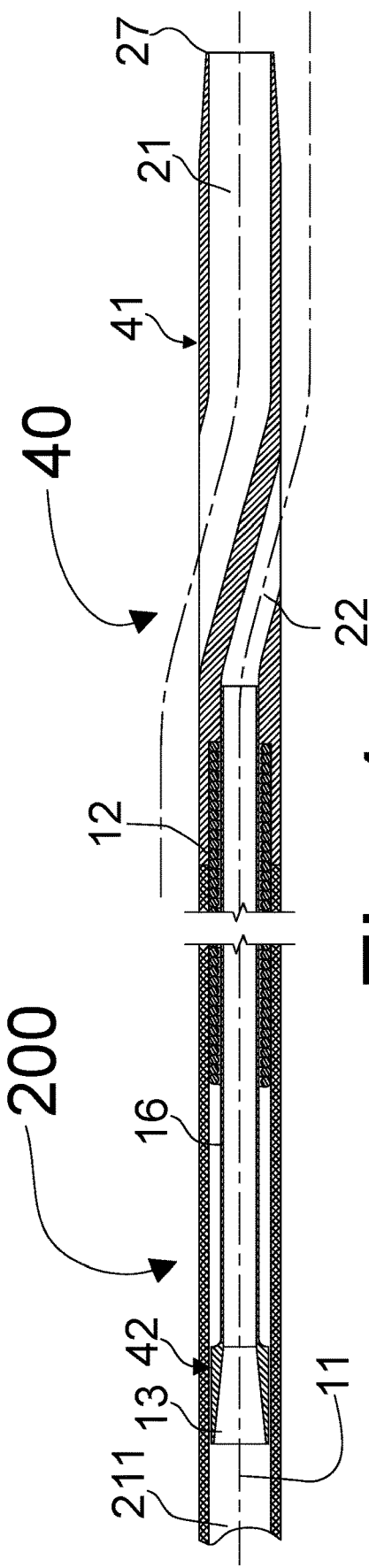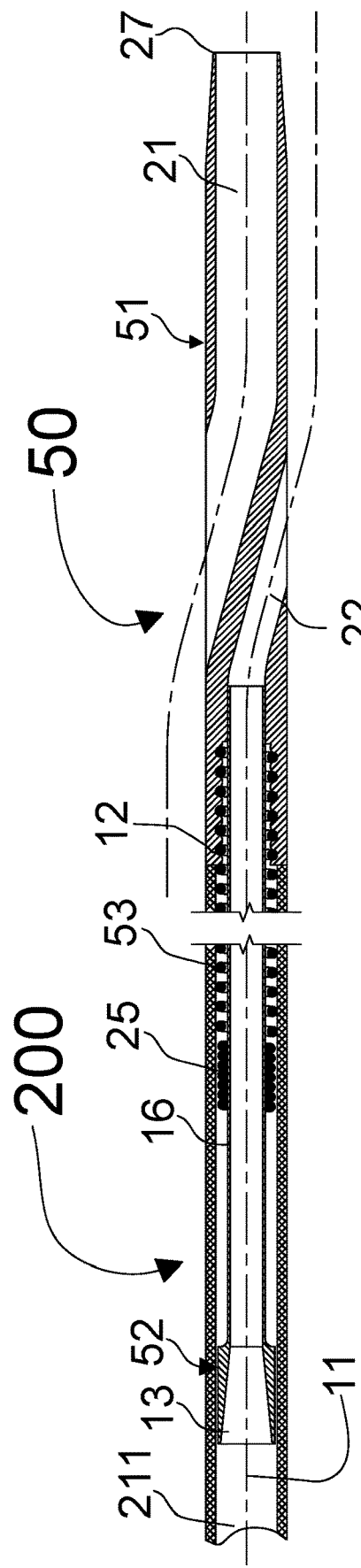

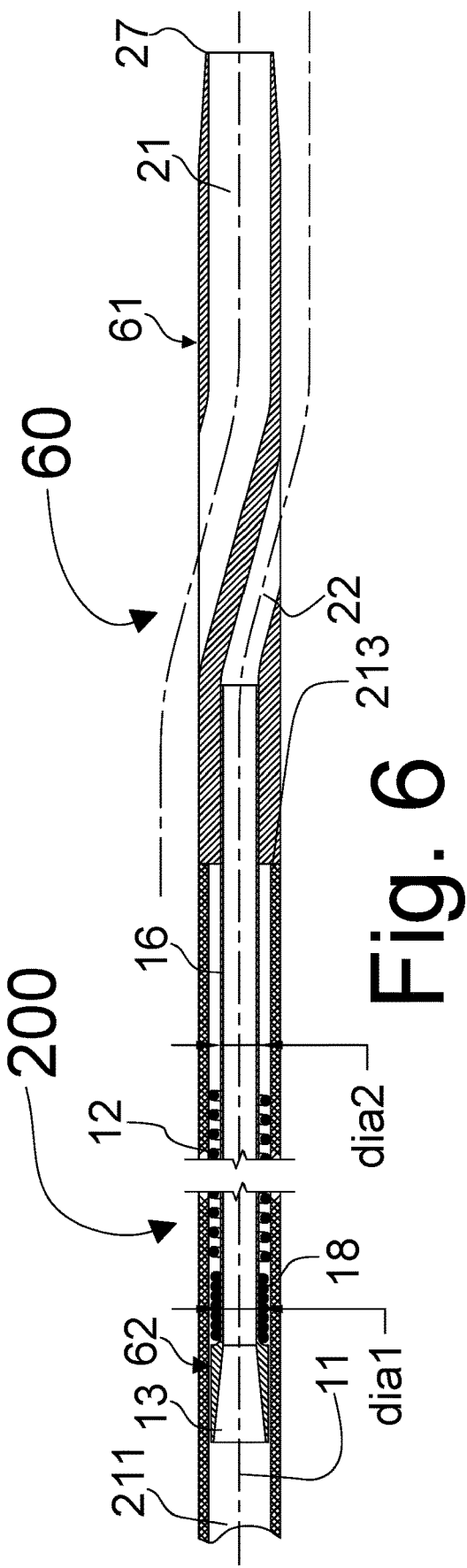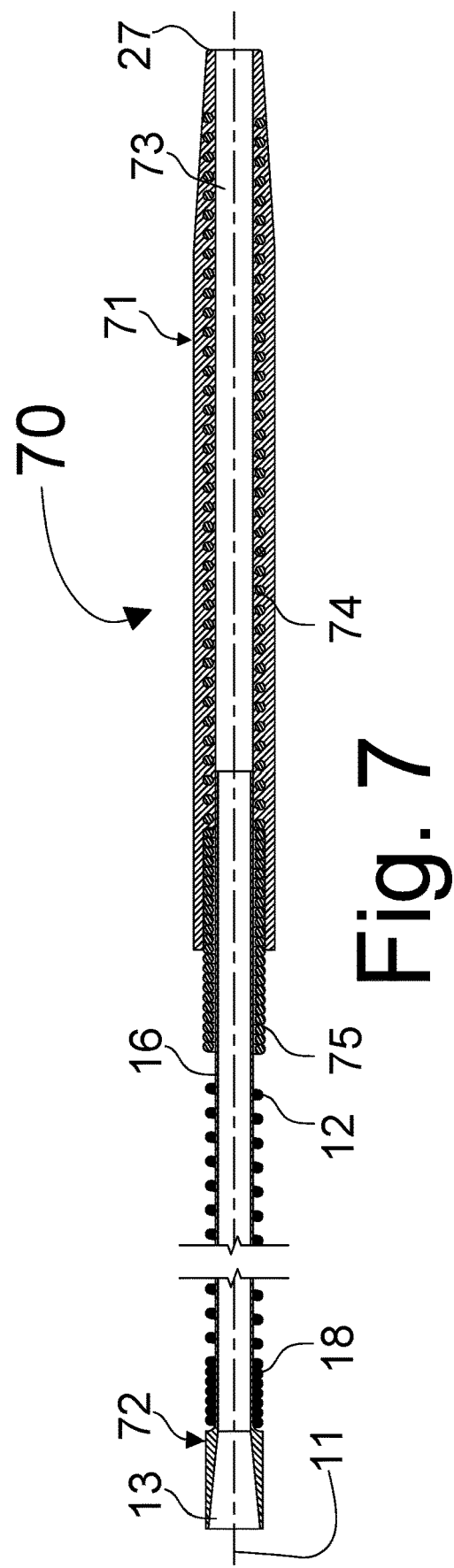

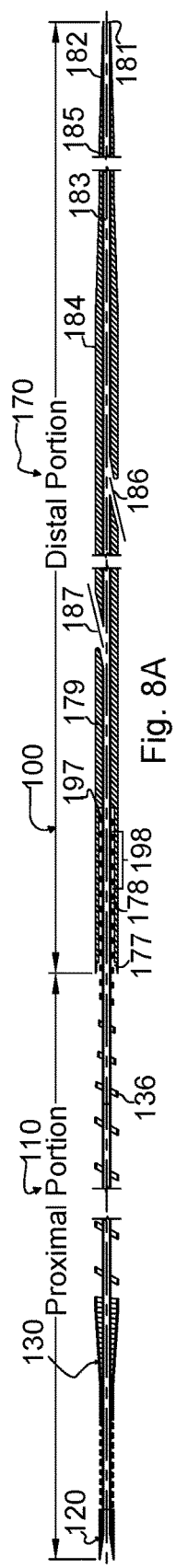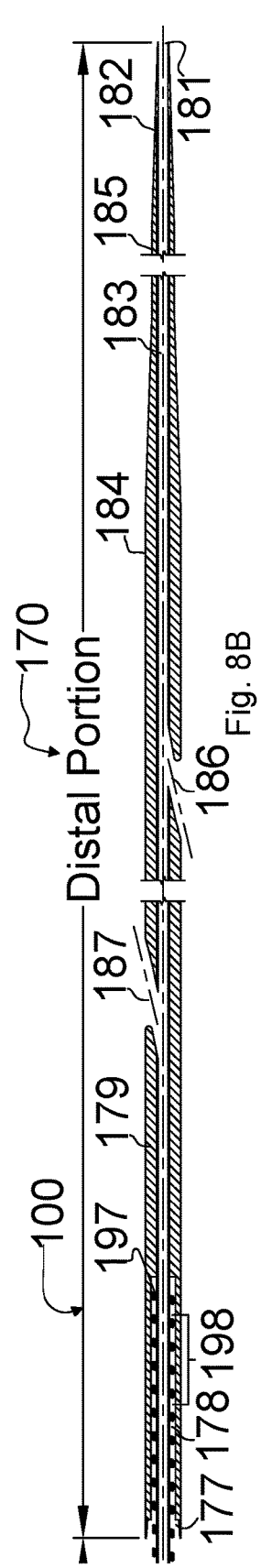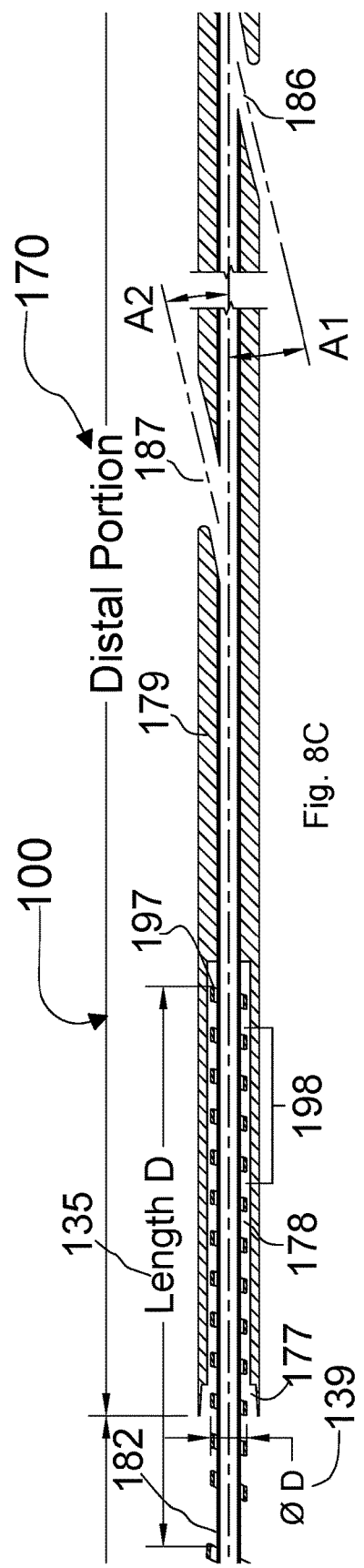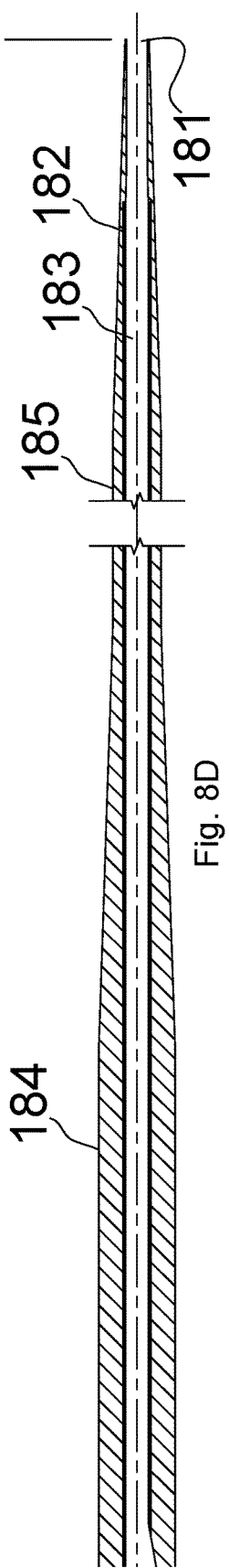

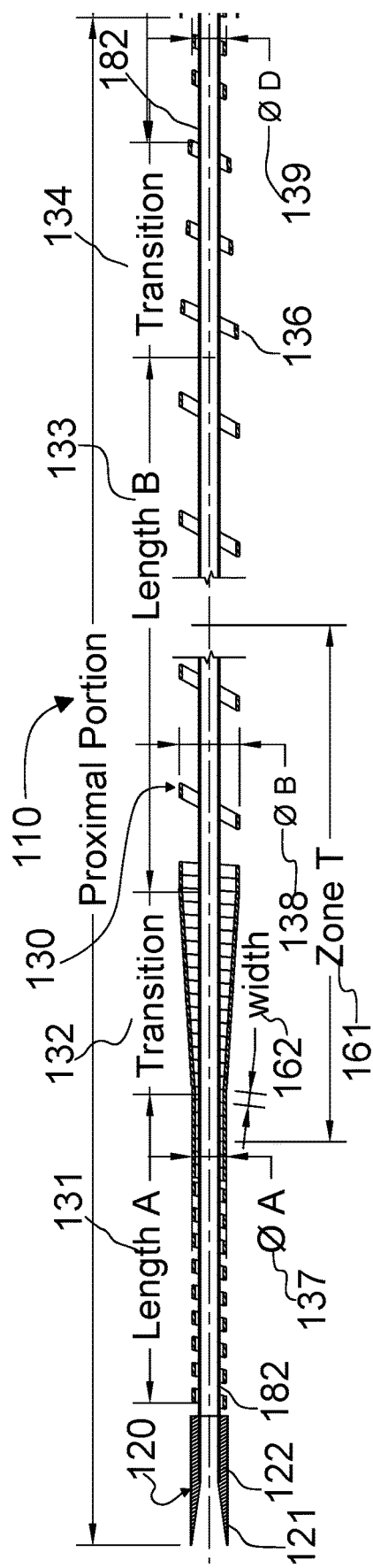
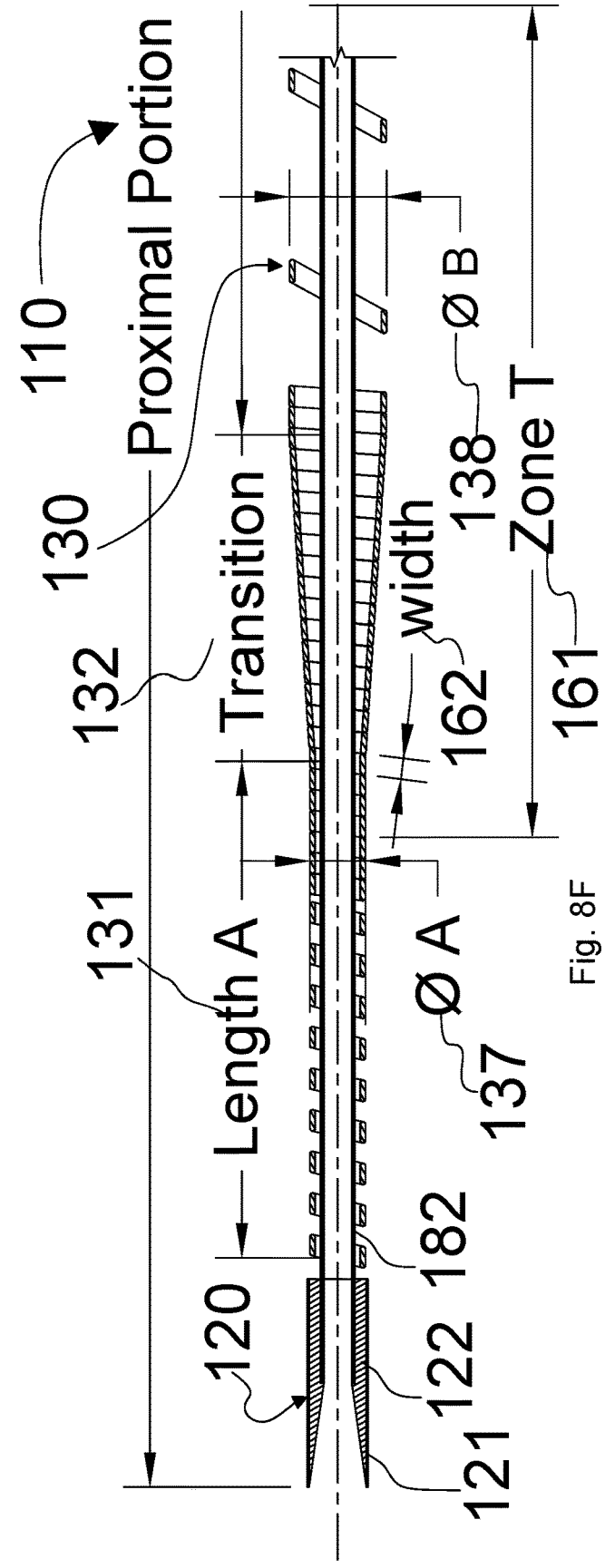
Fig. 8E
Fig. 8F

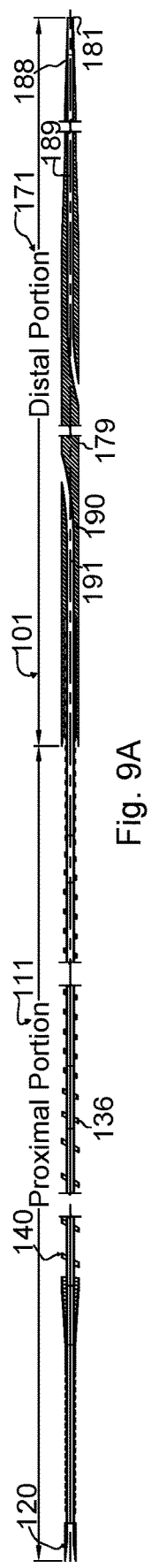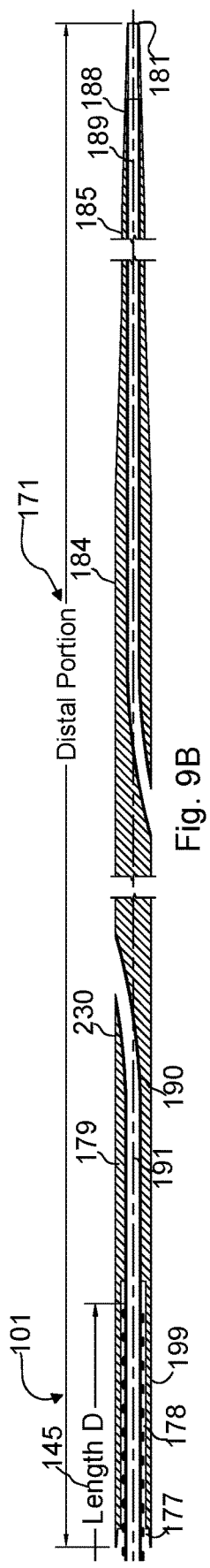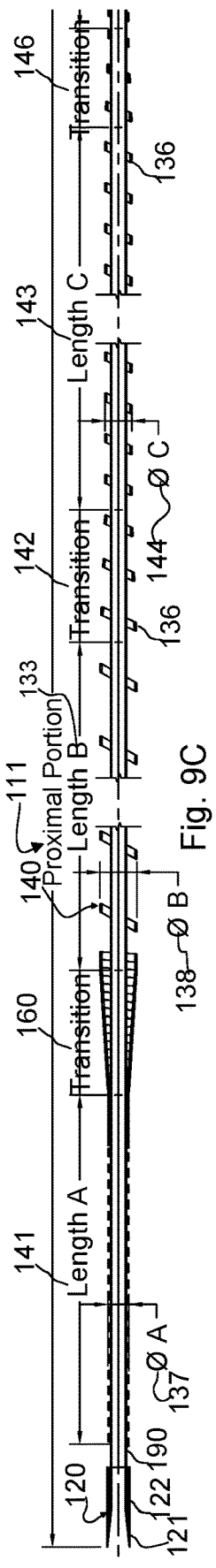
Fig. 9A
Fig. 9B
Fig. 9C

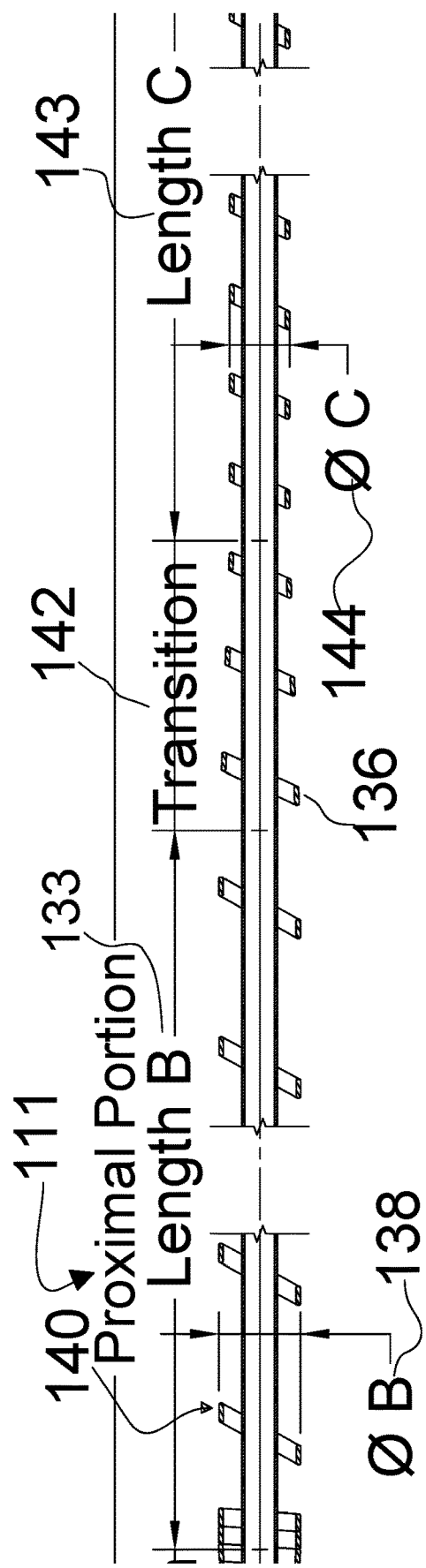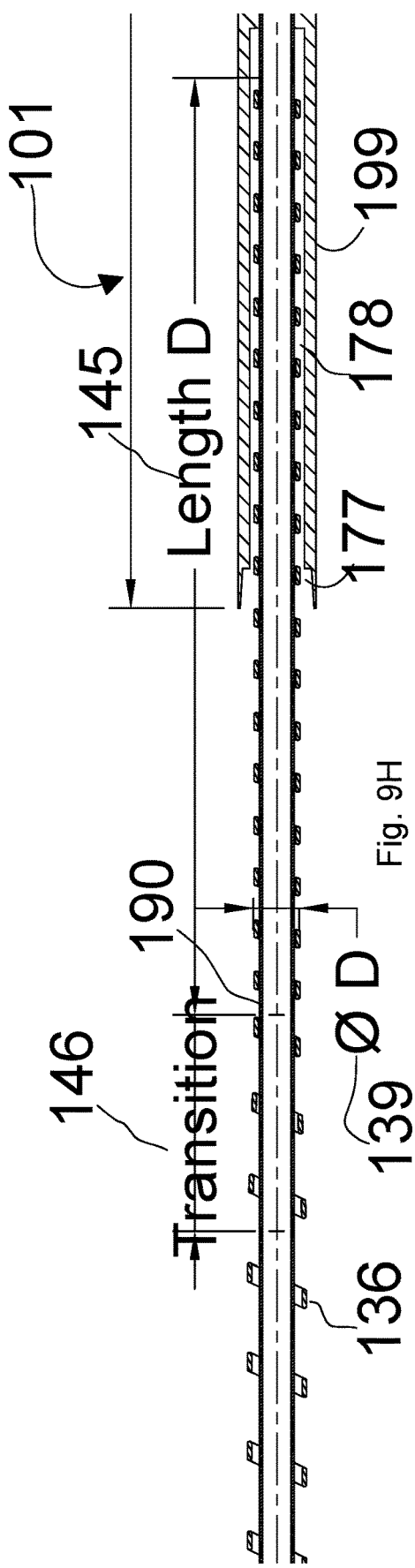

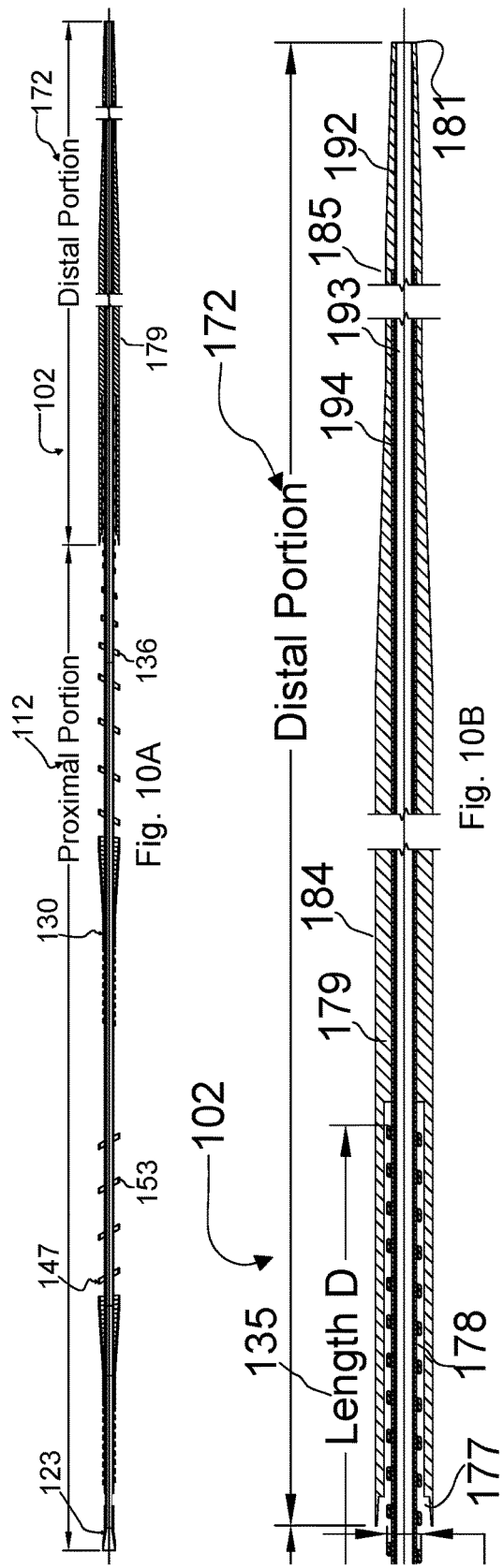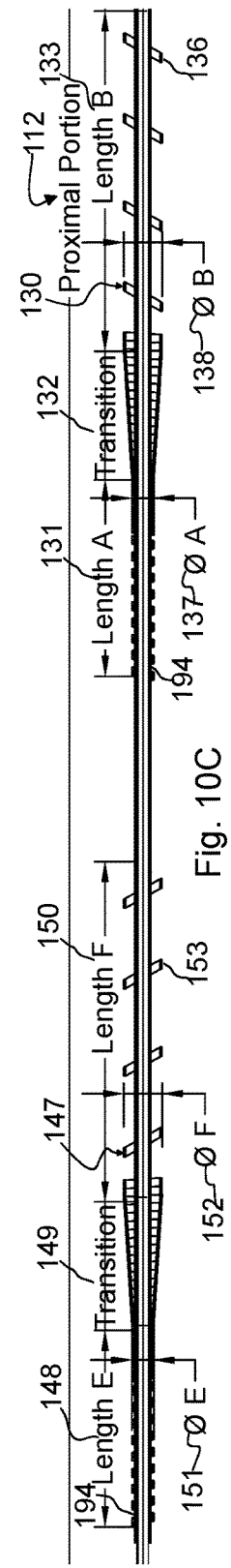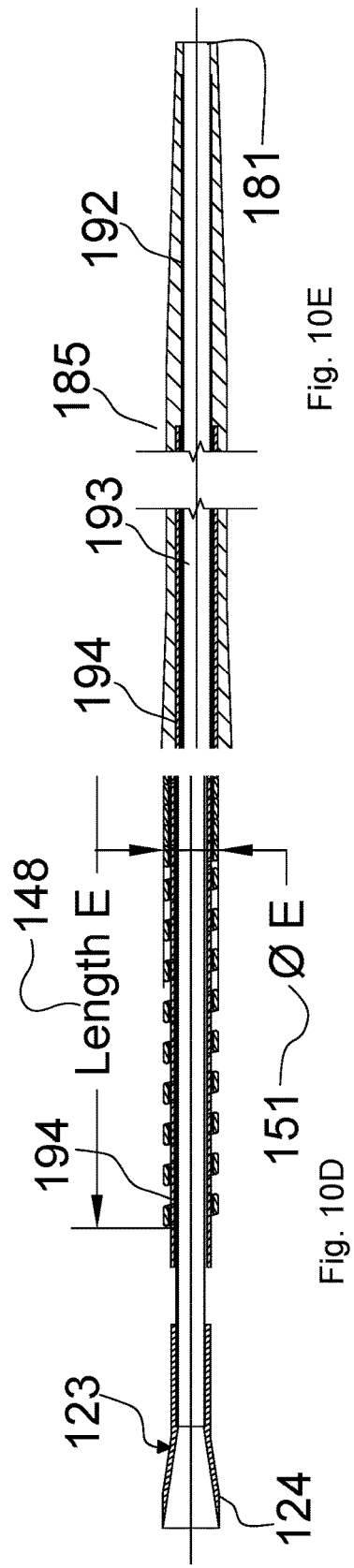

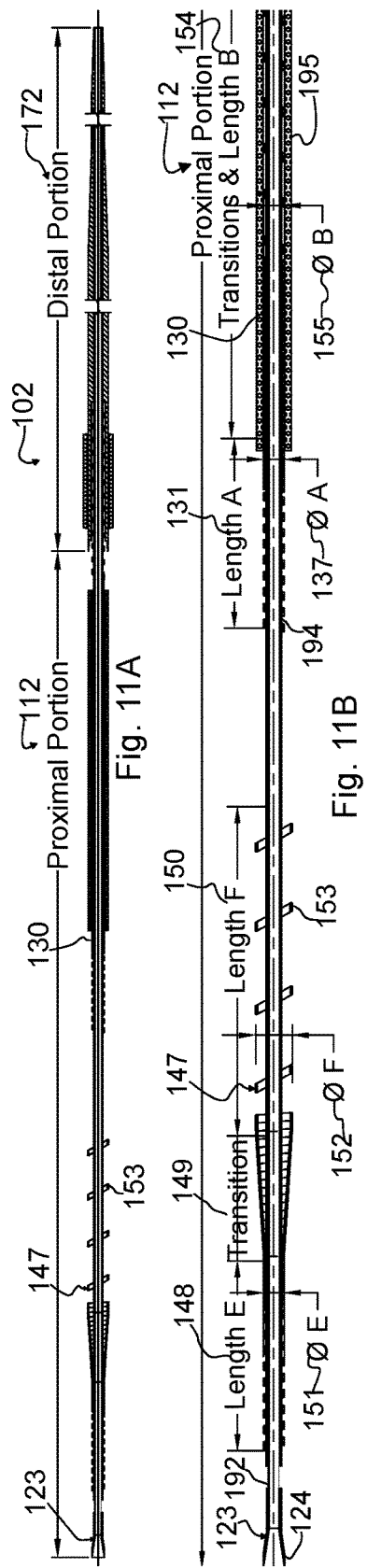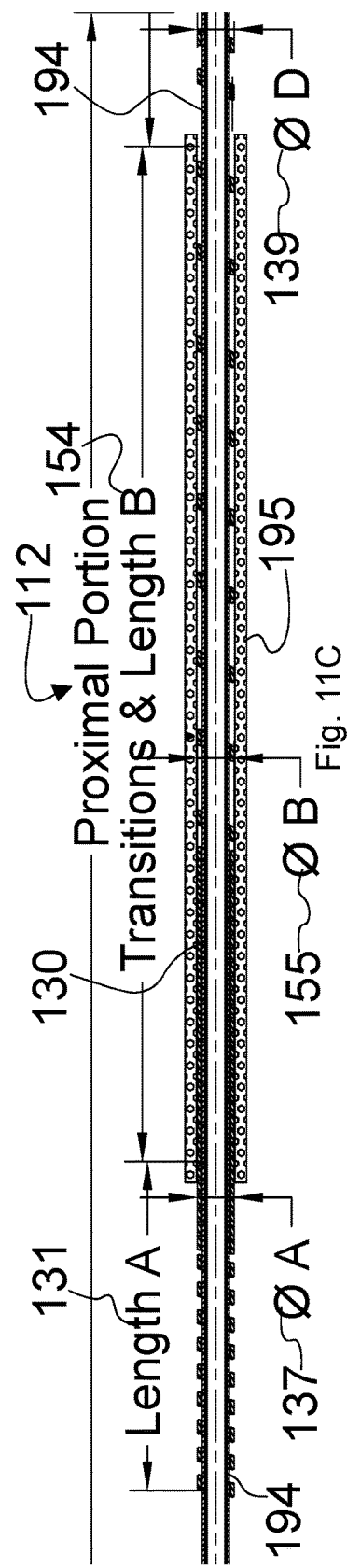

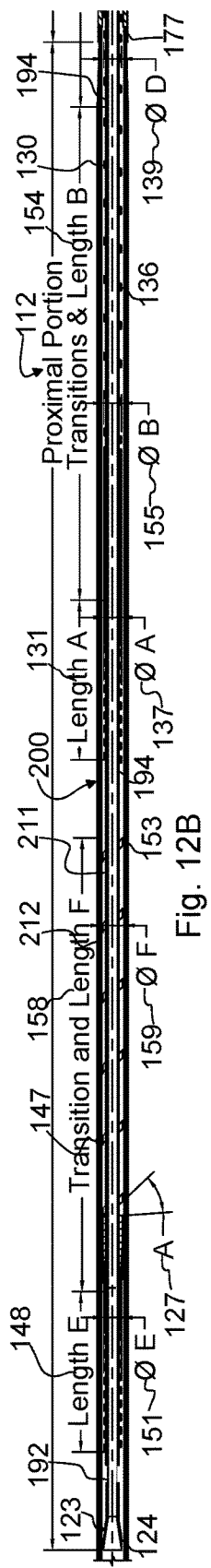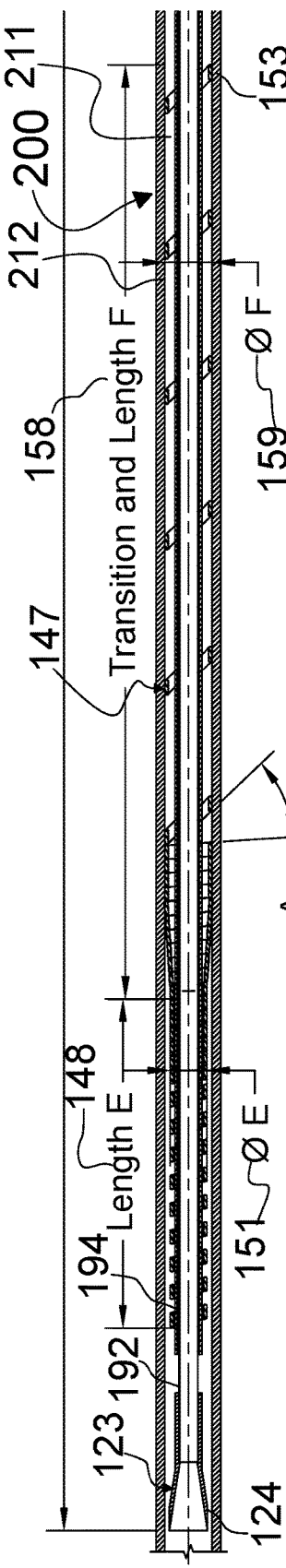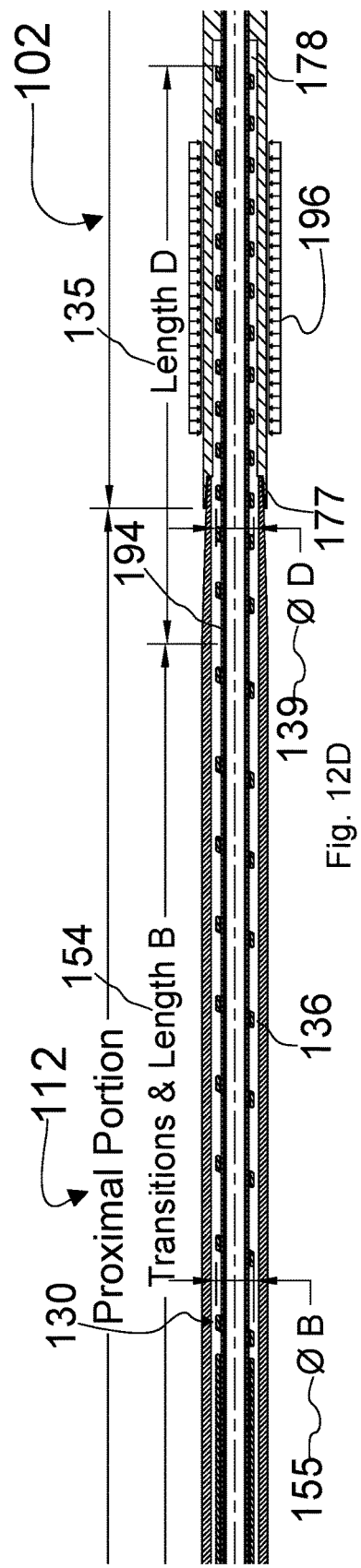

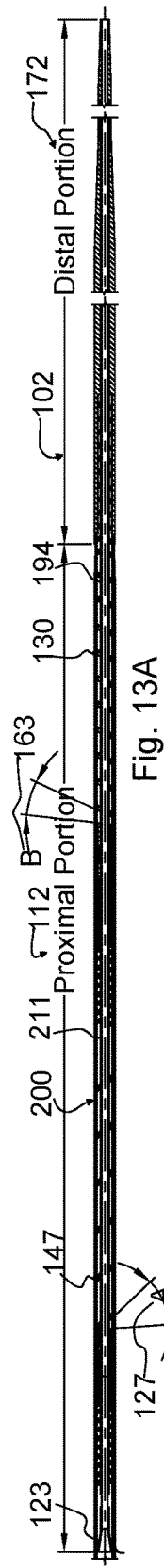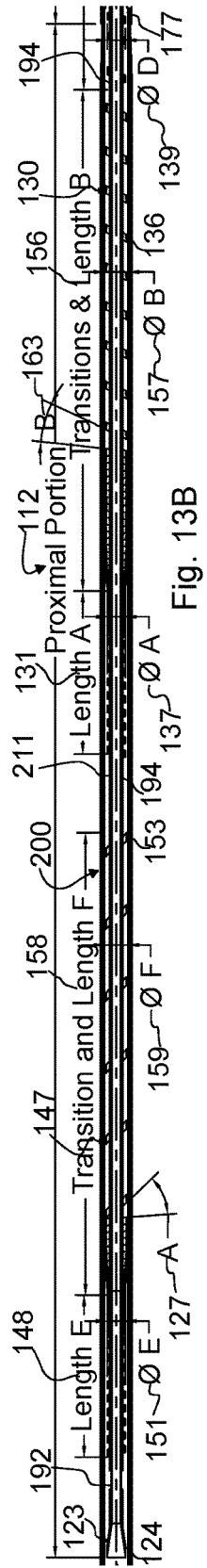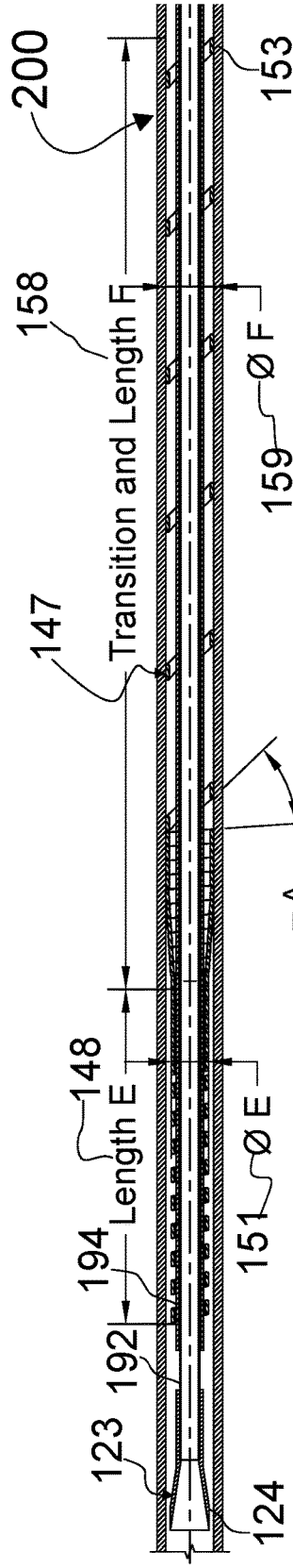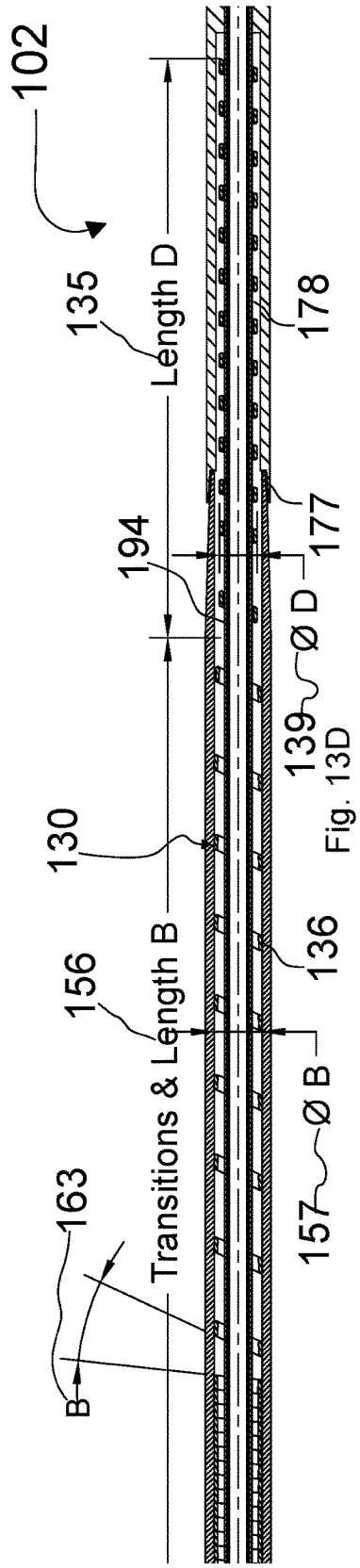
Fig. 13A
Fig. 13B
Fig. 13C
Fig. 13D

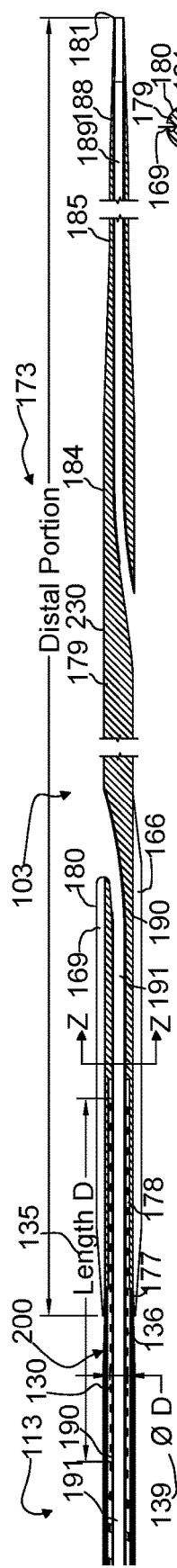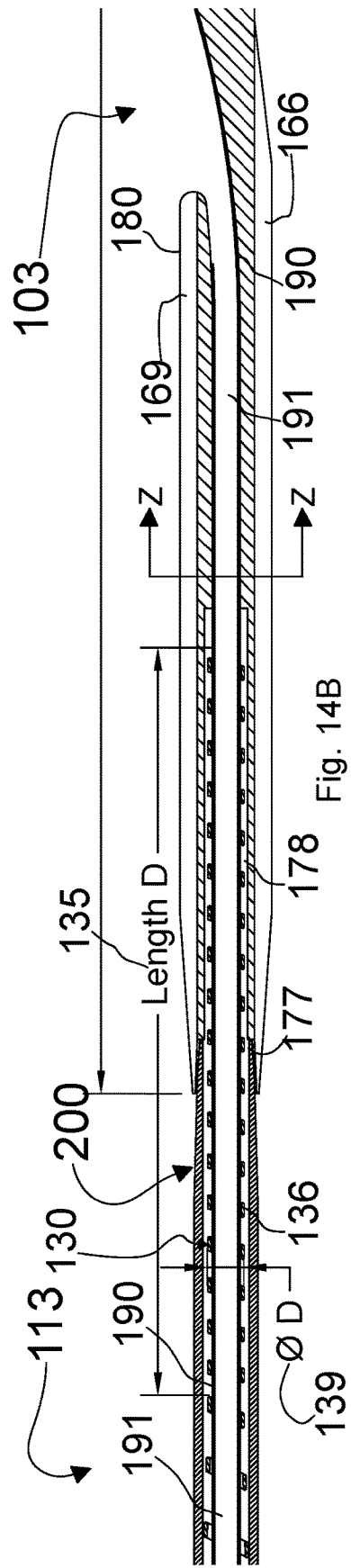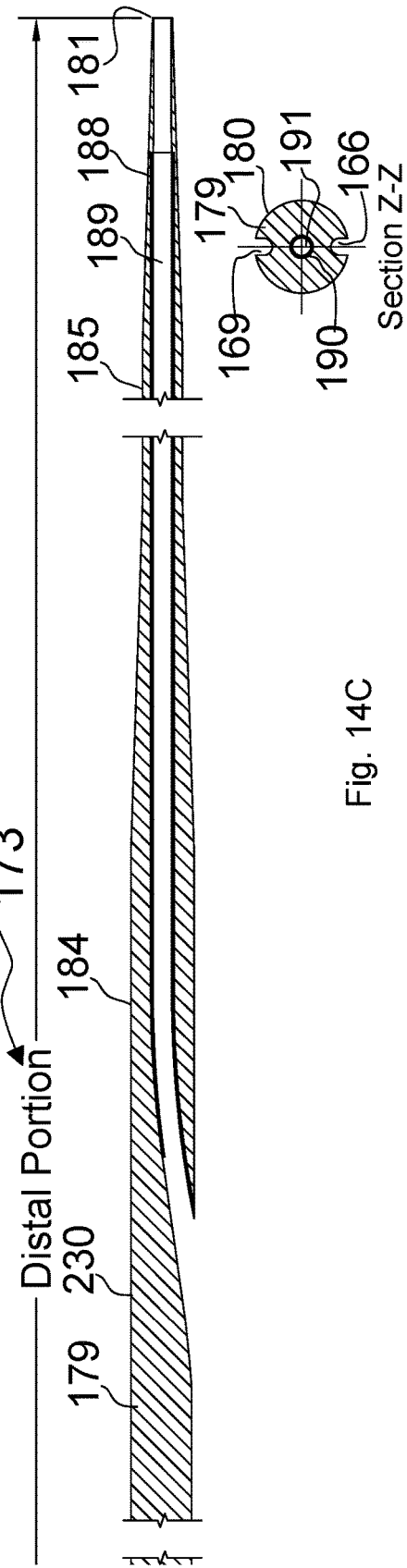
Fig. 14A
Fig. 14B
Fig. 14C

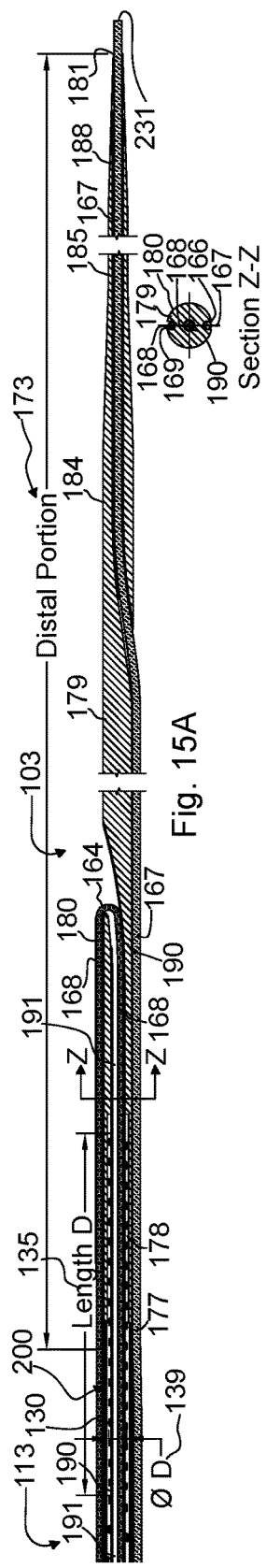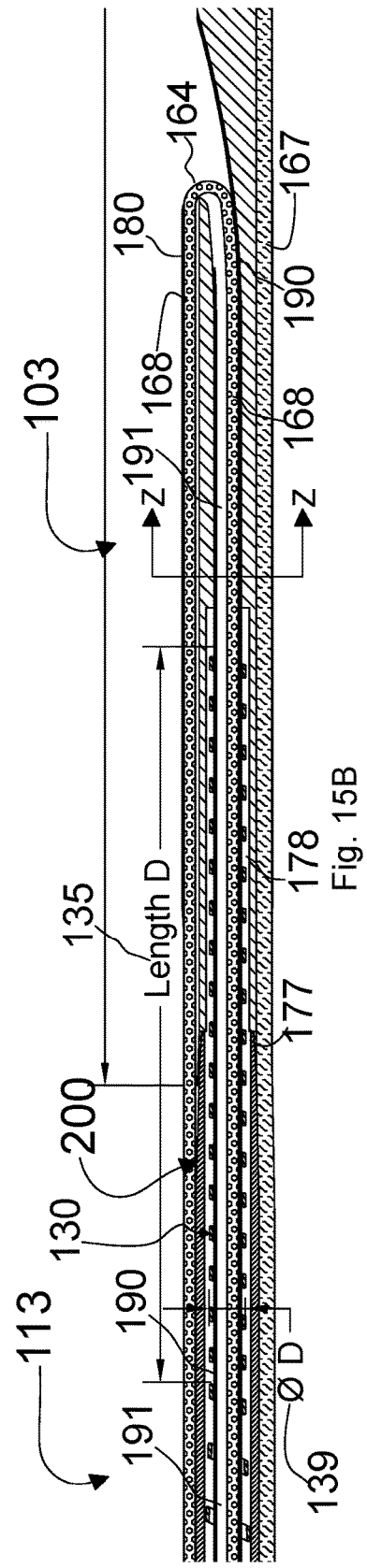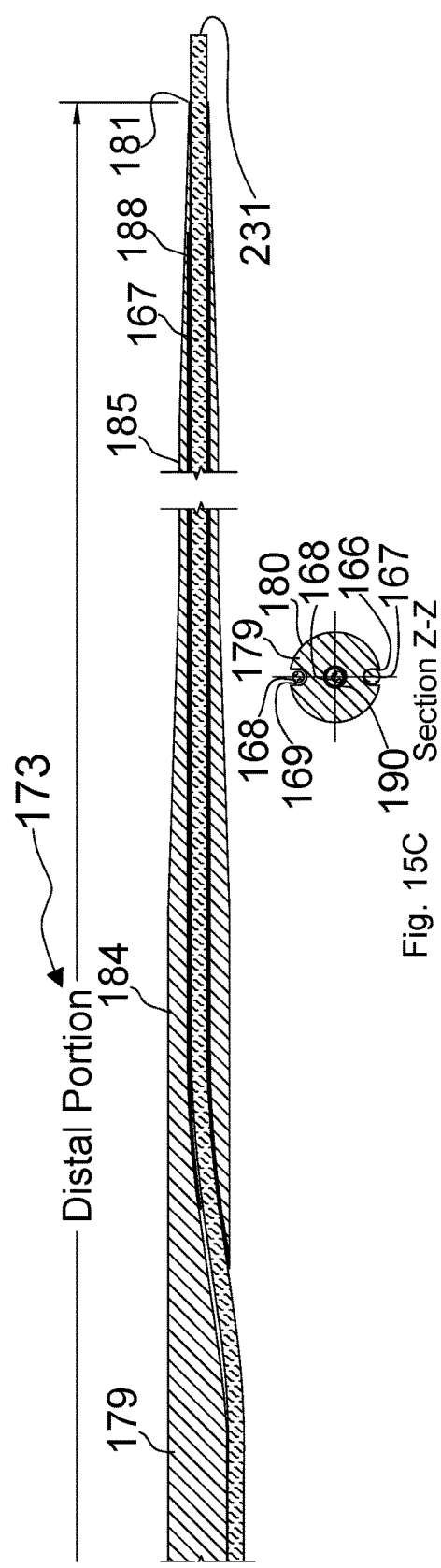

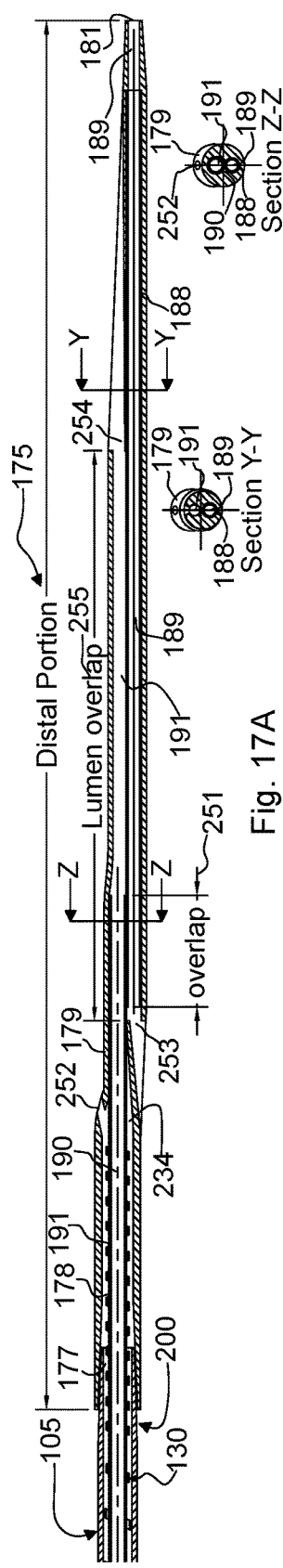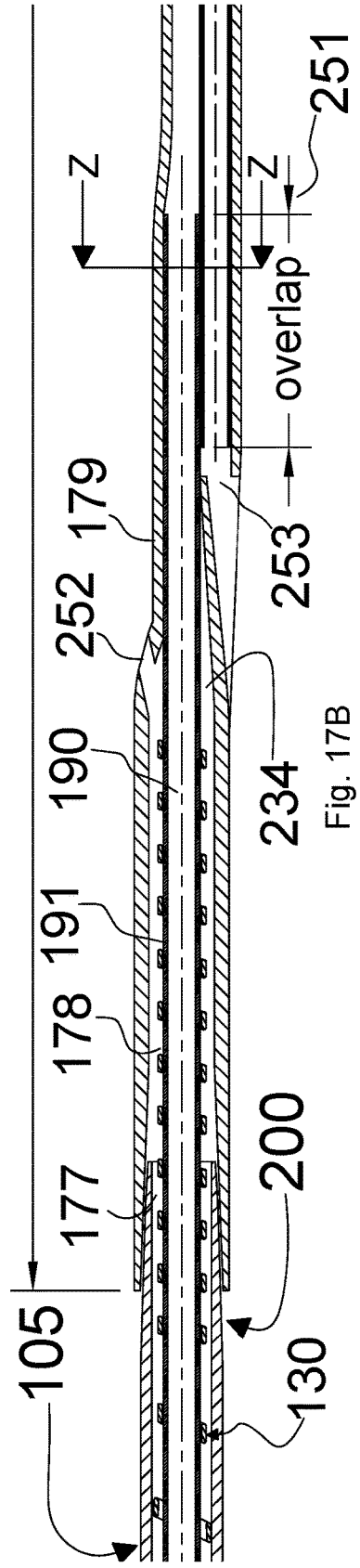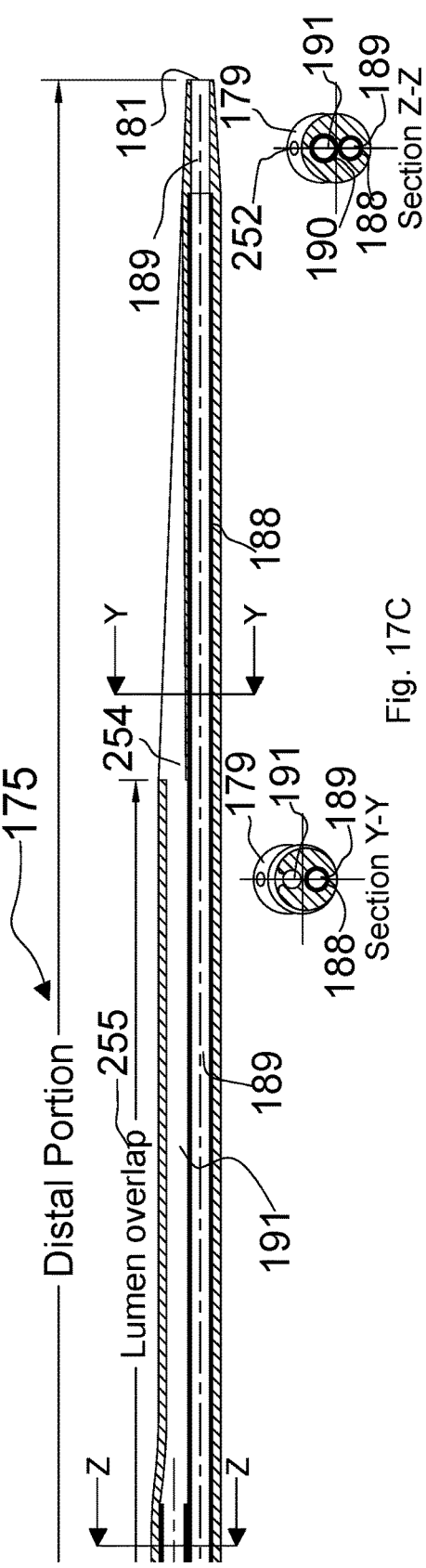
Fig. 17A
Fig. 17B
Fig. 17C

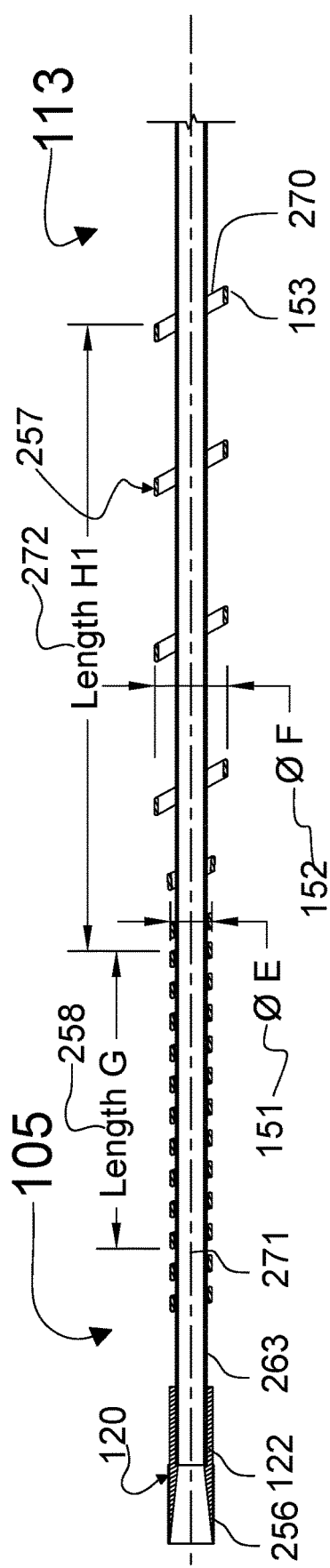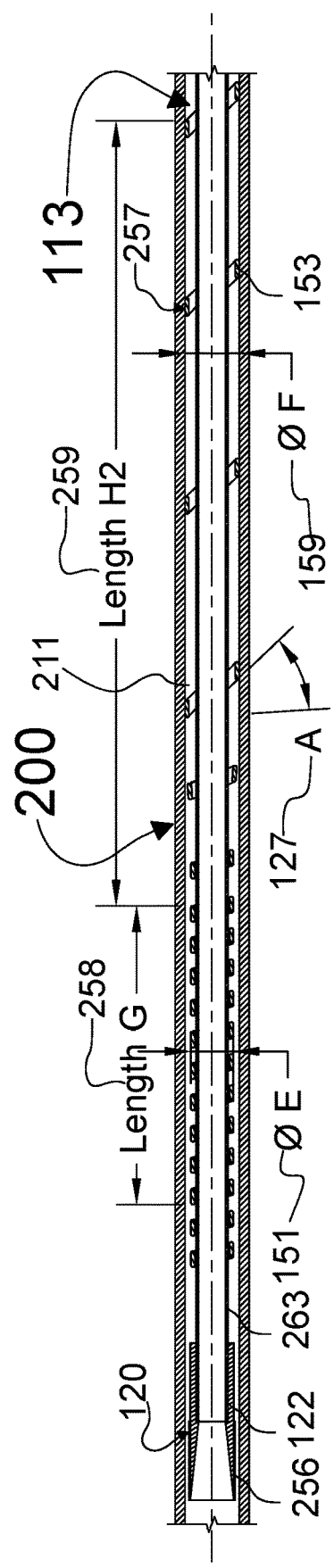

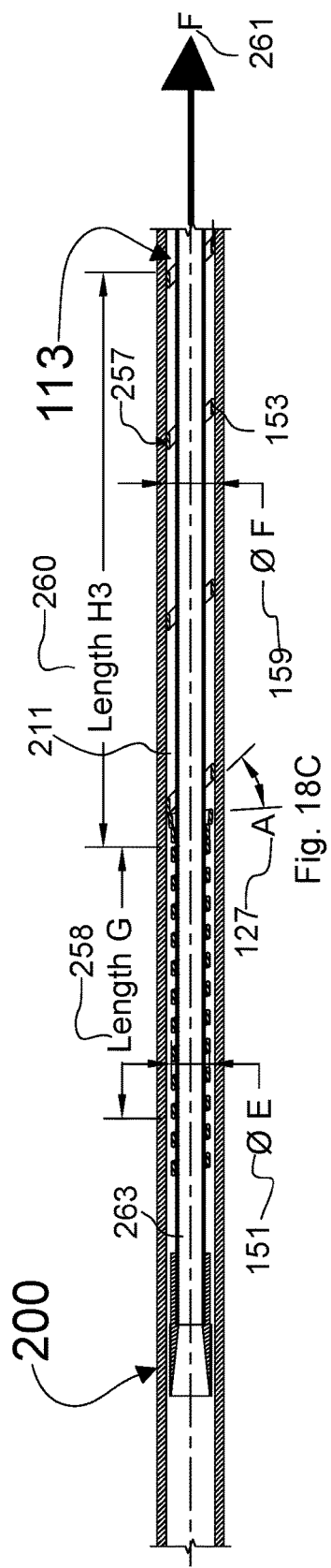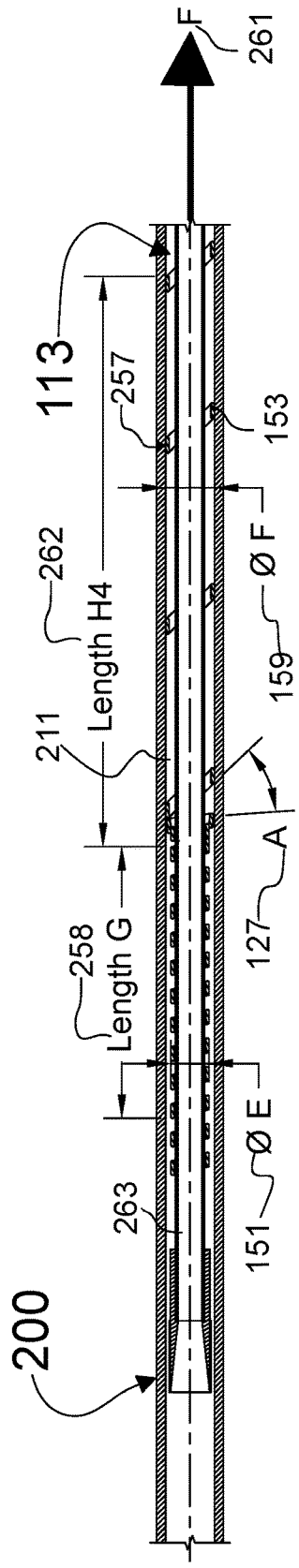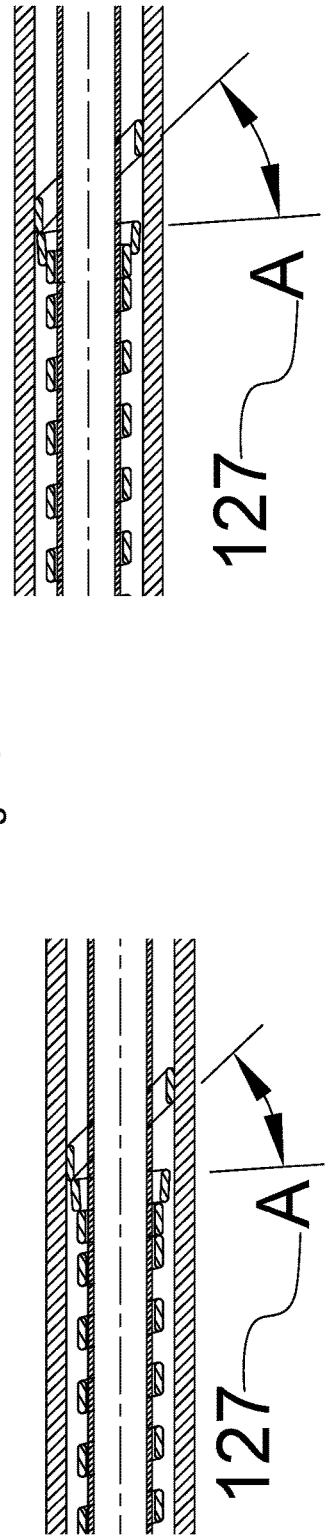

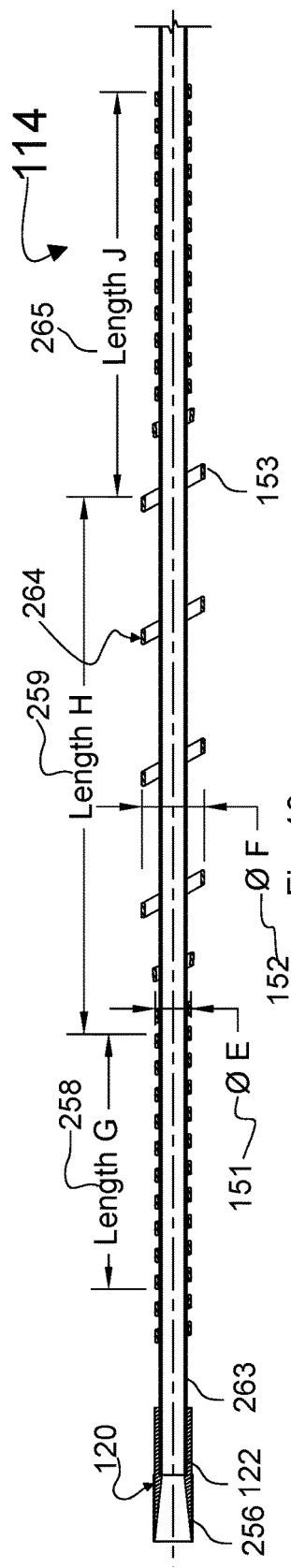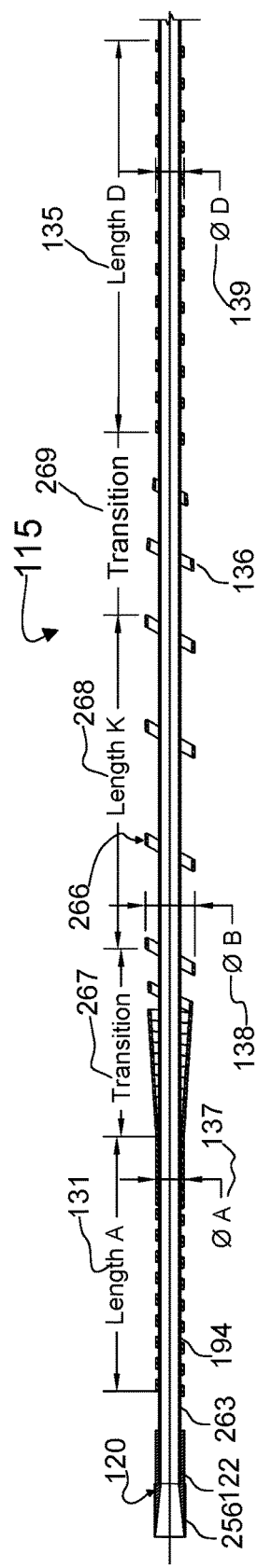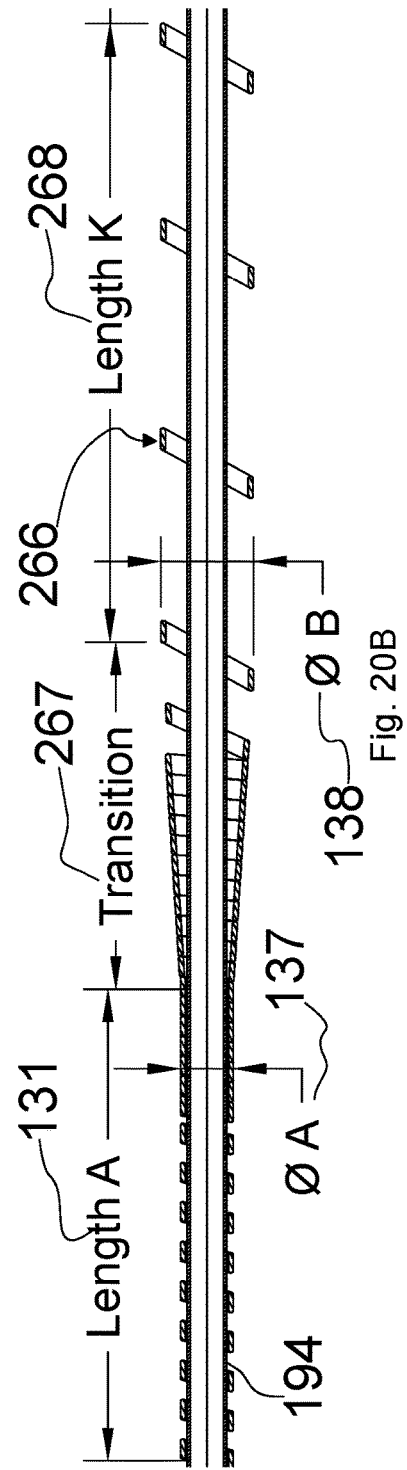
Fig. 19
Fig. 20A
Fig. 20B

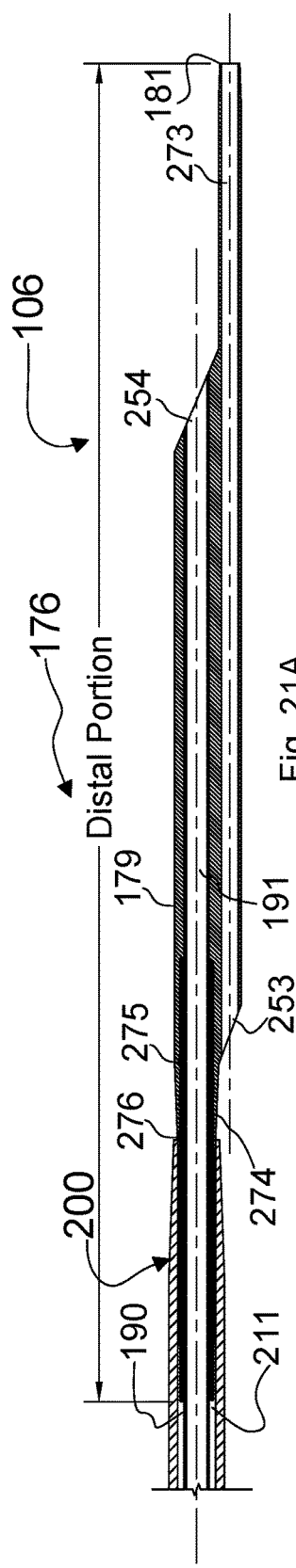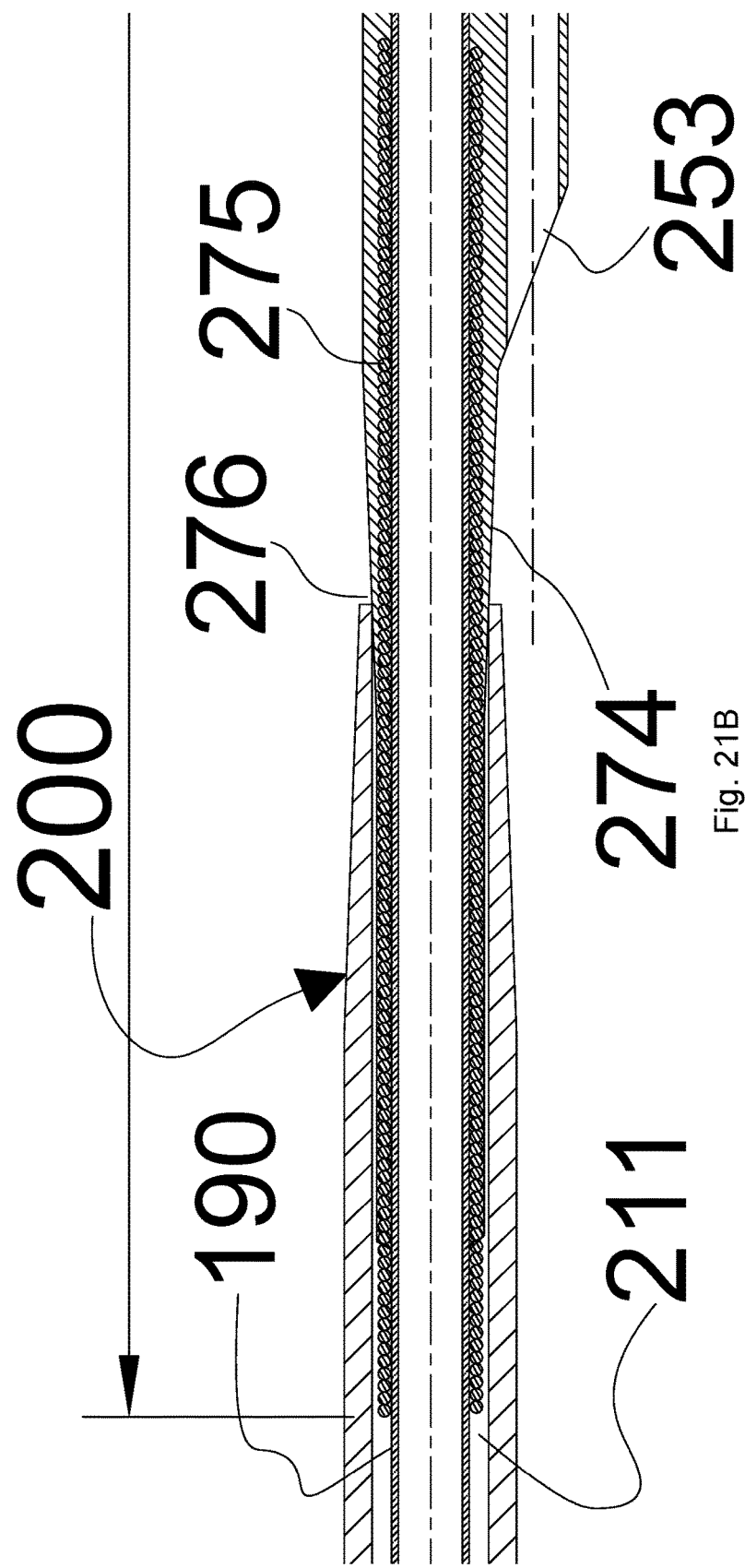
Fig. 21A
Fig. 21B

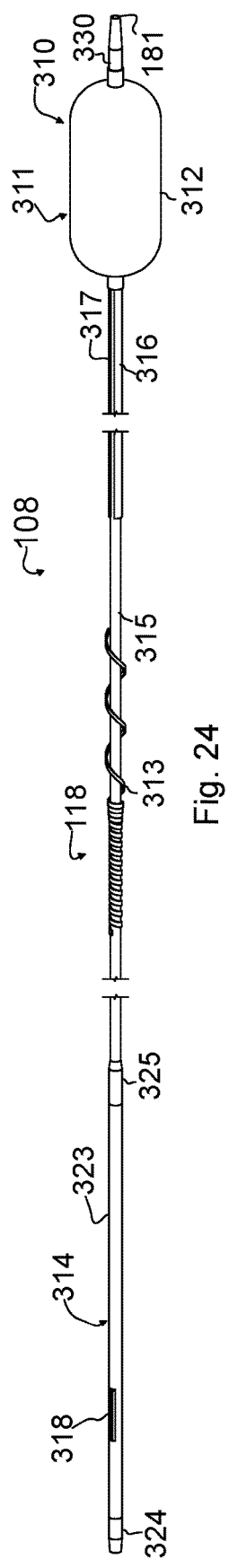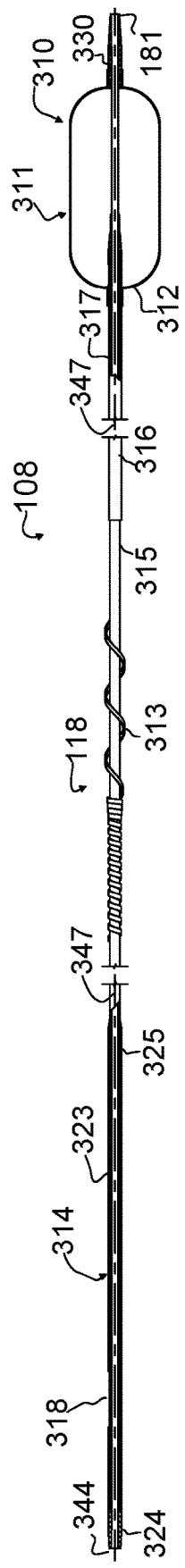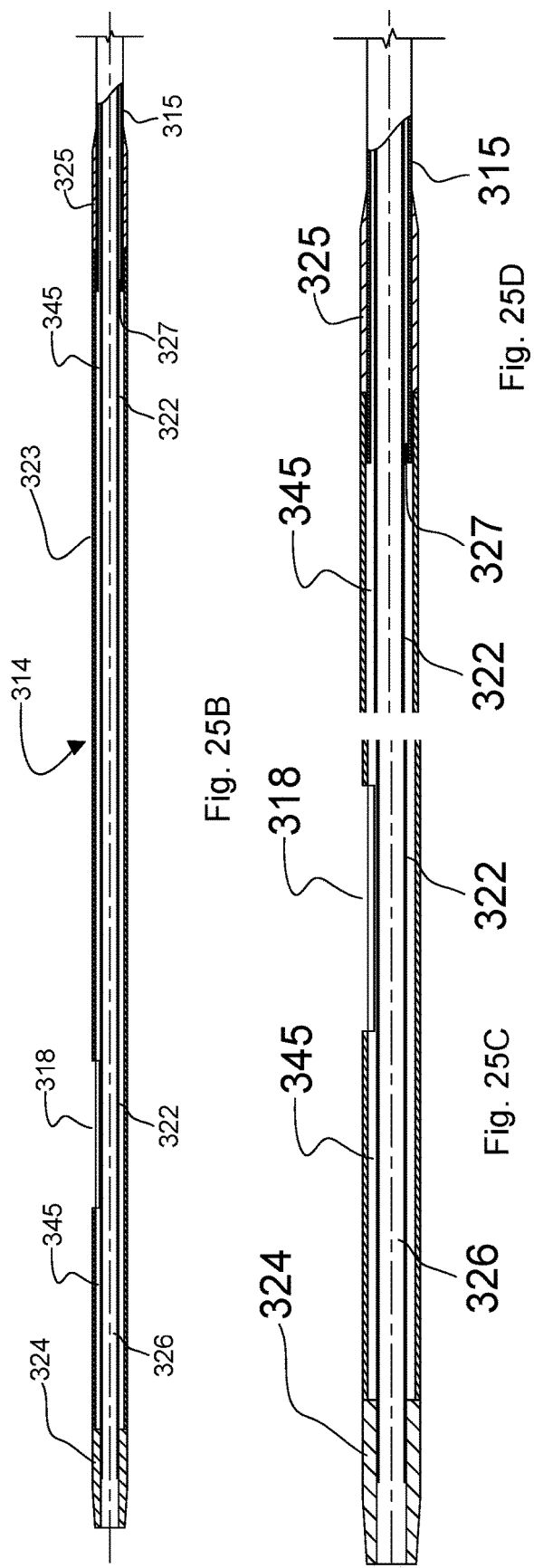
Fig. 24
Fig. 25A
Fig. 25B
Fig. 25C
Fig. 25D

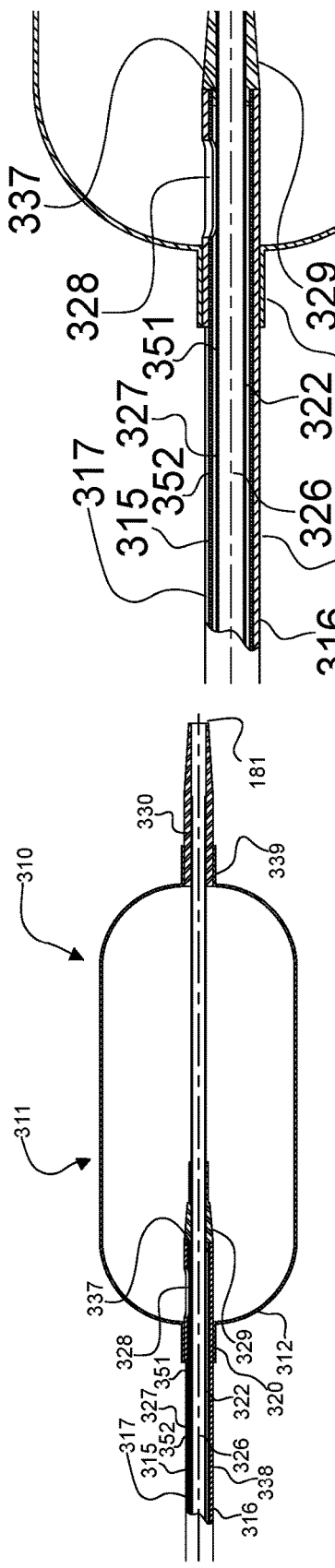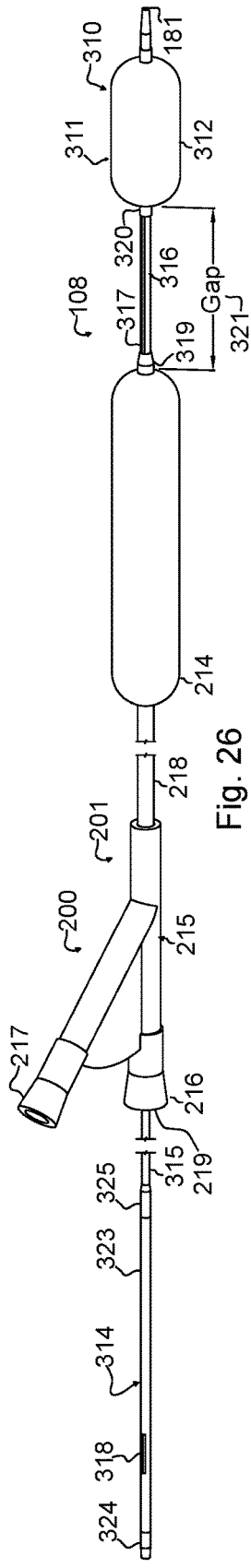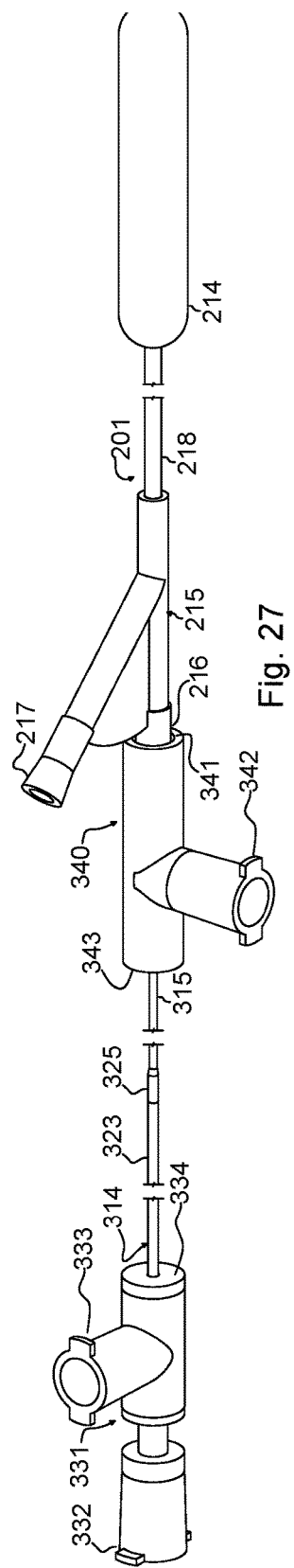
Fig. 25E
Fig. 25F
Fig. 26
Fig. 27

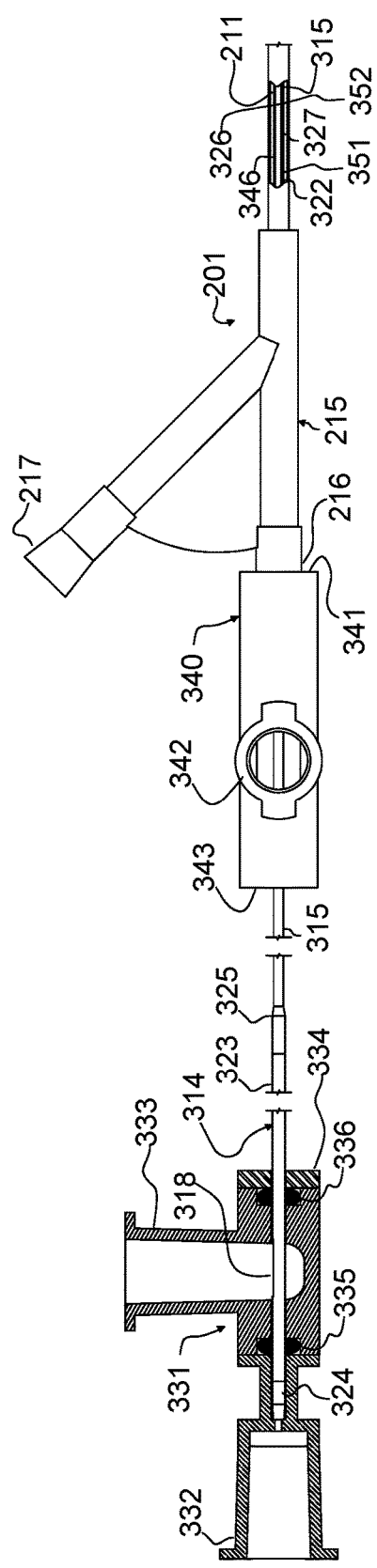
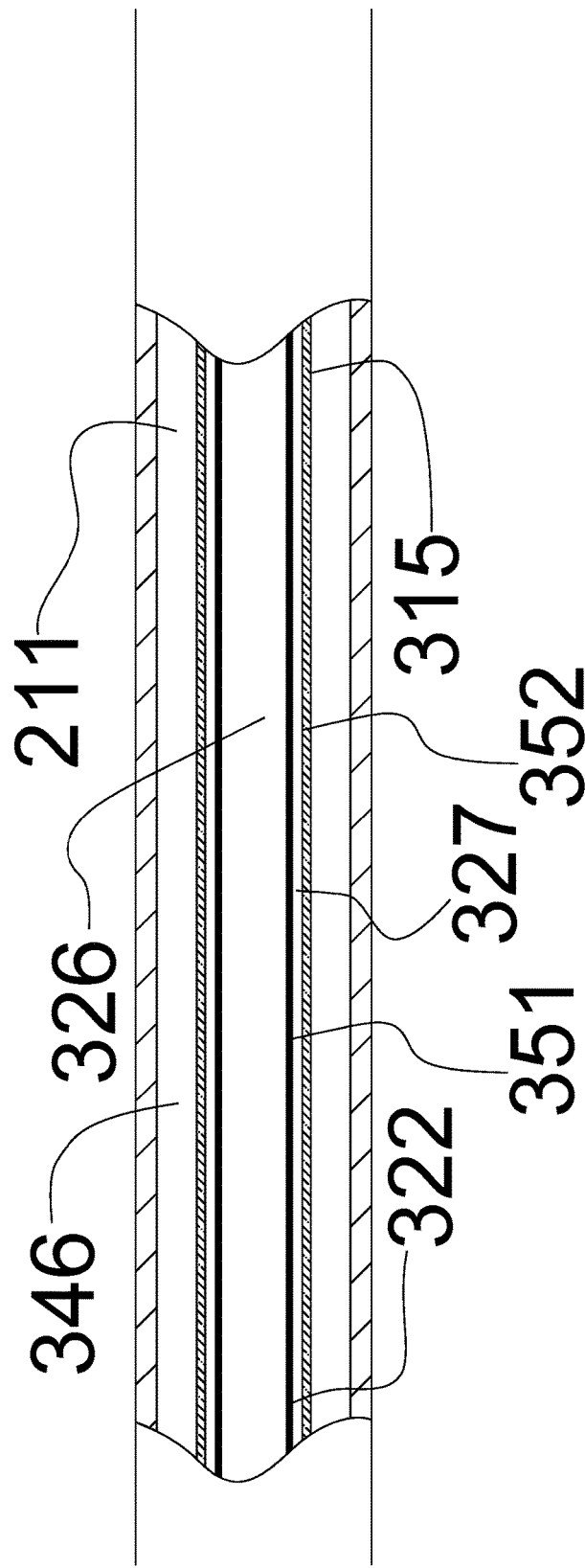
Fig. 28A
Fig. 28B

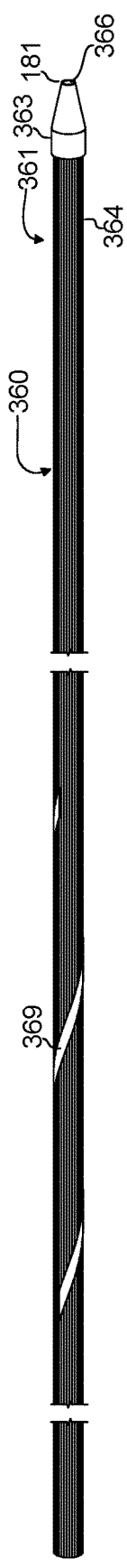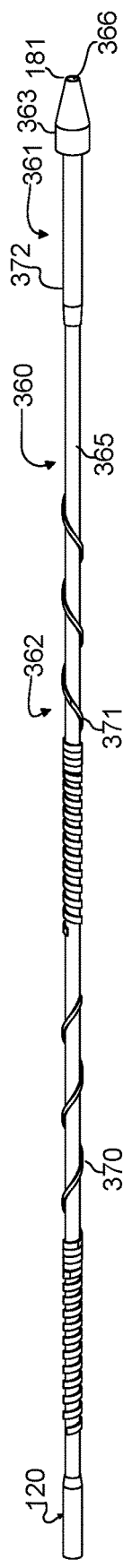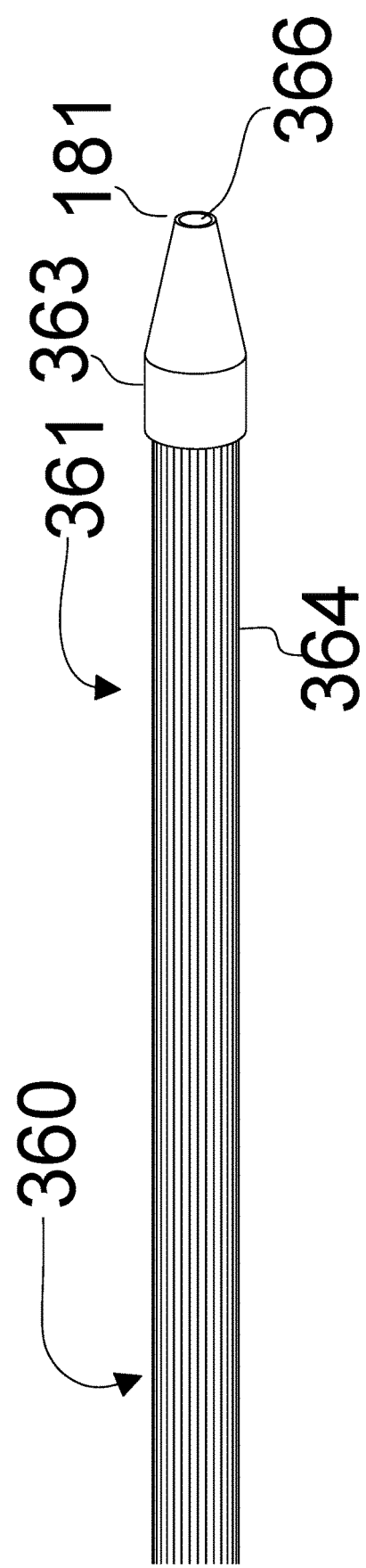

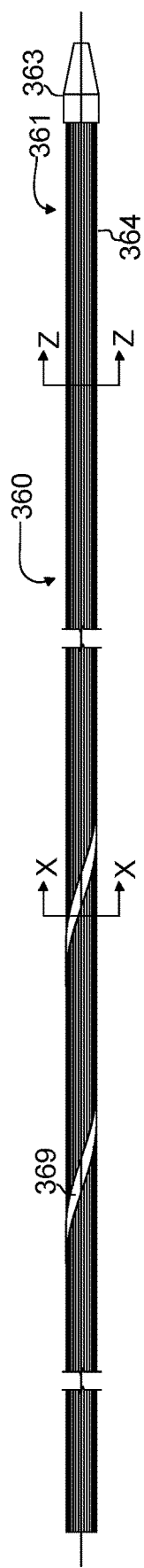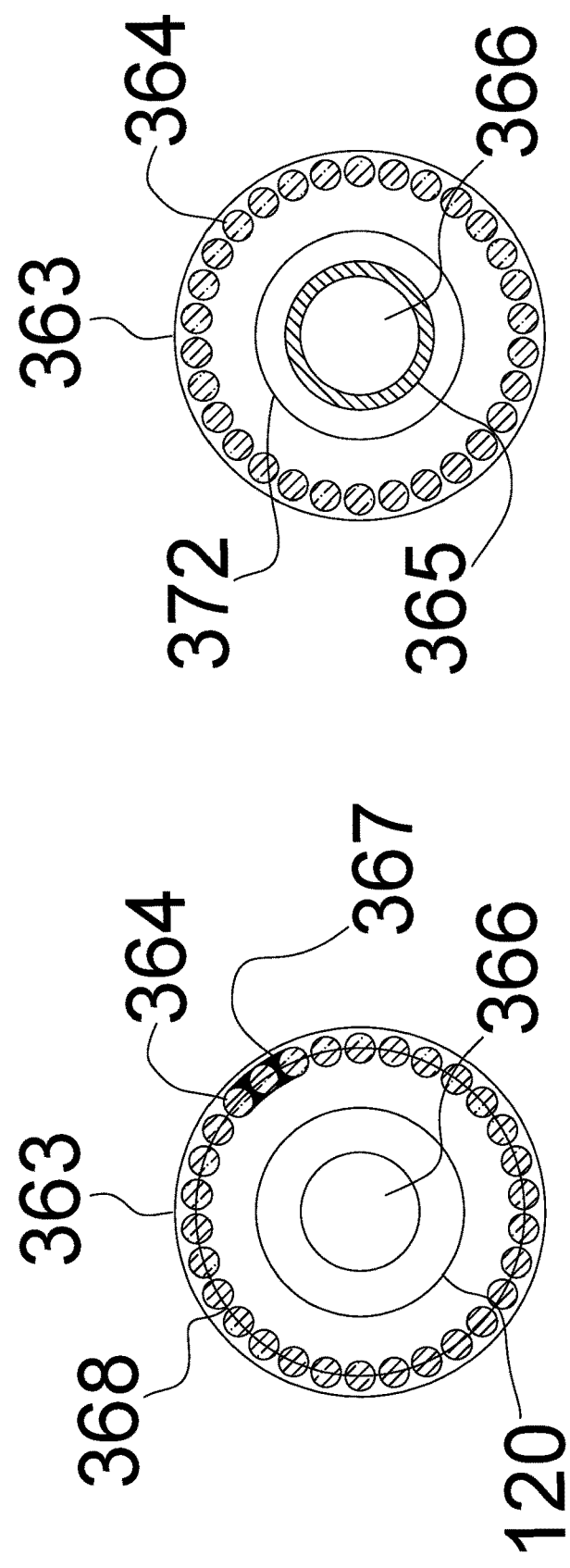

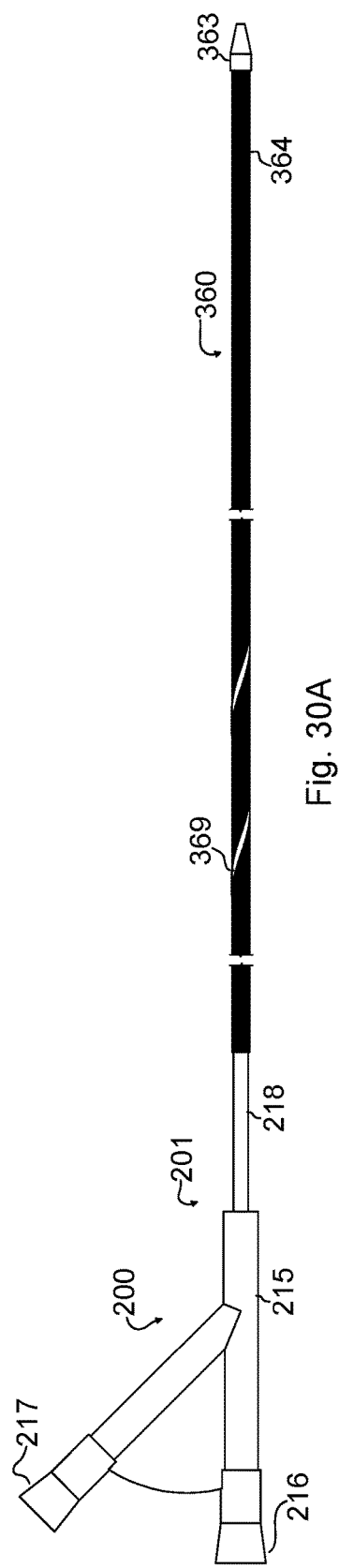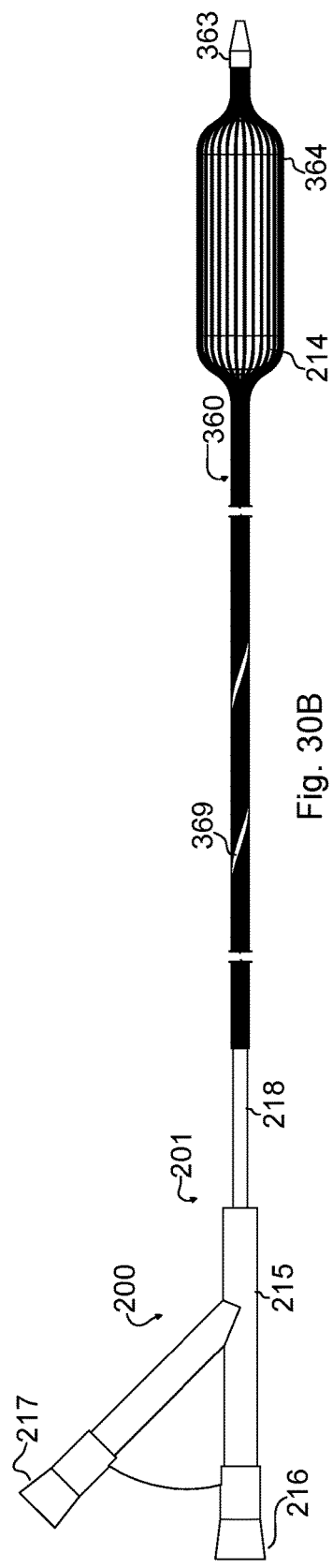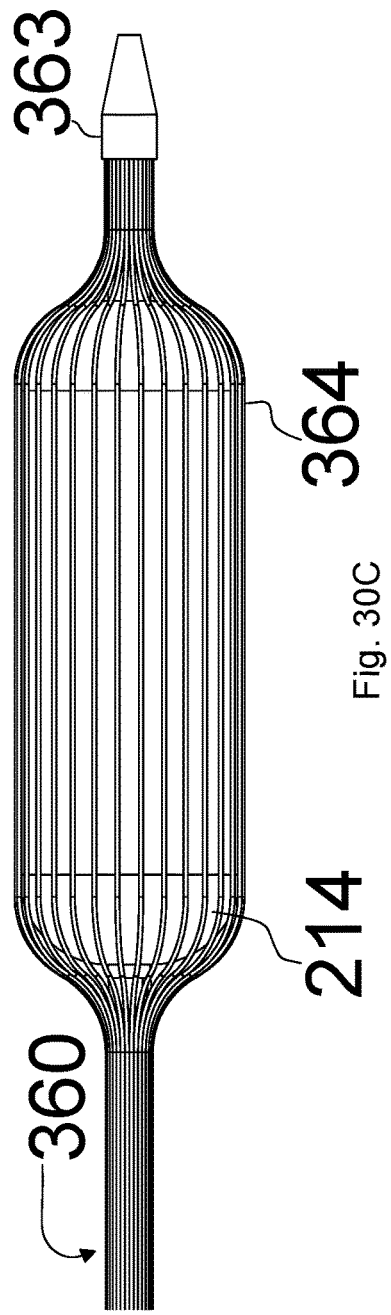

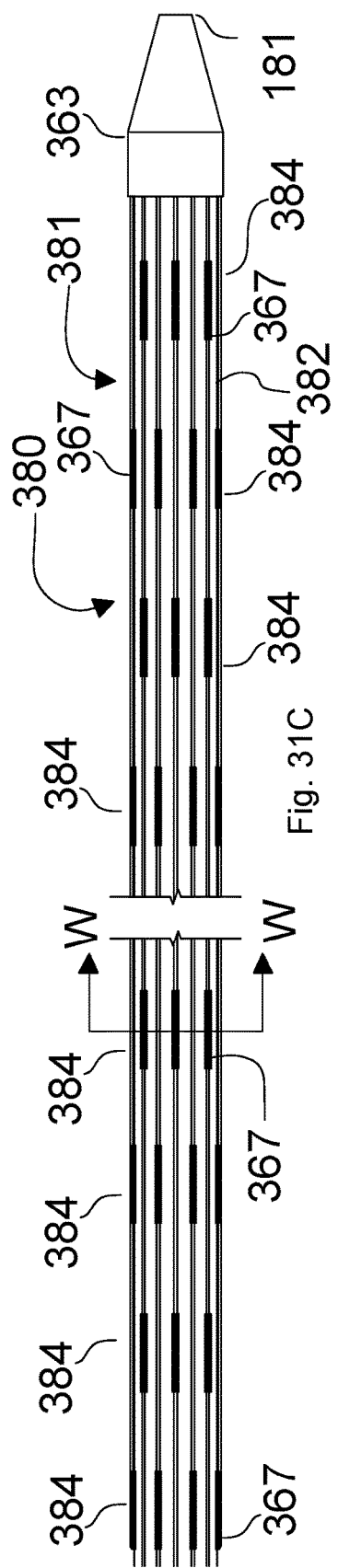

MODULAR MEDICAL DEVICE CATHETER SYSTEM

CROSS REFERENCE TO RELATED APPLICATION

This application claims the benefit of U.S. Provisional Patent Application No. 62/581,998 filed Nov. 6, 2017, and is a continuation-in-part of U.S. patent application Ser. No. 15/730,946 filed Oct. 12, 2017 (claiming the benefit of U.S. Provisional Patent Application Nos. 62/453,669 filed Feb. 2, 2017 and 62/407,557 filed Oct. 13, 2016), which is a continuation-in-part of U.S. Pat. No. 10,328,250 filed Jun. 29, 2016 (claiming the benefit of U.S. Provisional Patent Application Nos. 62/188,363 filed Jul. 2, 2015; 62/249,482 filed Nov. 2, 2015; 62/279,858 filed Jan. 18, 2016; and 62/325,700 filed Apr. 21, 2016) the entireties of which applications are hereby incorporated by reference into this application.

BACKGROUND OF THE INVENTION

1. Field of the Invention

The present invention relates generally to a design of an adapter for a medical device for use in the body and more specifically to an adapter intended to convert or augment the medical device, for example a catheter, such that the purpose or configuration of the medical device is modified or expanded.

2. Description of the Related Art

Catheter type devices are typically long tubular structures with an inner lumen suitable for a guidewire used to navigate the vasculature, inject contrast or therapeutic materials, aspirate thrombus, or provide a means to deliver other devices or therapies to a target site within the vasculature or other body lumen. Catheter type devices are typically inserted through a small opening in the skin or another opening under visual guidance tracked to the target location within the body.

U.S. Patent Application Publication No. 2007/0244440 discloses a medical device including a catheter with an expandable tip for use with at least two different sizes of wire guides. The catheter includes a wire guide lumen sized to receive a first wire guide of a first diameter. The catheter may also include a tip lumen that extends in a distal direction from a first opening in communication with the wire guide lumen to a second opening. The first opening is sized to receive the first wire guide, and the second opening is sized to receive a second wire guide of a smaller diameter than the first wire guide. The catheter also includes one or more longitudinal expansion features capable of radially expanding the tip lumen to receive a wire guide of a diameter up to the first diameter through the second opening.

U.S. Pat. No. 8,100,884 discloses an adapter assembly for connecting a catheter assembly to a tunneler having a generally tubular body having a first end, a second end and a longitudinal axis extending there through between the first end and the second end. The first end of the adapter is constructed to engage the proximal end of a trocar. The second end of the adapter is constructed to releasably engage at least one catheter lumen. A slider is disposed about the adapter and is longitudinally slidable along the adapter. When the slider is slid towards the second end of the adapter, the slider engages a plurality of legs on the adapter and biases the plurality of legs toward each other and the longitudinal axis of the adapter.

U.S. Pat. No. 8,523,840 discloses coupler assemblies to be used with a catheter to connect a proximal end of the catheter to extracorporeal medical equipment. An exemplary coupler assembly includes a spherical linkage coupler for a catheter. The coupler comprises a first cylinder portion for connecting to a structure, and a second cylinder portion for connecting to a distal end of a body of the catheter. The coupler also comprises a spherical linkage including at least two link arms. Each of the two link arms are connected on one end to the first cylinder portion and on the other end to the second cylinder portion. The two link arms connect a portion of the structure to the distal end of the catheter and enable the structure to move relative to the distal end of the catheter in response to an external force exerted on the structure.

U.S. Pat. Nos. 9,282,991; 9,808,276; 7,976,557; and U.S. Publication No. 2006/0259005 describe variations of a method of delivering a therapeutic agent, such as a drug, using a cutting balloon wherein the cutting or scoring members may comprise the therapeutic agent coated thereon. The cutting or scoring members are integral with the construction of the balloon and catheter system itself.

It is desirable to provide an improved adapter and modular system designed with features that expand, augment, or modify the configuration or intended use of a medical device. The adapter including geometry, mechanical and/or thermal properties to expeditiously attach to the medical device, such as a catheter.

SUMMARY OF THE INVENTION

In accordance with the present invention, an adapter is constructed to have a proximal portion that interfaces with the internal lumen of a medical device and a distal portion that modifies, augments or extends the configuration or intended use of the medical device. As an example, the medical device can be a catheter. The proximal portion of the adapter interfaces with the internal lumen of the medical device in a manner to secure the adapter to the medical device during use. The distal portion of the adapter is generally outside the lumen of the catheter or device and is designed with features that expand, augment, or modify the configuration or intended use of the medical device.

The proximal portion of the adapter is designed to provide an interference fit with an internal lumen of the medical device such that during subsequent use the adapter remains secure. The proximal portion is additionally designed to be easily inserted into the internal lumen of medical device. The proximal portion of the adapter includes an attachment mechanism, more completely described below, that provides securement between the adapter and medical device. The adapter and medical device comprise two modules of a modular medical device catheter system. The attachment mechanism allows an adapter module and a medical device module, also referred to as the parent module, to be combined as required by the physician or physician's staff in the operating room during a medical procedure to create a modular medical device catheter. Varying combinations of adapter modules, or adapters and parent modules or parents, allows multiple variants of a medical device catheter to be created. This modular medical device catheter system provides the physician with flexibility benefit to construct a medical device catheter for a specific procedural need and the hospital with inventory benefit, i.e. more medical device catheter variants from fewer inventory items or modules.

In one embodiment, the proximal portion of the adapter includes a coil structure having geometry and mechanical/thermal properties such that the structure is slightly smaller than the internal lumen to fit within the internal lumen in the operating room environment temperature and then expands to a larger size to secure the adapter to the internal lumen of the medical device when it is in-vivo closer to body temperature. For example, the coil structure can be formed of nitinol at a predetermined austentic finish (AF) temperature less than body temperature but greater than the temperature typically expected in an operating room or catheter lab. Alternatively, the coil structure can be physically restrained to have a size smaller than the internal lumen in the operating room environment and then expands to interface with the internal lumen of the medical device once the adapter is seated with the medical device and the physical restraint is removed. Alternatively, the coil structure can be configured to compress as it is inserted into the internal lumen of the medical device and provide securement.

The proximal portion can include an internal lumen to preserve a path for a guidewire, or for contrast injection for example. The proximal portion can include a braided structure or slotted tube stent-like geometry which can be compressed to a smaller size and then expanded to secure the adapter to the internal lumen of the catheter or other device.

The distal portion of the adapter can be used to modify the configuration of the medical device, for example, to convert a medical device from a single guidewire device to a two (2) guidewire device.

In another embodiment, the distal portion of the adapter can include one or more slender elements such as wires or fibers that extend proximally from the distal portion along the medical device or parent module. In one example, the adapter is attached to a balloon such that the slender elements external to the balloon create a scoring effect on a target tissue when inflated. In another example, the slender elements are coated or infused with a medical therapy or therapeutic agent, (pharmacological molecule, stem cell, or another therapeutic agent) to deliver the therapy to a body tissue. In another example, the slender elements include receptor sites to collect cells, tissue or molecules for diagnostic purposes.

If the adapter module of a modular medical device catheter includes an internal lumen, additional adapter modules can be added using this internal lumen to further add features, creating an enhanced modular medical device catheter, such as a parent plus a plurality of adapters. The modular arrangement allows a parent and adapter combination to become a parent in a new parent and adapter combination.

BRIEF DESCRIPTION OF THE DRAWINGS

The foregoing description, as well as further objects, features, and advantages of the present invention will be understood more completely from the following detailed description of presently preferred, but nonetheless illustrative embodiments in accordance with the present invention, with reference being had to the accompanying drawings, in which:

FIG. 1A is a schematic, longitudinal, cross-sectional view of an embodiment of an adapter in accordance with the teachings of the present invention and a partial schematic, longitudinal, cross-sectional view of a distal end of a medical device or parent.

FIG. 1B is an enlarged detail view of FIG. 1A, showing a proximal end of the adapter.

FIG. 1C is an enlarged detailed view of FIG. 1A, showing part of a distal portion of the adapter.

FIG. 2 is a schematic, longitudinal, cross-sectional view of the adapter where the coil of the adapter has been elongated in order to reduce the size of the coil prior to insertion into the target medical device or parent. Break line symbols are utilized to reduce the size of the drawing for clarity.

FIG. 3 is a schematic, longitudinal, cross-sectional view of the adapter where the coil of the adapter has been rotated or twisted in order to reduce the size of the coil prior to insertion into the target medical device. Break line symbols are utilized to reduce the size of the drawing for clarity.

FIG. 4 is a schematic, longitudinal, cross-sectional view of an alternate embodiment of an adapter, and a partial schematic, longitudinal, cross-sectional view of a distal end of a medical device or parent. Break line symbols are utilized to reduce the size of the drawing for clarity.

FIG. 5 is a schematic, longitudinal, cross-sectional view of an alternate embodiment of an adapter, and a partial schematic, longitudinal, cross-sectional view of a distal end of a medical device or parent. Break line symbols are utilized to reduce the size of the drawing for clarity.

FIG. 6 is a schematic, longitudinal, cross-sectional view of an alternate embodiment of an adapter, and a partial schematic, longitudinal, cross-sectional view of a distal end of a medical device or parent. Break line symbols are utilized to reduce the size of the drawing for clarity.

FIG. 7 is a schematic, longitudinal, cross-sectional view of an alternate embodiment of an adapter, where a coil of the adapter has been rotated or twisted in order to reduce the size of the coil prior to insertion into the medical device or parent. Break line symbols are utilized to reduce the size of the drawing for clarity.

FIG. 8A is a schematic, longitudinal, cross-sectional view of an adapter according an embodiment of the invention. Break line symbols are utilized to reduce the size of the drawing for clarity.

FIG. 8B is an enlarged detail view of FIG. 8A, showing a distal portion of the adapter.

FIG. 8C is an enlarged detail view of FIG. 8A, showing a proximal end of a distal portion of the adapter.

FIG. 8D is an enlarged detail view of FIG. 8A, showing a distal end of a distal portion of the adapter.

FIG. 8E is an enlarged detail view of FIG. 8A, showing a proximal portion of the adapter.

FIG. 8F is an enlarged detail view of FIG. 8A, showing a proximal end of a proximal portion of the adapter.

FIG. 9A is a schematic, longitudinal, cross-sectional view of an adapter according an embodiment of the invention. Break line symbols are utilized to reduce the size of the drawing or schematic for clarity.

FIG. 9B is an enlarged detail view of FIG. 9A, showing a distal portion of the adapter.

FIG. 9C is an enlarged detail view of FIG. 9A, showing a proximal portion of the adapter.

FIG. 9G is an enlarged detail view of FIG. 9A, showing middle elements of a proximal portion of the adapter.

FIG. 9H is an enlarged detail view of FIG. 9A, showing a distal end of a proximal portion of the adapter.

FIG. 10A is a schematic, longitudinal, cross-sectional view of an adapter according to an embodiment of the invention having two coil elements in a proximal portion of the adapter. Break line symbols are utilized to reduce the size of the drawing for clarity.

FIG. 10B is an enlarged detail view of FIG. 10A, showing a distal portion of the adapter.

FIG. 10C is an enlarged detail view of FIG. 10A, showing a proximal portion of the adapter.

FIG. 10D is an enlarged detail view of FIG. 10A, showing a proximal end of a proximal portion of the adapter.

FIG. 10E is an enlarged detail view of FIG. 10A, showing a distal end of a distal portion of the adapter.

FIG. 11A is a schematic, longitudinal, cross-sectional view of an adapter according an embodiment of the invention where a distal coil element of the adapter has been rotated or twisted in order to reduce the size of the coil prior to insertion into the target catheter or device. Break line symbols are utilized to reduce the size of the drawing for clarity.

FIG. 11B is an enlarged detail view of FIG. 11A, showing a proximal portion of the adapter.

FIG. 11C is an enlarged detail view of FIG. 11A, showing a distal end of a proximal portion of the adapter.

FIG. 11D is an enlarged detail view of FIG. 11A, showing a distal end of a proximal portion of the adapter and a proximal end of a distal portion of the adapter.

FIG. 12A is a schematic, longitudinal, cross-sectional view of an adapter according to an embodiment of the invention and a partial schematic, longitudinal, cross-sectional view of a distal end of a medical device, where a distal coil element of the adapter has been rotated or twisted in order to reduce the size of the coil prior to insertion into the target medical device and the proximal coil element that has been inserted into the medical device causing the proximal coil element to elongate and reduce in diameter. Break line symbols are utilized to reduce the size of the drawing for clarity.

FIG. 12B is an enlarged detail view of FIG. 12A, showing a proximal portion of the adapter.

FIG. 12C is an enlarged detail view of FIG. 12A, showing a proximal end of a proximal portion of the adapter, including a proximal coil element.

FIG. 12D is an enlarged detail view of FIG. 12A, showing a distal end of a proximal portion of the adapter and a proximal end of a distal portion of the adapter.

FIG. 13A is a schematic, longitudinal, cross-sectional view of an adapter according to an embodiment of the invention and a partial schematic, longitudinal, cross-sectional view of a distal end of a medical device or parent, where a distal coil element of the adapter has been rotated or twisted in order to reduce the size of the coil prior to insertion into the medical device then subsequently released to expand to an inner lumen of the medical device, and a proximal coil element that has been inserted into the medical device causing the proximal coil element to elongate and reduce in diameter. Break line symbols are utilized to reduce the size of the drawing for clarity.

FIG. 13B is an enlarged detail view of FIG. 13A, showing a proximal portion of the adapter.

FIG. 13C is an enlarged detail view of FIG. 13A, showing a proximal end of a proximal portion of the adapter, including a proximal coil element.

FIG. 13D is an enlarged detail view of FIG. 13A, showing a distal end of a proximal portion of an adapter and a proximal end of a distal portion of the adapter.

FIG. 14A is a partial schematic, longitudinal, cross-sectional view of an adapter according to an embodiment of the invention and a partial schematic, longitudinal, cross-sectional view of a distal end of a medical device, where a coil element of the adapter has been rotated or twisted in order to reduce the size of the coil prior to insertion into a medical device then subsequently released to expand to an inner lumen of the medical device, and a transverse cross-sectional view Z-Z of a distal portion of the adapter. Break line symbols are utilized to reduce the size of the schematic for clarity.

FIG. 14B is an enlarged detail view of FIG. 14A, showing a proximal end of a distal portion of an adapter.

FIG. 14C is an enlarged detail view of FIG. 14A, showing a distal end of a distal portion of the adapter and a transverse cross-sectional view Z-Z of a distal portion of the adapter.

FIG. 15A is a partial schematic, longitudinal, cross-sectional view of an adapter according an embodiment of the invention and a partial schematic, longitudinal, cross-sectional view of a distal end of a medical device, where a coil element of the adapter has been rotated or twisted in order to reduce the size of the coil prior to insertion into the medical device then subsequently released to expand to an inner lumen of the medical device and a first and second wire, and a transverse cross-sectional view Z-Z of a distal portion of the adapter. Break line symbols are utilized to reduce the size of the schematic for clarity.

FIG. 15B is an enlarged detail view of FIG. 15A, showing a proximal end of a distal portion of the adapter.

FIG. 15C is an enlarged detail view of FIG. 15A, showing a distal end of a distal portion of the adapter and a transverse cross-sectional view Z-Z of a distal portion of the adapter.

FIG. 17A is a partial schematic, longitudinal, cross-sectional view of an adapter according to an embodiment of the invention and a partial schematic, longitudinal, cross-sectional view of a distal end of a medical device, where a coil element of the adapter has been rotated or twisted in order to reduce the size of the coil prior to insertion into the target medical device then subsequently released to expand to an inner lumen of the medical device, and a transverse cross-sectional views Z-Z and Y-Y.

FIG. 17B is an enlarged detail view of FIG. 17A, showing a proximal end of a distal portion of the adapter.

FIG. 17C is an enlarged detail view of FIG. 17A, showing a distal end of a distal portion of the adapter and a transverse cross-sectional views Z-Z and Y-Y.

FIG. 18A is a partial schematic, longitudinal, cross-sectional view of a proximal portion of an adapter according to an embodiment of the invention. Break line symbols are utilized to reduce the size of the drawing or schematic for clarity.

FIG. 18B is a partial schematic, longitudinal, cross-sectional view of a proximal portion of the adapter shown in FIG. 18A, where the adapter and proximal portion has been inserted into a medical device. Break line symbols are utilized to reduce the size of the drawing or schematic for clarity.

FIG. 18C is a partial schematic, longitudinal, cross-sectional view of a proximal portion of the adapter shown in FIG. 18A, where the adapter and proximal portion has been inserted into a target medical device and a tensile force has been transmitted to a central tube axially compressing a portion of a coil. Break line symbols are utilized to reduce the size of the drawing or schematic for clarity.

FIG. 18D is a partial schematic, longitudinal, cross-sectional view of a proximal portion of the adapter, where the adapter and proximal portion has been inserted into a target medical device and a tensile force has been transmitted to a central tube axially compressing a portion of a coil. Break line symbols are utilized to reduce the size of the drawing or schematic for clarity.

FIG. 18E is an enlarged detail view of FIG. 18C showing a compressed portion of the coil.

FIG. 18F is an enlarged detail view of FIG. 18D showing a compressed portion of the coil.

FIG. 19 is a partial schematic, longitudinal, cross-sectional view of a proximal portion of an adapter according to an embodiment of the invention. Break line symbols are utilized to reduce the size of the drawing or schematic for clarity.

FIG. 20A is a partial schematic, longitudinal, cross-sectional view of a proximal portion of an adapter according to an embodiment of the invention. Break line symbols are utilized to reduce the size of the drawing or schematic for clarity.

FIG. 20B is an enlarged detail view of FIG. 20A.

FIG. 21A is a partial schematic, longitudinal, cross-sectional view of an adapter according to an embodiment of the invention, where the adapter has been inserted into a target medical device. Break line symbols are utilized to reduce the size of the drawing or schematic for clarity.

FIG. 21B is an enlarged detail view of FIG. 21A.

FIG. 24 is a schematic, perspective, view of an adapter according to an embodiment of the invention where the balloon of the adapter is represented as inflated for the purposes of illustration. Break line symbols are utilized to reduce the size of the drawing for clarity.

FIG. 25A is a schematic, longitudinal, view of an adapter according to an embodiment of the invention where the balloon of the adapter is represented as inflated for the purposes of illustration, including a partial cross-section of the distal portion containing the balloon, and partial cross-section of the proximal portion containing the inflation connector. Break line symbols are utilized to reduce the size of the drawing for clarity.

FIG. 25B is an enlarged detail view of a portion of FIG. 25A.

FIG. 25C is an enlarged detail view of a portion of FIG. 25B.

FIG. 25D is an enlarged detail view of a portion of FIG. 25B.

FIG. 25E is an enlarged detail view of a portion of FIG. 25A.

FIG. 25F is an enlarged detail view of a portion of FIG. 25E.

FIG. 26 is a schematic, perspective, view of an adapter according to an embodiment of the invention, where the balloon of the adapter is represented as inflated for the purposes of illustration, attached to a target balloon medical device which also represented as inflated for the purposes of illustration. Break line symbols are utilized to reduce the size of the drawing for clarity.

FIG. 27 is a partial schematic, perspective, view of an adapter according to an embodiment of the invention, where the balloon of the adapter is represented as inflated for the purposes of illustration, attached to a target balloon medical device which also represented as inflated for the purposes of illustration, with fittings coupled to the proximal ends of both the adapter and target balloon medical device. Break line symbols are utilized to reduce the size of the drawing for clarity.

FIG. 28A is a partial, schematic, longitudinal, view of an adapter according to an embodiment of the invention, where the balloon of the adapter is represented as inflated for the purposes of illustration, attached to a target balloon medical device which also represented as inflated for the purposes of illustration, with fittings coupled to the proximal ends of both the adapter and target balloon medical device, and includes a partial cross-section view of the target balloon medical device and one of the fittings. Break line symbols are utilized to reduce the size of the drawing for clarity.

FIG. 28B is an enlarged detail view of a portion of FIG. 28A.

FIG. 29A is a schematic view of an adapter according to an embodiment of the invention, where the adapter includes slender elements running longitudinal from the distal end of the adapter. Break line symbols are utilized to reduce the size of the drawing for clarity. Some adapter elements are obscured by the slender elements.

FIG. 29B is a schematic view of an adapter according to an embodiment of the invention represented in FIG. 29A, where the slender elements running longitudinal from the distal end of the adapter are omitted to allow the obscured adapter elements to be visible.

FIG. 29C is an enlarged detail view of a portion of FIG. 29A, showing a distal end of a distal portion of the adapter.

FIG. 29D is a schematic longitudinal orthographic view of an adapter according to an embodiment of the invention, where the adapter includes slender elements running longitudinal from the distal end of the adapter. FIG. 29D includes section arrows X-X and Z-Z. Break line symbols are utilized to reduce the size of the drawing for clarity. Some adapter elements are obscured by the slender elements.

FIG. 29E is a transverse cross-sectional view X-X of the adapter shown in FIG. 29D. View X-X includes a cross section through the slender elements and bonded portion of the slender elements of the adapter.

FIG. 29F is a transverse cross-sectional view Z-Z of the adapter shown in FIG. 29D. View Z-Z includes a cross section through the central tube and slender elements of the adapter.

FIG. 30A is a schematic view of an adapter according to an embodiment of the invention, where the adapter includes slender elements running longitudinal from the distal end of the adapter, and the adapter is attached to a target balloon catheter medical device which is represented as deflated for the purposes of illustration. Break line symbols are utilized to reduce the size of the drawing for clarity. Some adapter elements are obscured by the slender elements.

FIG. 30B is a schematic view of an adapter according to an embodiment of the invention, where the adapter includes slender elements running longitudinal from the distal end of the adapter, and the adapter is attached to a target balloon catheter medical device which is represented as inflated for the purposes of illustration. Break line symbols are utilized to reduce the size of the drawing for clarity. Some adapter elements are obscured by the slender elements.

FIG. 30C is an enlarged detail view of a portion of FIG. 30B, showing the distal end of the adapter and inflated balloon medical device.

FIG. 31B includes section arrows V-V and W-W indicating cross sections through the slender elements and bonded portion of the slender elements of the adapter at different longitudinal points along the length of the adapter. Break line symbols are utilized to reduce the size of the drawing for clarity. Some adapter elements are obscured by the slender elements.

FIG. 31C is an enlarged detail view of a portion of FIG. 31B, showing distal end of the adapter.

FIG. 31D is a transverse cross-sectional view V-V of the adapter as shown in FIG. 31B. View V-V includes a cross section through the slender elements and bonded portion of the slender elements of the adapter.

FIG. 31E is a transverse cross-sectional view W-W of the adapter as shown in FIG. 31B. View W-W includes a cross section through the slender elements and bonded portion of the slender elements of the adapter.

DETAILED DESCRIPTION OF THE PREFERRED EMBODIMENTS

Figure 9D:
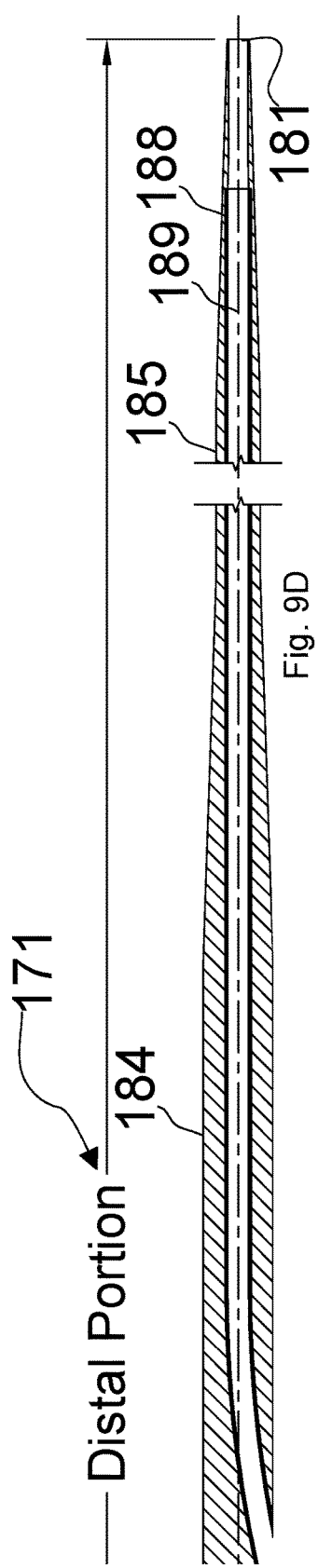
FIG. 9D is an enlarged detail view of FIG. 9A, showing a distal end of a distal portion of the adapter.
Figure 9E:
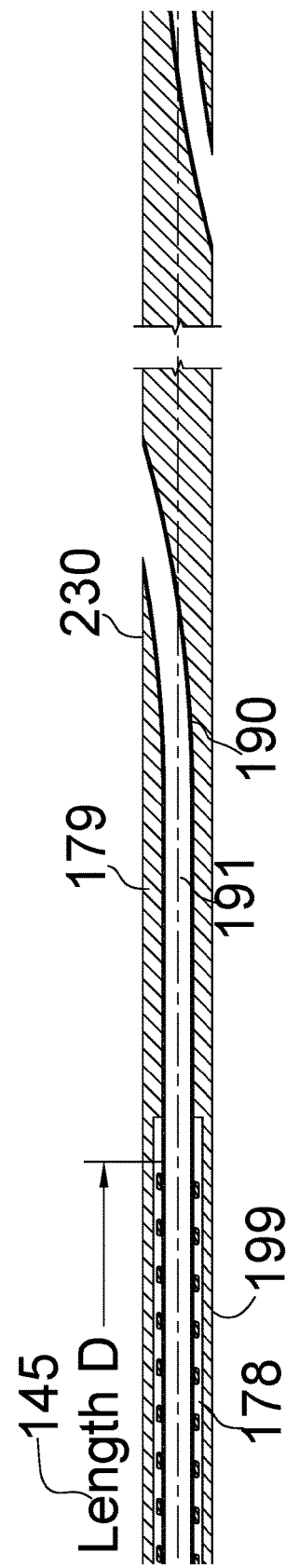
FIG. 9E is an enlarged detail view of FIG. 9A, showing a proximal end of a distal portion of the adapter.
Figure 9F:
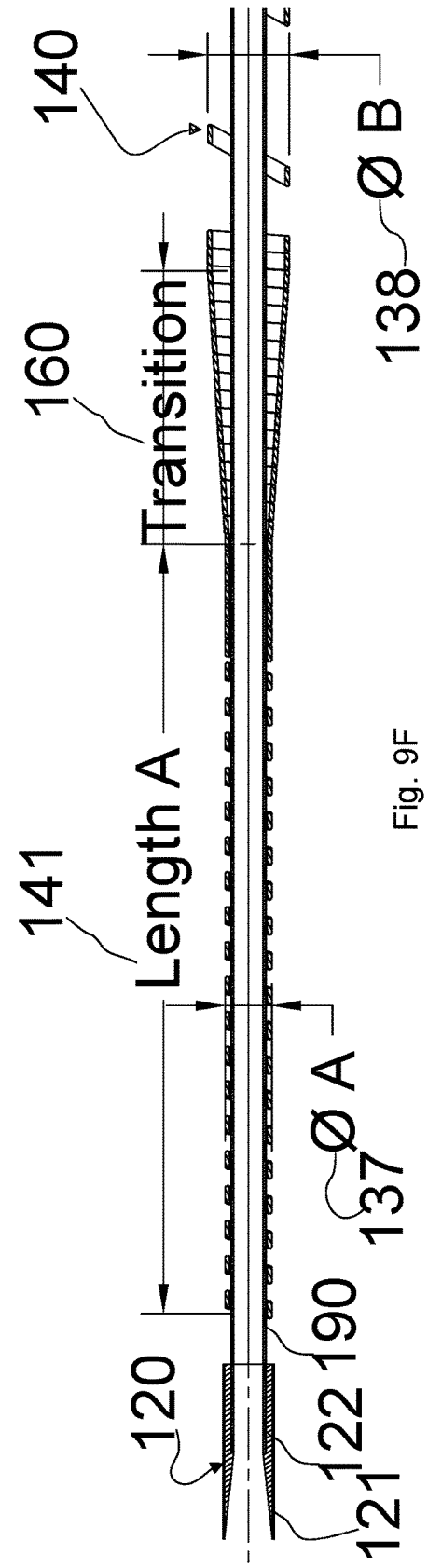
FIG. 9F is an enlarged detail view of FIG. 9A, showing a proximal end of a proximal portion of the adapter.
Figure 10F:
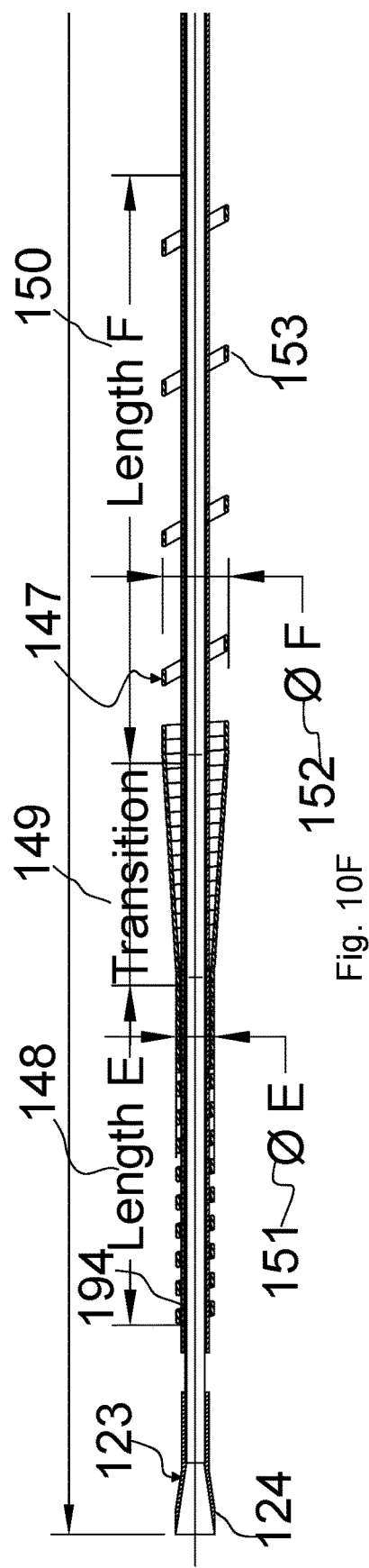
FIG. 10F is an enlarged detail view of FIG. 10A, showing the proximal coil element, coil located closer to the proximal end of the proximal portion of an adapter.
Figure 10G:
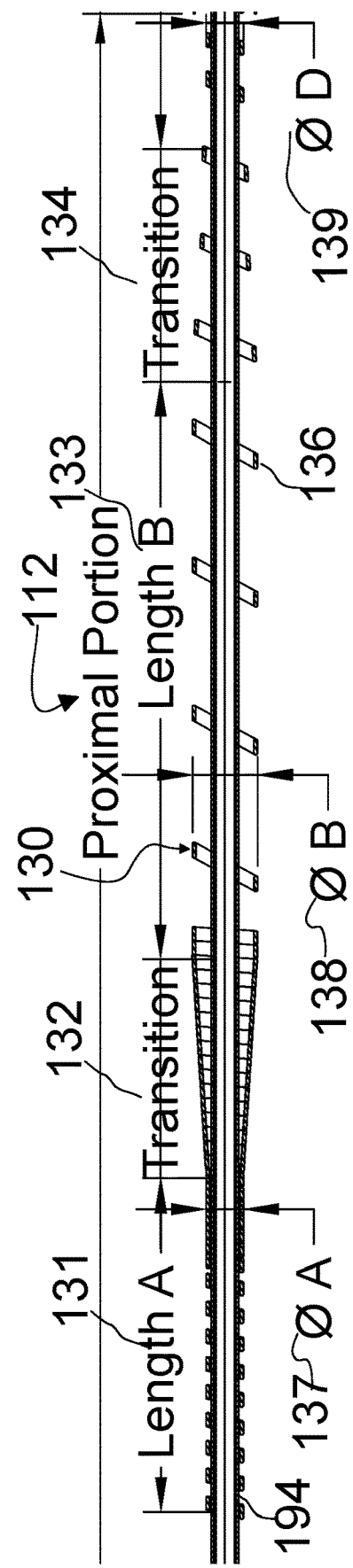
FIG. 10G is an enlarged detail view of FIG. 10A, showing the distal coil element, coil located closer to the distal end of the proximal portion of an adapter.

Reference will now be made in greater detail to preferred embodiments of the invention, examples of which is illustrated in the accompanying drawings. Wherever possible, the same reference numerals will be used throughout the drawings and the description to refer to the same or like parts.

FIG. 1A, FIG. 1B, and FIG. 1C illustrates one embodiment of adapter 10 coupled to distal end 213 of medical device 200. An example of a suitable medical device 200 is a catheter. Medical device 200 can be referred to as a parent. Adapter 10 includes distal portion 20 and proximal portion 30. Proximal portion 30 is predominately or entirely inside lumen 211 of target medical device 200. Distal portion 20 of adapter 10 is predominately outside of target medical device 200. Adapter 10 is co-axial with medical device 200 as shown by longitudinal axis 11. Proximal portion 30 of adapter 10 includes coil 12. Preferably coil 12 can be made of nitinol. Coil 12 can be comprised of wire with a cross-sectional size wound to form a general coil shape.

Coil 12 interfaces with lumen 211 of medical device 200 in a manner that secures adapter 10 to medical device 200. Adapter 10 can be secured to medical device 200 by an interference fit of coil 12 with lumen 211. Surface 220 of coil 12 can directly engage surface 212 of lumen 211. Coil 12 can have an austenitic finish temperature (Af) less than body temperature, such as an average of 37° C. of normal body temperature, and greater than a temperature typically expected in an operating room or catheter lab, for example about 25 degrees to about 30 degrees C. Coil 12 can be twisted and or elongated to reduce a size or diameter of coil 12 such that coil 12 has a smaller size or diameter than a size or diameter of lumen 211 to facilitate positioning adapter 10 inside medical device 200. As adapter 10 warms to body temperature during use in-vivo, coil 12 can expand to provide additional securement to medical device 200.

Alternatively, coil 12 can be designed to be physically restrained or constrained to have a size or diameter smaller than internal lumen 211 of medical device 200 in an operating room environment and coil 12 can expand to interface with the internal lumen 211 of the target catheter or device 200 when the physical restraint is removed, once the adapter 10 is seated within medical device 200. Coil 12 is shown with a constant round cross-section, alternatively the coil 12 can have a rectangular cross-section of a flat wire coil design. A flat wire design provides the benefit of a lower profile coil 12 but still provides sufficient securement through an interference fit with lumen 211. The cross-section can be variable along the length of coil 12. A variable cross-section coil 12 design provides the advantage of biased securement towards either one of the ends of adapter 10. Coil 12 can have variable flexibility and bending about longitudinal axis 11.

In one embodiment, coil 12 provides additional reinforcement of medical device 200 to improve the kink resistance. Adapter 10 includes tube 16, coupled to distal portion 20 of adapter 10 and is co-axial with coil 12. Tube 16 is an elongated element. Tube 16 has funnel portion 13 located at proximal end 30 of adapter 10. Funnel portion 13 can facilitate tracking of a guide wire from a proximal end (not shown) of medical device 200 to distal portion 20 of adapter 10. Tube 16 preferably is a polymer tube and can include braiding or other reinforcement. Coil 12 includes proximal end 15 that is coupled, bonded or otherwise attached near proximal end 19 of tube 16. Proximal end 15 of coil 12 can be retained to a size smaller than a size of lumen 211 to facilitate loading of adapter 10 into medical device 200 in use. Distal end 14 of coil 12 can be retained to a size smaller than a size of lumen 211. For example, proximal end 15 or distal end 14 can be heat shaped or formed to a smaller size than the size of lumen 211.

Distal end 14 provides a location on coil 12 that can be grabbed or held in order to twist and or elongate coil 12 to make it smaller in size to facilitate positioning the adapter 10 inside medical device 200. Distal portion 20 of adapter 10 is preferably made from a thermoplastic elastomer. Example thermoplastic elastomers or soft polymers include but are not limited to, polyether urethane and polyether block amide, such as for example ~40D PEBAX manufactured by Arkema.

In this embodiment, distal portion 20 is designed to modify medical device 200 that has a single guidewire access to have a two guidewire access. Distal portion 20 includes first lumen 21 for a first guidewire and second lumen 22. Second lumen 22 connects to lumen 211 of medical device 200 by way of tube 16 of adapter 10. This allows the user extra flexibility, for example to exchange guidewires, or to administer contrast or medications through the target catheter or device lumen 211. The path of a first guidewire is illustrated by first lumen centerline 23 and the path of a second guidewire is illustrated by the second lumen centerline 24. Accordingly, the path of lumen centerline 23 is outside of device 200.

Distal portion 20 includes reduced size portion 17 at proximal end 26 of distal portion 20 which is designed through choice of materials, for example thermoplastic elastomers or soft polymers, and of a geometry to interface with lumen 211 of medical device 200. A slight interference fit between reduced size portion 17 and lumen 211 provides a stable structure during introduction of the coupled adapter 10 and medical device 200 into a body cavity or vessel. Adapter 10 can include a tapered distal end 27 of distal portion 20 which facilitates tracking the medical device 200 with attached adapter 10 inside a body lumen.

FIG. 2 illustrates adapter 10 in a configuration where coil 12 has been reduced to a smaller size by elongating coil 12. FIG. 3 illustrates adapter 10 in a configuration where the coil 12 has been reduced to a smaller size by rotating or twisting coil 12. An alternate embodiment of adapter 10 is where a combination of coil 12 twisting and elongating reduces the size of coil 10 such that it can fit within medical device 200. Distance Ds2 between distal end 14 of coil 12 and proximal end 26 of distal portion 20 in FIG. 2 and FIG. 3 is smaller than distance Ds1 between distal end 14 of coil 12 and proximal end 26 of distal portion 20 as illustrated in FIG. 1C. In an alternate embodiment of adapter 10, if the user twists and or elongates coil 12 such that distal end 14 of coil 12 is within a predetermined distance of proximal end 26 of distal portion 20, then the user would know adapter 10 is safe to insert into medical device 200. For example, tube 16 can be marked to indicate the appropriate location of distal end 14 of coil 12.

FIG. 4 illustrates an alternate embodiment of the present invention shown as adapter 40. Adapter 40 has distal portion 41 and proximal portion 42 similar to distal portion 20 and proximal portion 30 of adapter 10 as shown in FIGS. 1A, 1B and 1C. Adapter 40 includes tube 16 with funnel portion 13 located at proximal portion 42 of adapter 40. Tube 16 is coupled to distal portion 41. Coil 12 is also coupled to distal portion 41 and interfaces with lumen 211 of medical device 200 in a manner that secures adapter 40 to medical device 200. Securement can be achieved in a similar manner as previously described for adapter 10.

FIG. 5 illustrates an alternate embodiment of the present invention shown as adapter 50. Adapter 50 has distal portion 51 and proximal portion 52 similar to distal portion 20 and proximal portion 30 of adapter 10 as shown in FIGS. 1A, 1B and 1C. Adapter 50 is similar to adapter 40, except portion 53 of coil 12 that interfaces with lumen 211 has a larger pitch than that of adapter 40. For example, the pitch can be in the range of about 2 to about 10 times the size of the coil-sectional size of the wire of coil 12. Adapter 50 also includes proximal end 25 of coil 12 which is similar to distal end 14 of adapter 10 in both use and form, except coil 12 is elongated and or twisted toward the proximal portion 52 of adapter 50 to make the size of coil 12 smaller to facilitate insertion of adapter 50 into medical device 200.

FIG. 6 illustrates an alternate embodiment of the present invention shown as adapter 60. Adapter 60 has distal portion 61 and proximal portion 62 similar to distal portion 20 and proximal portion 30 of adapter 10 as shown in FIGS. 1A, 1B and 1C, as well as other similar features. Proximal portion 62 includes coil 12 which has a reduced sized portion 18 such that it grips tube 16. Coil 12 can be heat shaped or formed with a portion that interfaces with lumen 211 of medical device 200. Reduced sized portion 18 has an inside diameter dia1 smaller than outside diameter dia2 of tube 16 to contact and grip tube 16 during use. Reduced diameter portion 18 of coil 12 can be bonded, glued, or heat reflowed to tube 16, for example, to further couple coil 12 to proximal portion 62.

FIG. 7 illustrates an adapter 70 in a configuration where coil 12 has been reduced to a smaller size by elongating and or twisting coil 12, similarly illustrated in FIG. 2 and FIG. 3. Adapter 70 has distal portion 71 and proximal portion 72 similar to distal portion 20 and proximal portion 30 of adapter 10 as shown in FIGS. 1A, 1B and 1C. Distal portion 71 includes single lumen tip 73, co-axial with longitudinal axis 11. Single lumen tip 73 has been reinforced with reinforcement section 74. For example, reinforcement section 74 can be a coil or braid. Reinforcement section 74 includes proximal coil portion 75 which extends past the proximal end of single lumen tip 73. Proximal coil portion 75 provides a slight interference fit with lumen 211 and a stable interface during initial insertion of adapter 70 into medical device 200 by the user. Reinforcement section 74 reinforces distal portion 71 and can facilitate tracking medical device 200 through a tight lesion.

FIG. 8A, FIG. 8B, FIG. 8C, FIG. 8D, FIG. 8E, and FIG. 8F illustrate an alternate embodiment of the present invention shown as adapter 100. Adapter 100 has distal portion 170 and proximal portion 110. Proximal portion 110 includes coil 130. Coil 130 is wound from wire 136 and has multiple diameters along its length. In one embodiment, wire 136 is flat with a rectangular or square cross-section. For example, coil 130 can have a wound length A 131 at a diameter øA 137 at proximal end of coil 130. The wound pitch of wire 136 along wound length A 131 is variable, not constant, and changes from a pitch that is approximately twice the width 162 of flat wire 136 at proximal end of the wound length A 131, to a pitch that is approximately equal to a width of flat wire 136, such that wire 136 is close wrapped at distal end of wound length A 131. A variable pitched wound length has advantages in that the farther spaced pitched coil can be more flexible, and the close wrapped coil can be stiffer and stronger in torsion or bending. A variable pitched wound length also has advantages in that the farther spaced pitched coil can also provide a better bonding geometry such that a bonding agent or adhesive can flow between wraps of coil 130. As wire 136 is wound distally to form coil 130, the diameter of the coil 130 transitions from a size øA 137 to a larger size øB 138 over length transition 132. Wire 136 is wound over length B 133 at a size øB 138. The wound pitch of wire 136 along wound length B 133 is variable, not constant, and changes from a pitch that is approximately equal to width 162 of wire 136, such that wire 136 is close wrapped, to a significantly wider pitch that is approximately more than 5 times the close wrapped pitch. A dramatic or rapid change in pitch from close wrapped to more than 5 times width 162 of flat wire 136 is advantageous because it creates a wedge when coil 130 is constrained within internal lumen 211 of medical device 200 during use and can improve the interference fit and retention properties of adapter 100 within medical device 200. Typically, øA 137 would be dimensionally smaller than lumen 211 of the target medical device 200 and øB 138 would be dimensionally larger than lumen 211 of the medical device 200. As wire 136 is wound distally to form coil 130 the diameter of coil 130 transitions from a size øB 138 to a smaller size øD 139 over length transition 134. The wound pitch of wire 136 along wound length transition 134 is approximately uniform.

In an alternate embodiment, the wound pitch of wire 136 along wound length transition 134 is variable. Wire 136 is wound distally from length transition 134 to continue to form coil 130 at a size øD 139 over a wound length D 135. Typically, øD 139 would be dimensionally smaller than lumen 211 of medical device 200. A portion of wound length D 135 of coil 130 at a size øD 139 is within cavities 178 and 177 of distal portion 170 of adapter 100. Cavity 177 is sized to interface with a distal end of medical device 200 and cavity 178 is sized to accommodate the coil 130 at a size øD 139. Cavity 178 is sized to allow wound length D 135 of coil 130 to move freely within cavity 178 when there is not an external mechanism gripping, pinching or clamping proximal end of distal portion 170 in the area of cavity 178. When there is an external mechanism gripping, pinching or clamping the proximal end of distal portion 170 in the area of cavity 178, cavity 178 is sized to prevent a portion of coil 130 in wound length D 135 from rotating or moving, holding coil 130, which has been previously rotated/twisted to a smaller size state to facilitate insertion of proximal portion 110 of adapter 100 into medical device 200.

Coil 130 can be made from Nitinol and have an austentic finish temperature (Af) approximately equal to or less than an ambient temperature of the operating room or catheter lab environment so coil 130 will expand when released from a smaller size state after insertion into medical device 200. Alternatively, coil 130 can be made from Nitinol and have an austenitic finish temperature (Af) less than body temperature but greater than the temperature typically expected in an operating room or catheter lab, for example about 25 C-30 C, except in zone T 161 where coil 130 has been selectively heat treated to have an austentic finish temperature (Af) approximately equal to or less than an ambient temperature operating room or catheter lab environment, for example less than about ~18 C, to enable zone T 161 of Nitinol coil 130 to expand when released from a smaller size state after insertion into medical device 200 in the catheter lab environment. Coil 130 having multi-zone or variable thermal properties has advantages in that it can be easier to insert adaptor 100 into medical device 200 with some of coil 130 having a higher Af temperature. The selectively heat treated portion of coil 130 in zone T 161 is biased to engage internal lumen 211 of medical device 200 more than the rest of coil 130 to facilitate creating the wedge, as described above, after coil 130 is released from a smaller size state and constrained within internal lumen 211 of medical device 200. As adapter 100 warms to body temperature during use in-vivo the zone T is 161 of coil 130 provides additional securement and structure to adapter 100. Zone T 161 as shown includes portion of length A 131, transition 132 and portion of length B 133. Alternatively, zone T 161 can include just a portion of transition 132 and a portion of length B 133 or other combinations.

Coil 130 is coupled to, bonded to or otherwise attached to central tube 182 of central lumen 183 of adapter 100 at part or all of the wound length A 131 at øA 137. Proximal end 120 of proximal portion 110 of adapter 100 includes inner element 122 and outer element 121. Inner element 122 and outer element 121 can form a funnel shape. Outer element 121 can be radiopaque or partially radiopaque to provide a landmark for proximal end 120 of adapter 100 when used in-vivo. The funnel shape of proximal end 120 of the adapter 100 can facilitate the back loading of a guidewire through the medical device 200 and adapter 100 during use. Proximal end 120 of adapter 100 is coupled, bonded or otherwise attached to the central tube 182. In one embodiment, central tube 182 can be unitary with inner element 122.

Central tube 182 connects proximal end of coil 130, in the area of Length A 131 and proximal end 120 to distal portion 170. Distal portion 170 of adapter 100 has an outer body 179 that is typically cylindrical or a revolved shape. Alternatively, outer body can have a non-revolved profile in portions or entirely. Outer body 179 can be made from a polymer. Outer body can be reinforced with metal, polymer or ceramic fibers, wire, laser cut hypotube and the like. Outer body 179 can be a laminated structure which can include multiple tube elements or materials. Outer body 179 can have a stepped tapered shape with first outside diameter 185 and second outside diameter 184 connected by tapered portions. Distal portion 170 has first exit lumen 186 of central lumen 183 and second exit lumen 187 of central lumen 183 at opposite each other in outer body 179. First exit lumen 186 is angled at angle A1 toward proximal portion 110 of adapter 100 from the central axis of central lumen 183. An angle in a direction of angle A1 can be advantageous when a guidewire is tracked through central lumen 183 starting at distal tip 181 of distal portion 170, exiting through first exit lumen 186. Second exit lumen 187 is angled at angle A2 toward distal end of adapter 100 from the central axis of central lumen 183. An angle in a direction of angle A2 can be advantageous when a guidewire is tracked through central lumen 183 at proximal end 120 of proximal portion 110, exiting through second exit lumen 187. Central tube 182 terminates proximal to distal tip 181 such that a portion of central lumen 183 is formed only by outer body 179. Alternatively, central tube 182 could extend to distal tip 181 or terminate at a more proximal location within outer body 179. Central tube 182 can form central lumen 183 for a majority of the length of distal portion 170 to add strength and rigidity if required, for example if central tube 182 was a braided or wire reinforced structure.

In one embodiment, coil 130 has been rotated or twisted about the longitudinal axis of coil 130 and central tube 182, while central tube 182 and a portion of wound length A 131 at øA 137 attached to central tube 182 are held fixed to decrease its size, specifically in transition 132, length B 133, and transition 134. After coil 130 has been rotated or twisted to decrease the size of transition 132, length B 133, and transition 134, a portion of distal end 198 of coil 130, length D 135, which is already at a small diameter, can be held and fixed relative to distal portion 170 and coupled central tube 182 such that the coil 130 will remain at a reduced diameter. When a portion of distal end 198 of coil 130, length D 135 that was held is released, coil 130 will expand back from the small size state to its unconstrained size state and this expansion will tend to happen starting at unattached distal end 197, length D 135 as coil 130 starts to expand/unwind from the distal end and progressively expands/unwinds moving proximal. In one embodiment, as coil 130 progressively expands/unwinds from distal end 197 to proximal end of coil 130, distal elements of coil 130 do not substantially inhibit the expansion and engagement of the portion transition 132 and Length B 133 to internal lumen 211 of medical device 200, to facilitate creating the wedge.

FIG. 9A, FIG. 9B, FIG. 9C, FIG. 9D, FIG. 9E, FIG. 9G and FIG. 9H illustrate an alternate embodiment of the present invention shown as adapter 101. Adapter 101 is similar to Adapter 100 and has distal portion 171 and proximal portion 111. Proximal portion 111 includes coil 140 which is similar to coil 130. Coil 140 is wound from wire 136 and has multiple diameters along the length of coil 140. Coil 140 as shown has a wound length A 141 at a diameter øA 137 at proximal end 157 of coil 140. The wound pitch of wire 136 along wound length A 141 is variable, not constant, and changes from a pitch that is approximately twice the width 162 of flat wire 136 at the proximal end of the wound length A 141, to a pitch that is approximately equal to the width 162 of wire 136, such that wire 136 is close wrapped at the distal end of wound length A 141. A variable pitched wound length has advantages that the farther spaced pitched coil can be more flexible, and the close wrapped coil can be stiffer and stronger in torsion or bending. A variable pitched wound length can have advantages in that the farther spaced pitched coil can also provide an improved bonding geometry such that a bonding agent or adhesive could flow between wraps of coil 140. As wire 136 is wound distally to form coil 140, the diameter of the coil 140 transitions from a size øA 137 to a larger size øB 138 over length transition 160. Wire 136 is wound over a length B 133 at a size øB 138. The wound pitch of wire 136 along wound length B 133 is variable, not constant, and changes from a pitch that is approximately equal to width 162 of wire 136, such that wire 136 is close wrapped, to a significantly wider pitch that is approximately more than 5 times width 162 of the flat wire 136. A dramatic or rapid change in pitch from close wrapped to more than 5 times the width 162 of wire 136 as shown is advantageous because it creates a wedge when coil 140 is constrained within internal lumen 211 of medical device 200 during use and can improve the interference fit and retention properties of adapter 101 within the catheter or device 200. Typically, øA 137 would be dimensionally smaller than lumen 211 of medical device 200 and øB 138 would be dimensionally larger than lumen 211 of the medical device 200. As wire 136 is wound distally to form coil 140 the diameter of coil 140 transitions from size øB 138 to a smaller size øC 144 over length transition 142, the wound pitch of wire 136 along wound length transition 142 is substantially uniform. Alternatively, wound pitch of wire 136 along wound length transition 142 is variable. Wire 136 is wound distally from length transition 142 to continue to form coil 140 at a size øC 144 over wound length C 143. øC 144 can be dimensionally similar to or slightly smaller than lumen 211 of medical device 200 so that as coil 140 was unconstrained from a small size state in use to secure adapter 101 to internal lumen 211, wound length C 143 of coil 140 at size øC 144 would be less likely to inhibit wound length B 133 of coil 140 at size øB 138 from engaging and securing coil 140 to internal lumen 211 of medical device 200. As wire 136 is wound distally to form coil 140 the diameter of coil 140 transitions from size øC 144 to a smaller size øD 139 over length transition 146, the wound pitch of wire 136 along wound length transition 146 is substantially uniform. Alternatively, wound pitch of wire 136 along wound length transition 146 is variable. Wire 136 is wound distally from length transition 146 to continue to form coil 140 at a size øD 139 over wound length D 145. Typically, øD 139 would be dimensionally smaller than lumen 211 of medical device 200. A portion of the wound length D 145 of coil 140 at a size øD 139 is within cavities 178 and 177 at proximal end 199 of distal portion 171 of adapter 101. Cavity 177 is sized to interface with distal end (not shown) of medical device 200 and cavity 178 is sized to accommodate coil 140 at a size øD 139.

Cavity 178 is sized to allow wound length D 145 of coil 140 to move freely within cavity 178 when there is not an external mechanism gripping, pinching or clamping proximal end 199 of distal portion 171 in the area of cavity 178. When there is an external mechanism gripping, pinching or clamping proximal end 199 of distal portion 170 in the area of cavity 178, cavity 178 sized to prevent a portion of coil 140 in wound length D 145 from rotating or moving, holding coil 140, which has been previously rotated/twisted to a smaller size state to facilitate insertion of proximal portion 111 of adapter 101 into medical device 200.

Coil 140 is coupled to, bonded to or otherwise attached to second tube element 190 forming a portion of second lumen 191 of adapter 101 at or along part or all of the wound length 141 at øA 137. It may be advantageous for wound length 141 to be attached to second tube element 190 predominately close to transition 160 such that an uncoupled portion of wound length 141 could extend proximally to add more structure and support to adapter 101 and medical device 200. Proximal end 120 of adapter 101 is attached to second tube element 190 in a similar manner as proximal end 120 of adapter 100 is attached to central tube 182.

Distal portion 171 of adapter 101 has outer body 179 that is typically cylindrical or a revolved shape. Alternatively, distal portion 171 of adapter 101 has outer body 179 that has a non-revolved profile in portions or throughout, similar to outer body 179 of adapter 100 shown in FIG. 8A. Second tube element 190 is attached or coupled to outer body 179, thereby connecting proximal end of coil 140 in the area of Length A 141 and proximal end 120 to distal portion 171. Distal portion 171 has first tube element 188 which forms a portion of first lumen 189. As shown, first tube element 188 terminates proximal to distal tip 181 such that a portion of first lumen 189 is formed only by the outer body 179. First tube element 188 could extend to distal tip 181 or terminate at a more proximal location within outer body 179. Second lumen 191 and first lumen 189 exit outer body 179 in a manner similar to second exit lumen 187 and first exit lumen 186. Second tube element 190 and first tube element 188 are shown extending to edge 230 of outer body 179 of distal portion 171. Alternatively, second tube element 190 and first tube element 188 can terminate before edge 230 and such that a portion of second lumen 191 and first lumen 189 can be formed by outer body 179 of distal portion 171.

FIG. 10A, FIG. 10B, FIG. 10C, FIG. 10D, FIG. 10E, FIG. 10F and FIG. 10G illustrate an alternate embodiment of the present invention, adapter 102. Adapter 102 is similar to adapter 100 and has distal portion 172 and proximal portion 112. Proximal portion 112 includes coil 130 located closer to distal portion 172 and coil 147 located closer to proximal end 123. Coil 130 is a left handed helix and coil 147 is a right handed helix. Coil 130 has been described as part of adapter 100. Coil 147 is similar to coil 130. Coil 147 is wound from wire 153 and has multiple diameters along the length of the coil 147. Wire 153 can be a flat wire. Coil 147 as shown has a wound length E 148 at a diameter (ø) øE 151 at the proximal end of coil 147. As wire 153 is wound distally to form coil 147 the diameter of coil 147 transitions from a size øE 151 to a larger size øF 152 over a length transition 149. Wire 153 is wound over a length F 150 at a size øF 152. The wound pitch of 153 along wound length F 150 is variable, not constant, and changes from a pitch that is approximately equal to the width of wire 153, such that wire 153 is close wrapped, to a significantly wider pitch that is approximately more than 5 times the width of wire 153. A dramatic or rapid change in pitch from close wrapped to more than 5 times the width of wire 153 is advantageous because it creates a wedge when coil 147 is constrained within internal lumen 211 of medical device 200 during use and can improve the interference fit and retention properties of adapter 102 within medical device 200. Typically, øE 151 would be dimensionally smaller than lumen 211 of medical device 200 and the øF 152 would be dimensionally larger than lumen 211 of medical device 200.

Adapter 102 includes coaxial tube elements, central tube 192 and reinforcing tube member 194. Central tube 192 forms a portion of central lumen 193 of adapter 102. Proximal end 123 of adapter 102 is attached or coupled to the central tube 192. Proximal end 123 is comprised of funnel element 124. Central tube 192 and funnel element 124 can be unitary such that funnel element 124 is a flared end of central tube 192. Funnel element 124 is advantageous in that it can facilitate back loading a guide wire through the medical device 200 and adapter 102. Central tube 192 and reinforcing tube member 194 are both attached, bonded or coupled to distal portion 172 of adapter 102. As shown, reinforcing tube member 194 terminates proximally to central tube 192 which terminates proximal to distal end 181 of proximal portion 172 of adapter 102. An alternate embodiment or configuration can have reinforcing tube member 194 attached to distal portion 172 and central tube 192 attached to reinforcing tube member 194 to form adapter 102. This embodiment has advantages if reinforcing tube member 194 were to terminate closer to distal tip 181 to include features to optimize the tip performance, for example as a crossing support device, while central tube 192 predominately provides a more optimized central lumen 193 for a guide wire as an example. In this embodiment, reinforcing tube member 194 and central tube 192 can terminate approximately together or central tube 192 can be more proximal than reinforcing tube member 194.

Coil 147 is attached, bonded or otherwise coupled to the reinforcing tube member 194 at all or a portion of length E 148. This could be accomplished using an adhesive to attach a portion of length E 148 to reinforcing tube member 194. In a similar manner as previously described, a portion or all of the length A 131 of coil 130 is bonded or attached to reinforcing tube member 194. The inside diameter of coil 130 at a size of øD 139 is typically larger than the outside diameter of second tube element 190 or central tube 182 or reinforcing tube member 194.

FIG. 11A, FIG. 11B, FIG. 11C, and FIG. 11D, illustrate adapter 102 while coil 130 has been rotated or twisted in a manner that wraps or winds it down to a smaller diameter øB 155. Coil 130 has been rotated or twisted such that transition 132, wound length B 133 and transition 134 have been made to be held in a state at a smaller diameter øB 155 over a combined wound length of transitions 132 and length B 154. Diameter øB 155 is approximately equal to or smaller than internal lumen 211 of medical device 200 to facilitate inserting adapter 102. Temporary constraining element 195 is positioned around this portion of coil 130 to secure coil 130 at smaller diameter øB 155. Temporary constraining element 195 is advantageous to allow coil 130 to be held in smaller diameter øB 155 without the need to hold or restrain from moving length D 135 section of coil 130. Length D 135 is not attached or coupled to reinforcing tube member 194.

FIG. 11A, FIG. 11B, FIG. 11C, and FIG. 11D show clamping element 196 pinching or holding a portion of Length D 135 from rotating such that temporary constraining element 195 can be removed and coil 130 would still be held in a state that includes smaller diameter øB 155. It may be advantageous to include a temporary constraining element 195 such that only temporary constraining element 195 holds coil 130 in a state at a smaller diameter øB 155 in an adapter packaging suitable for terminal sterilization and or shipping, transportation and inventory at the customer site, which would minimize the amount of time the load at the attached portion of coil 130 in Length A 131 would need to be reacted. When the adapter is ready to be used in an operating room or catheter lab, clamping element 196 can be applied and temporary constraining element 195 can be removed to allow insertion into medical device 200.

FIG. 12A, FIG. 12B, FIG. 12C, and FIG. 12D, illustrate adapter 102 after it has been initially inserted into medical device 200 while coil 130 has been rotated or wound down to a smaller diameter øB 155 and held in that position by clamping element 196. Coil 147 is shown after it has been inserted in internal lumen 211 of medical device 200. As coil 147 is inserted the portion of length F 150 and transition 149 as shown in FIG. 11A, FIG. 11B, FIG. 11C, and FIG. 11D conforms to the size of inner lumen 211 of medical device 200 and becomes a smaller diameter ø″ 159 by elongating and or rotating. Similarly to as described previously, a dramatic or rapid increase in pitch from close wrapped to more than 5 times the close wrap pitch, which is approximately the width of wire 153, as shown, is advantageous because it creates a wedge with an angle A 127, equal to or greater than approximately 15 degrees, when coil 147 is constrained within internal lumen 211 of medical device 200 during use, and can improve the interference fit and retention properties of adapter 100 within medical device 200. In the embodiment of adapter 102, coil 147 is the leading coil inserted into internal lumen 211 of medical device 200. As coil 147 is inserted into internal lumen 211, the wraps of wire 153 that are at a size approximately equal to internal lumen 211, located within transition 149 and length F 150, engage surface 212 of internal lumen 211 and reduce in size by elongating and rotating (predominately elongating) such that the transition and length F 158 is longer than the combination of transition 149 and length F 150, and the entire coil 147 can be inserted into medical device 200. This mode of action is different than that of coil 130.

As shown in FIG. 13A, FIG. 13B, FIG. 13C, and FIG. 13D, after adapter 102 is inserted into target device or catheter 200 and clamping element 196 is removed, coil 130 will rotate and expand to the size of internal lumen 211 to engage surface 212 of internal lumen 211 over a combined wound length of length B 156, which includes portions of transition 132, length B 133, and transition 134. Coil 130 is designed such that, upon expansion to conform to internal lumen 211 as described, within coil 130 geometry there is a dramatic or rapid increase in pitch from close wrapped to more than 5 times the close wrap pitch, which is approximately the width of wire 136, and which creates a wedge with an angle B 163 equal to or greater than approximately 15 degrees. An advantage to the mode of action of coil 130 versus the mode of action of coil 147 is that by predominantly rotating coil 130 to conform to the internal lumen 211 instead of predominately elongating coil 147 to conform to the internal lumen 211, coil 130 will be less likely to have axial re-coil when allowed to expand, and the force to insert adapter is removed. Coil 147 can be pulled into the lumen 211 of medical device 200 as adapter 102 is inserted into medical device 200 via the bonded connection in Length A 131 to reinforcing tube member 194. After adapter 102 has been inserted into medical device 200, coil 147 will tend to axially re-coil toward distal end of adapter 102, whereas coil 130 rotates into position without an external pulling force. Including both modes of action in one adapter is advantageous because it provides redundancy in case one mode is less effective than the other in retaining adapter 102 in medical device 200. Additionally, coil 130 and coil 147 are wound in opposite directions such that if adapter 102 is placed under an external torsional load, adapter 102 optimally reacts in either direction of an external torsional load.

FIG. 14A, FIG. 14B, and FIG. 14C illustrate adapter 103 after it has been inserted into medical device 200, and coil 130 has been deployed to engage internal lumen 211 securing adapter 103. Adapter 103 includes distal portion 173 and proximal portion 113 very similar to the previously described proximal portion 110 and proximal portion 111. Distal portion 173 of adapter 103 has outer body 179 that is typically cylindrical or a revolved shape. Alternatively, distal portion 173 of adapter 103 can have a non-revolved profile in portions or throughout. Outer body 179 has a stepped tapered shape with first outside profile 185, second outside profile 184 and third outside profile 180 connected by tapered portions. Distal portion 173 has first tube element 188 which forms a portion of first lumen 189. First tube element 188 terminates proximal to distal tip 181 such that a portion of first lumen 189 is formed only by outer body 179. First tube element 188 could extend to distal tip 181 or terminate at a more proximal location within outer body 179. Second tube element 190, which forms a portion of second lumen 191, connects coil element 130 of proximal portion 113 to distal portion 173. Second lumen 191 and first lumen 189 exit outer body 179 in a manner similar to second exit lumen 187 and first exit lumen 186. Second tube element 190 and first tube element 188 are shown partially extending to edge 230 of outer body 179 of distal portion 173 where a portion of second tube element 190 and first tube element 188 terminate before 230 edge of outer body 179, such that a portion of second lumen 191 and first lumen 189 are formed by outer body 179 of distal portion 173. Third outside profile 180 of outer body 179 includes first cavity 166 and second cavity 169, as shown in longitudinal cross section and transverse cross section Z-Z. First cavity 166 and second cavity 169 are shown as open cavities. Alternatively, first cavity 166 and second cavity 169 can be a closed cavity, such as a circle shaped cavity. First cavity 166 and second cavity 169 are shown to be 180 degrees opposite each other. Alternatively, first cavity 166 and second cavity 169 can have alternative orientations.

FIG. 15A, FIG. 15B, and FIG. 15C illustrate adapter 103, as shown in FIG. 14A, FIG. 14B, and FIG. 14C with the addition of first wire 167 and second wire 168. Preferably, first wire 167 originates with a first end outside the patient (not shown) and extends distally along the outside of medical device 200, then through first cavity 166 and first lumen 189, exiting distal end 181 of distal portion 173 and extends to second end 231 of first wire 167. Preferably, second wire 168 originates with a first end outside the patient (not shown) and extends distally through proximal end (not shown) of medical device 200 and continues inside lumen 211 of medical device 200, through second lumen 191 then wrapping to extend back proximally through second cavity 169 extending proximally along the outside of medical device 200, and extends to second end (not shown) of second wire 168. Second end (not shown) of second wire 168 can terminate outside the patient body. Adapter 103 can be advantageous when medical device 200 is a percutaneous transluminal angioplasty balloon, for example. First wire 167 can act a guide wire to track medical device 200 which is a percutaneous transluminal angioplasty balloon to the site of an arterial lesion or blockage as well as provide a mechanism to induce a stress concentration into the wall of the artery and lesion, preferentially dissecting or disrupting the lesion to improve dilation performance of the balloon at the target lesion. Second end of second wire 168 can extend proximally past the balloon in medical device 200 such that second wire 168 also provides a mechanism to induce a stress concentration similar to first wire 167. Second wire 168 can have curve 164. For example, second wire 168 can be manufactured from Nitinol and be heat treated to set a shape with curve 164. Alternately, second wire 168 can be designed to be readily shaped to curve 164. For example, second wire 168 can be manufactured from Nitinol and be heat treated to have an Af temperature such that second wire 168 is easily bent to curve 164 and stays in that shape during use, for example at an Af temperature above body temperature (37 C). Second wire 168 can be positioned into adapter 103 and medical device 200 of a balloon prior to introduction of adapter 103 and medical device 200 into the patient. After the ballooning procedure is completed, second wire 168 can be withdrawn from proximal end (not shown) of medical device 200. Alternatively, second wire 168 is tracked through medical device 200 and positioned in-vivo.

Figure 16A:
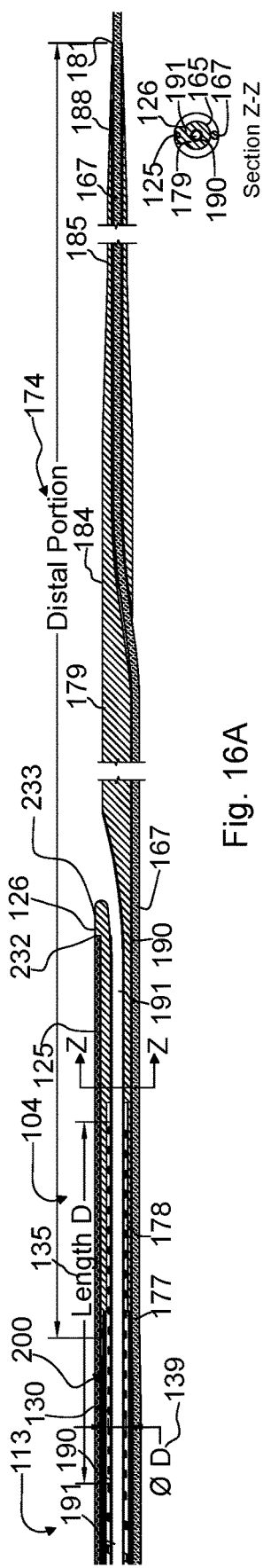
FIG. 16A is a partial schematic, longitudinal, cross-sectional view of an adapter according to an embodiment of the present invention and a partial schematic, longitudinal, cross-sectional view of a distal end of a medical device, where a coil element of the adapter has been rotated or twisted in order to reduce the size of the coil prior to insertion into the medical device then subsequently released to expand to an inner lumen of the medical device, which also includes a first and second wire, and a transverse cross-sectional view Z-Z of a distal portion of the adapter. Break line symbols are utilized to reduce the size of the schematic for clarity.
Figure 16B:
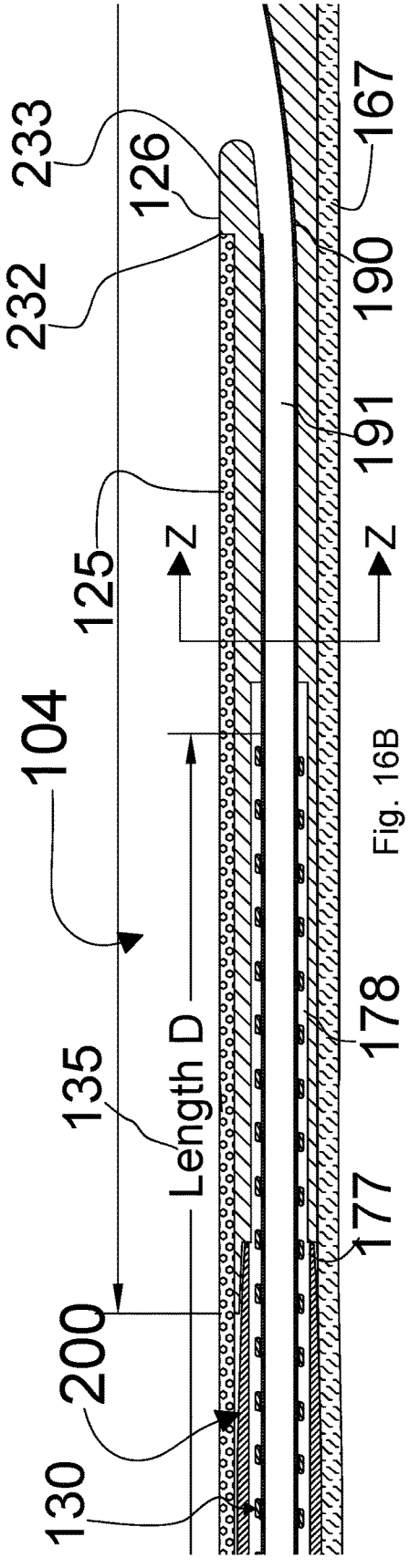
FIG. 16B is an enlarged detail view of FIG. 16A, showing a proximal end of a distal portion of the adapter.
Figure 16C:
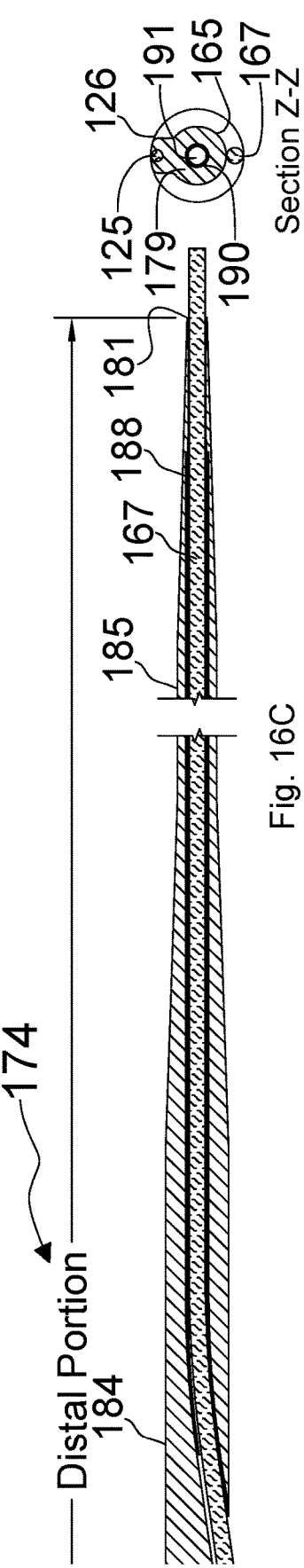
FIG. 16C is an enlarged detail view of FIG. 16A, showing a distal end of a distal portion of the adapter and a transverse cross-sectional view Z-Z of a distal portion of the adapter.

FIG. 16A, FIG. 16B, and FIG. 16C, illustrate adapter 104 which is similar to adapter 103. Adapter 104 includes distal portion 174 which includes third outside profile 126 of outer body 179. Second wire 125 includes first end 232 which is coupled or attached to outer body 179 at top or edge 233 of third outside profile 126. Second wire 125 extends proximally from outer body 179 and distal portion 174 along the outside of medical device 200 and extends to second end (not shown) of second wire 125. Second end (not shown) of second wire 125 can terminate within the artery or body vessel in a loop or fold to minimize any chance of incidental vessel trauma, or extend all the way proximally exiting the patient. As shown in transverse cross section view Z-Z of third outside profile 126, there is no cavity in third outside portion 126 for first wire 167. First wire 167 alternatively extends distally alongside third outside profile 126.

The size of first outside profile 185, second outside profile 184, and third outside portion 126 generally increase in size from first outside profile 185 to third outside profile 126. However, third outside profile 126 has a reduced size portion 165 which is approximately equal in size to second outside profile 184. This can be advantageous in that there would be room for second wire 125 to fold back and extend distally as medical device 200 and adapter 104 is withdrawn from the artery and patient.

FIG. 17A, FIG. 17B, and FIG. 17C illustrate adapter 105 which is similar to adapter 101. Adapter 105 includes distal portion 175. Distal portion 175 has outer body 179 that is typically made from a soft polymer or elastomeric polymer. Distal portion 175 incorporates first tube element 188 that forms a portion of first lumen 189 in outer body 179. First lumen 189 exits outer body 179 distally at distal tip 181. First lumen 189 is formed partially by first tube element 188 and outer body 179. First lumen 189 exits outer body 179 proximally at exit 253 which is proximal to distal exit 254 of second lumen 191 from outer body 179. Second lumen 191 is formed partially by second tube element 190 and outer body 179. As shown in section Y-Y, second lumen 191 transitions from a closed section as it exits outer body 179. Tube element 188 and tube element 190 are side by side and overlap for length 251 within outer body 179. First lumens 189 and second lumen 191 overlap for length 255. An alternate embodiment of distal portion 175 includes first lumen 189 formed entirely by outer body 179 without tube element 188. Distal portion 179 also includes a hole or passage 252 into cavity 178 close to distal end 234 of cavity 178. Hole 252 can be beneficial to facilitate flushing air out of cavity 178 prior to use. Hole 252 can also provide an additional conduit to deliver fluids or contrast through lumen 211 of medical device 200.

FIG. 18A, FIG. 18B, FIG. 18C, FIG. 18D, FIG. 18E, and FIG. 18F illustrate alternate embodiments of coil 257 of proximal portion 113 of an adapter 105 of the present invention. Coil 257 has a variable diameter and pitch. Similar to the other coil embodiments, coil 257 has a proximal diameter (ø) øE 151 and a larger diameter (ø) øF 152 at distal end 270 of coil 257. Coil 257 transitions in diameter from øE 151 to øF 152. Coil 257 is bonded or otherwise attached to central tube 263 that forms a portion of a central lumen 271 similar to central tube 182 over a length G 258. The unbonded distal portion, Length H1 272, of coil 257 includes a portion at a diameter øE 151, a portion at diameter øF 152 and a portion where the diameter transitions between those two diameters. The unbonded distal portion, Length H1 272, of coil 257 is shown with a variable pitch that are not close wrapped, but could include close wrapped pitch. A close wrapped pitch in the unbonded distal portion 272 at the smaller diameter and in the transition to the larger diameter can be advantageous as there can be less axial movement of central tube 263 under an axial load after the adapter 105 is attached to a target medical device 200. FIG. 18B illustrates coil 257 of proximal portion 113 of an adapter 105 after adapter 105 has been inserted and seated into medical device 200 with lumen 211 as previously described. As coil 257 is inserted, the unbonded distal portion elongates to a length H2 259, such that a portion of coil 257 forms an angle A 127 as previously described. Proximal portion 113 also includes proximal end 120 and is comprised of inner element 122 that forms a funnel and outer element 256. Outer element 256 is similar to outer element 121 and could be radiopaque or partially radiopaque to provide a landmark for the proximal end of the adapter in-vivo, but is shorter and doesn't fully cover inner element 122, and is longitudinally shorter in length than inner element 122.

FIG. 18C shows an embodiment of proximal portion 113 and coil 257 such that after inserting and seating into a target device 200 as described and the central tube 263 is placed under an axial load F 261, the unbonded distal portion, Length H3 260, of coil 257 becomes shorter than the length H2 259 prior to the axial load F 261. Additionally, a portion of the unbonded coil wraps that formed unbonded distal portion length H2 compress together axially under the axial load F 261 and touch each other, effectively completing the wedge formed by angle A 127, as illustrated in the enlarged detail view FIG. 18E.

FIG. 18D shows yet another embodiment of the proximal portion 113 and coil 257 such that after inserting and seating into medical device 200 as described and the central tube 263 is placed under an axial load F 261, the unbonded distal portion, Length H4 262, of coil 257 becomes shorter than the length H2 259 prior to the axial load F 261. Additionally, a portion of the unbonded coil wraps that formed unbonded distal portion length H2 259 compress together axially under the axial load F 261 and touch each other as well as nest inside or invaginate, effectively completing the wedge formed by angle A 127, as illustrated in the enlarged detail view FIG. 18F. Nested coil wraps as illustrated in FIG. 18D and FIG. 18F may be advantageous as it may increase the securement of the adapter.

It could be envisioned that multiple coils similar to coil 257 could be bonded to a central tube 263 in series to create proximal portion 113. Proximal portion 113 of this design can increase the robustness of the securement of the adapter to medical device 200. A multiple coil configuration of this nature can include both left and right hand coils as previously described to minimize a bias or potential securement issue when central tube 263 is place under a torsional load.

FIG. 19 illustrates an embodiment of proximal portion 114 of an adapter that includes a coil 264 similar to coil 257. Coil 264 includes all the elements of coil 257 plus a section of unbonded length J 265 that transitions from a larger diameter øF 152 to a smaller diameter that is preferentially smaller than the diameter of the inner lumen 211 of medical device 200, similar to a diameter øE 151. A coil design of this nature can be advantageous as it allows proximal portion 114 to be removed from medical device 200. Proximal portion 114 can be removed by a user gripping a coil wrap in length J 265 and pulling distally elongating and or rotating coil 264, releasing the wedge securement at the inside diameter of lumen 211 of target device 200. For example, if a proximal portion 114 were coupled to a distal portion similar to 102 to form an adapter, and a portion of length J 265 of coil 264 extended into cavity 178 after proximal portion 114 were inserted and seated into medical device 200, similar to length D 135 as shown in FIG. 13D, effectively extending out the distal end 213 of medical device 200, the user could cut distal portion 102 at a point along cavity 178, effectively separating distal portion 102 from proximal portion 114 such that the user can grip and pull distally a coil wrap in length J 265, removing proximal portion 114 from medical device 200. It is understood that a length of wire 153 or an extension of wire 153 extending out of medical device 200 is gripped to remove proximal portion 114.

FIG. 20A and FIG. 20B show proximal portion 115 with coil 266 that is similar to coil 130. Coil 266 includes a transition 267 that varies in diameter and pitch. Coil 266 also includes a length K 268 at a diameter øB 138 that is predominately a wider spaced pitch and a variable pitch transition to a diameter øD 139. A design similar to this may have an advantage in securement when inserted into medical device 200 as described for coil 130. It is understood that coils constructed similar to coil 130 and coil 266 can alternatively be inserted into medical device 200, similarly to coil 257, and still provide securement after insertion.

FIG. 21A and FIG. 21B illustrate an alternate embodiment of a distal portion 176 of adapter 106. Adapter 106 includes distal portion 176. Adapter 106 has been inserted into medical device 200. Distal portion 176 includes first lumen 273, outer body 179, and second tube element 190 forming a portion of second lumen 191 of adapter 106. First lumen 273 exits outer body 179 proximally at exit 253 which is proximal to distal exit 254 of second lumen 191 from outer body 179. Outer body 179 includes taper portion 274 to proximally interface and engage with surface 212 of distal inner lumen 211 of medical device 200. Taper portion 274 interfaces and engages with medical device 200 and can reduce the overall size or profile of adapter 106. Distal portion 176 includes reinforcing coil 275 which spans transition portion 276 between medical device 200 and distal portion 176. Reinforcing coil 275 can reduce the chance of the medical device 200 or adapter 106 kinking at or near transition 276. Reinforcing coil 275 is smaller in size or diameter than inner lumen 211 and is partially attached to outer body 179 and distal portion 176. Distal portion 176 also includes distal tip 181. When attached to a medical device 200, the first lumen 273 can be used as a guide for a first guidewire, while the second lumen 191 can be used to introduce a second guidewire or other accessory into the patient. For example, an accessory with drill bit like features or characteristics that could be used to penetrate the cap of a completely occluded lesion may be advantageous.

Figure 22A:
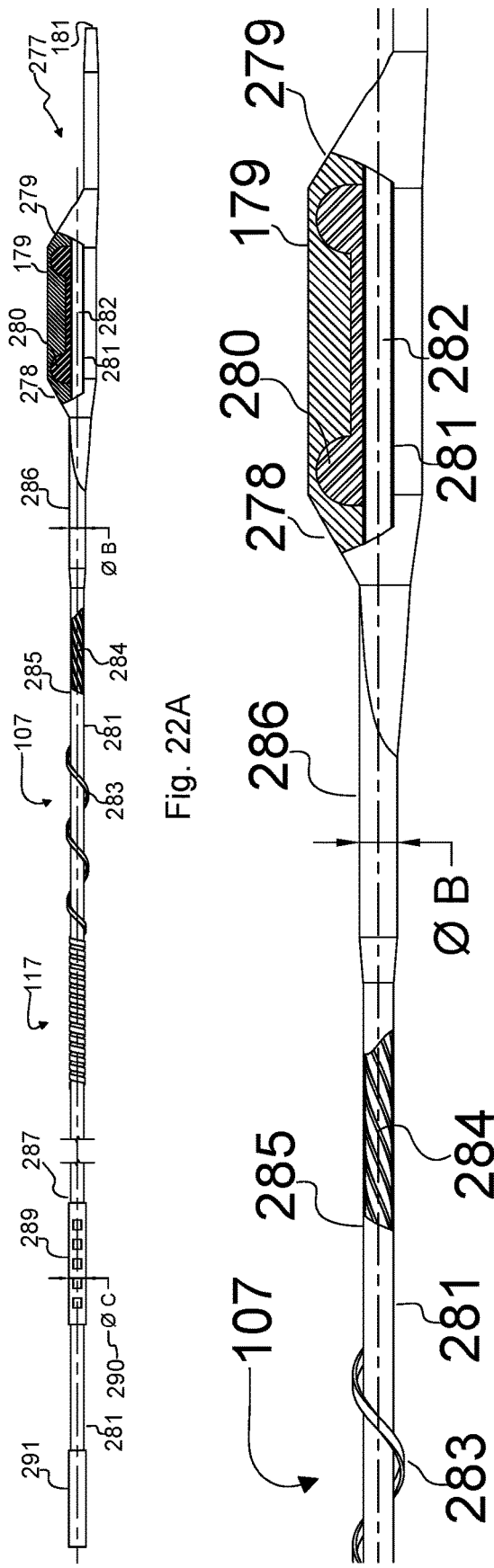
FIG. 22A is a schematic, longitudinal, view of an adapter according to an embodiment of the invention, and includes a schematic representation of a partial portion where the conductors embedded inside the central lumen wall are exposed, and a partial cross-section of the distal portion of the adapter showing the camera module. Break line symbols are utilized to reduce the size of the drawing for clarity
Figure 22B:
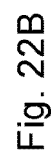
FIG. 22B is an enlarged detail view of a portion of FIG. 22A.
Figure 22C:
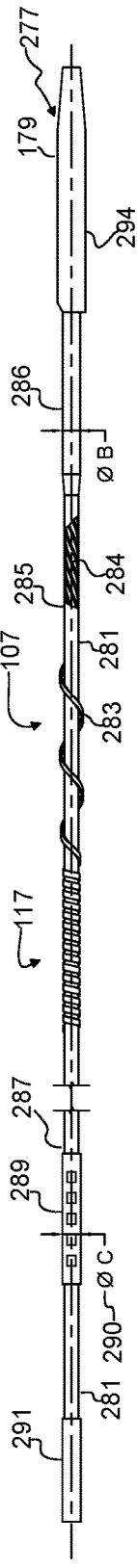
FIG. 22C is a schematic, longitudinal, view of an adapter according to an embodiment of the invention and includes a schematic representation of a partial portion where the conductors embedded inside the central lumen wall are exposed, and a schematic representation of a distal portion of the adapter including an electrically active element. Break line symbols are utilized to reduce the size of the drawing for clarity.
Figure 23:
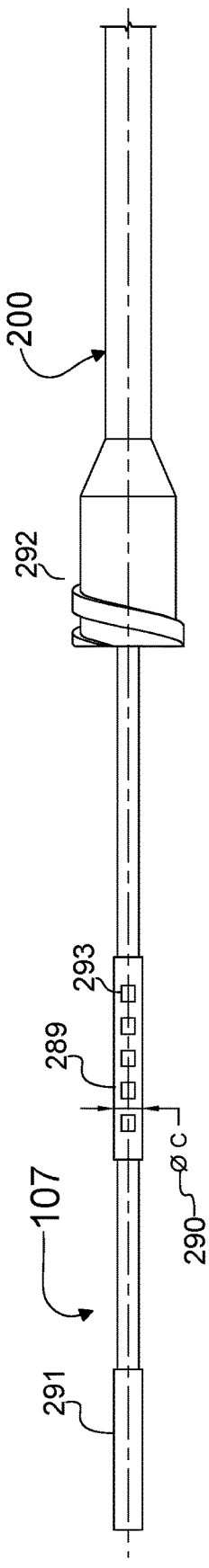
FIG. 23 is a partial schematic, longitudinal, view of a proximal end of an adapter according to an embodiment of the invention, where the adapter has been inserted into a target medical device.

FIG. 22A, FIG. 22B, FIG. 22C, and FIG. 23 illustrate adapter 107. Adapter 107 includes distal portion 277, which is similar to distal portion 176 as shown in FIG. 21A, but includes an embedded or incorporated camera module 280 in outer body 179 and a proximal portion 117. Outer body 179 is typically made from a polymer or elastomeric polymer. Outer body 179 includes a portion with a diameter øB 286 that is less than the diameter of inner lumen 211 such that a portion of the outer body 179 can fit within inner lumen 211. Adapter 107 includes central tube 281 that forms central lumen 282, similar to tube 190 and lumen 191 shown in FIG. 21A. Central tube 281 connects distal portion 277 and proximal portion 117 of adapter 107. Proximal portion 117 is similar to the previously described proximal portions and includes a coil 283, similar to coil 257 previously described with reference to FIG. 18A. Central tube 281 includes one or more conductors 284 embedded in wall 285 of central tube 281, for illustration purposes a portion of central tube 281 is shown with the conductors exposed. For example, conductors 284 could be embedded in Polyimide or Polyimide and PEBAX to form central tube 281. Conductors 284 can also run longitudinal along the X axis of central tube 281 instead of spiraling as shown. In one embodiment six (6) conductors are shown embedded in wall 285 of central tube 281 and spiral around the x axis of central tube 281 connecting camera module 280 to connector 289 near proximal end 287 of central tube 281. It will be appreciated that the numbers of conductors can include those required to supply power to camera module 280 and send signals from camera module 280 and could be more or less than six. As illustrated in FIG. 23, proximal end 287 of central tube 281 and adapter 107 extend out proximal end 292 of target medical device 200. It is common for a proximal end of a medical device to terminate with a luer fitting. As shown, connector 289 has six (6) pads 293 that individually connect to six (6) conductors 284 that spiral along central tube 281. Connector 289 can be designed such that a cable (not shown) with the appropriate mating connectors can couple camera module 280 to an appropriate viewing device or device that can interpret the electrical signals and interface with camera module 280. The diameter øC 290 of connector 289 must be smaller than the lumen of the target medical device 200. Also shown is proximal end 291 of adapter 107. Proximal end 291 is designed to potentially interface with a syringe for flushing of liquids through the central lumen 282 and allow access of guidewires or other devices and equipment through the central lumen 282 as shown in FIGS. 22A and 22B. Camera module 280 incorporates elements that allow visualization both distally through distal viewing port 279 and in the proximal direction through proximal viewing port 278. In a similar manner as the described with regard to camera module 280 and adapter 107, electrically activated element 294 could be embedded, incorporated or attached to distal portion 277 of adapter 107. Electrically activated elements can be, for example, sensors or transducers. Connector 289 and conductors 284 electrically connect distal portion 277 of adapter 107 to the outside of the patient, proximal to the medical device, or parent 200. For example, electrically activated element 294 can be one or more electrically activated elements including a sensor or transducer. For example, electrically activated element 294 can be an Intra-Vascular UltraSound (IVUS) sensor/transducer, Optical Coherence Tomography (OCT) sensor/transducer, pressure transducer, flow transducer, or other imaging or sensor technology could be attached and electrically coupled to a suitable interface device as described.

FIGS. 24, 25A, 25B, 25C, and 25D illustrate adapter 108. Adapter 108 includes distal portion 310 and proximal portion 118. Adapter 108 includes central tube 315 that is co-axial with inside tube 322 where inside tube 322 forms central lumen 326 as shown in FIG. 25B, similar to tube 190 and lumen 191 as shown in FIG. 21A. Referring to FIG. 24, central tube 315 connects distal portion 310 and proximal portion 118 of adapter 108. Proximal portion 118 is similar to the previously described proximal portions and includes coil 313, similar to coils previously described, bonded, coupled or otherwise attached to central tube 315. Distal portion 310 of adapter 108 includes balloon assembly 311. Balloon assembly 311 includes balloon 312 coupled to central tube 315 and inside tube 322 through polymer body 316 at proximal end 320 of balloon 312 and polymer tip 330 at distal end 181 of adapter 108. Polymer body 316 extends proximally from balloon 312 and includes channel 317 that runs longitudinally along the length of polymer body 316. Polymer body 316, balloon 312, and central tube 315 are coupled, bonded or otherwise attached together to create sealed balloon assembly 311 at proximal end 320. Distal end 339 of balloon 312 is similarly coupled, bonded or otherwise attached to inside tube 322 through distal tip 330. In this embodiment, central tube 315 terminates proximally to inside tube 322, and end 337 of central tube 315 can be plugged by seal element 329. Seal element 329 being bonded, coupled or attached to outside surface of inside tube 322. Seal element 329 could also be unitary with proximal end 338 of polymer body 316, for plugging end 337 of central tube 315. In an alternate embodiment, central tube 315 can extend to distal end of balloon 312 such that distal tip 330 also plugs and seals end 337 of central tube 315. In this alternate embodiment, polymer body could extend distally and be unitary or joined with distal tip 330. Space 327 between outside surface 351 of inside tube 322 and inside surface 352 of central tube 315 is a conduit to pressurize balloon 312. Space 327 can form a lumen. Space 327 runs between balloon 312 and connector assembly 314. Water, saline or other fluid/gas can be injected into space 327 at connector assembly 314 to pressurize balloon 312 through opening 328 in central tube 315 and polymer body 316. In an alternate embodiment, polymer body 316 is optional or terminates proximal to opening 328 in central tube 315 which allows the pressurizing media into balloon 312. Connector assembly 314 near proximal end of the adapter 108 is comprised of outer member 323 with a distal end 325 and a proximal end 324. Inside tube 322 runs coaxial to outer member 323 and along the entire length of outer member 323. Distal end 325 and proximal end 324 seal the ends of outer member 323. Inside tube 322 is shown terminating distal to the proximal edge 344 of proximal end 324. Alternately, inside tube 322 can extend to or beyond proximal edge 344 of proximal end 324. Space 327 to inject the pressurizing media into balloon 312 connects to space 345 between outside surface of inside tube 322 and inside surface of outer member 323. Opening 318 in outer member 323 allows the pressurizing media to be injected into space 345, which is connected to space 327, which is in turn connected to inside of balloon 312, allowing balloon 312 to be inflated. Space 345 can be a lumen. In one embodiment, outer member 323 of connector assembly is metallic, such as stainless steel, where distal end 325 and proximal end 324 are polymers. Alternatively, outer member 323 and ends 324 and 325 could be of unitary construction, for example made of a polymer such as PEEK. The cross-sectional view illustrates central axis 347 of adapter 108.

FIG. 26 illustrates adapter 108 after adapter 108 has been attached to target medical device 200 that has central lumen 211. For the purposes of illustration, FIG. 26 illustrates adapter 108 attached to balloon catheter 201 of medical device 200. Balloon catheter 201 is comprised of balloon 214, tubular member 218 that makes up the bulk length of balloon catheter 201, and fitting assembly 215. Fitting assembly 215 includes port 216 that connects to central lumen 211 in tubular member 218, and port 217 that connects an inflation lumen (not shown) in tubular member 218 to balloon 214. Fitting assembly 215 can be composed of a plastic or polymer with ports 217 and 216 terminated with a luer fitting for connection to a syringe or inflation device. FIG. 26 shows adapter 108 attached to balloon catheter 201 such that there is gap 321 between distal end 319 of balloon catheter 201 and proximal end 320 of balloon 312. In this illustration, polymer body 316 with channel 317 extends from balloon 312 into distal end 319 of central lumen 211 of balloon catheter 201, spanning the gap 321. Channel 317 is connected to central lumen 211, which is connected to port 216. Adapter 108 extends all the way through balloon catheter 201 such that opening 318 of connector assembly 314 is beyond proximal end 219 of balloon catheter port 216.

FIGS. 27, 28A and 28B illustrate adapter 108 attached to balloon catheter 201 as shown in FIG. 26, along with fitting 340 coupled to port 216 and fitting 331 coupled to connector assembly 314. Fitting 340 includes port 341 to couple to port 216 of fitting assembly 215 (Y-fitting) of balloon catheter 201. In one embodiment, port 341 can be a male luer fitting that is compatible with female luer fitting 216. Fitting 340 also includes sealing mechanisms 343 at proximal end 342 of fitting 340. Sealing mechanism 343 can be a Tuohy borst valve or hemostasis valve, O-ring, or other seal. Fitting 340 also includes a side port such that fluids can be introduced to the space (lumen) 346 between the outside surface of central tube 315 and lumen 211. Fitting 340 can be available valve assemblies, such as a standard Hemostasis valve with locking seal described in U.S. Pat. No. 5,591,137. Fitting 331 includes side port 333 with distal sealing mechanism 336 and proximal sealing mechanism 335 on either side of side port 333. Sealing mechanisms 335 and 336 seal on outer member 323, effectively isolating opening 318. Once opening 318 is isolated, side port 333 can be used to pressurize the balloon 312 via opening 318, space 345, space 327 and opening 328. Sealing mechanisms 335 and 336 can be O-rings, hemostasis valves, Tuohy borst valves or other seals. Fitting 331 also includes end port 332 that connects to lumen 326 of inside tube 322. As shown, fitting 331 is an assembly of two (2) seals, end port 332, side port 333, and end cap 334 to hold seal 336 in place. Fitting 331 in one embodiment can be manufactured from three (3) molded plastic components bonded, coupled or joined together holding sealing mechanism 336 and 335 in place. Adapter 108 effectively partitions lumen 211 of medical device 200, shown as balloon catheter 201 into three lumens, 346, 326, and 327. Sealing mechanism 343 of fitting 340 is shown sealing around central tube 315. Alternatively, sealing mechanism 343 can seal around outer member 323 of connector assembly 314.

FIGS. 29A, 29B, 29C, 29D, 29E and 29F illustrate an adapter 360 prior to being attached to balloon catheter 201. FIG. 29A illustrates adapter 360 which includes a plurality of slender elements 364 that extend proximally from the outer body 363 of the distal portion 361 past the proximal end 120 of proximal portion 362 of adapter 360. Slender elements 364 obscure some of the elements of adapter 360. Accordingly, for clarity, FIG. 29B shows a view wherein the slender elements 364 are omitted, and illustrates the obscured elements not shown or visible in FIG. 29A. FIG. 29B shows the proximal portion 362 which includes a right handed coil 370, similar to coil 257 previously described with reference to FIG. 18A, and a left handed coil 371 also similar to coil 257 previously described with reference to FIG. 18A. Coils 370 and 371 are bonded or attached to central tube 365. Adapter 360 includes central tube 365 that forms central lumen 366, similar to tube 190 and lumen 191 shown in FIG. 21A. Outer body 363 is typically made from a polymer or elastomeric polymer, but may be manufactured from metallic elements or include metallic elements, such as a stainless steel braid, nitinol coil or similar material. Outer body 363 includes a portion 372 with a diameter that is less than the diameter of inner lumen 211 of medical device 201 such that a portion of the outer body 179 can fit within inner lumen 211. Proximal portion 362 also includes a proximal end 120. Distal portion 361 also includes a distal tip 181. Slender elements 364 may be fibers or wires manufactured from metals such as stainless steel or Nitinol, or manufactured from a polymer such as PEEK or PVDF or other suitable material. Slender elements 364 may be a single constituent or a composite structure. As non-limiting examples, the slender elements 364 may include features or characteristics that improve scoring of the target artery or lesion, may include texture or features such as a reservoir for delivering a therapeutic agent, or may include receptors for gathering tissue, cells or other molecules for diagnostic purposes.

FIGS. 29D, 29E and 29F illustrate the cross section of adapter 360 to better illustrate the slender elements 364 and the central tube 365, with coil 370 omitted for clarity. The cross section views show an example of thirty (30) individual slender elements 364 attached to outer body 363 and that traverse past the proximal portion 362 of adapter 360. Slender elements 364 are shown in a circular pattern 368 and unconnected to each other except at the outer body 363 of the distal portion 361 and in the spiral bond portion 369. In the spiral bond portion 369, the side by side slender elements 364 may be welded, fused, bonded, glued or attached in a spiral configuration as shown, or other suitable organized configuration. As shown in cross section X-X of FIG. 29E, at any given cross section in the spiral bond portion 369, three (3) of the side by side slender elements 364 are bonded together by a bonding element 367. Bonding element 367 can be a composed of a different material than the slender element 364 or the same material as the slender element 364 as in a welded or fused junction or joint. The spiral bond portion 369 is shown progressing twice around and with a constant pitch. The spiral bond portion 369 could include a plurality of turns and a variable or constant pitch. Adapter 360 could also include a plurality of spiral bond portions 369. The cross section of the slender elements 364 are shown circular but could also be other shapes, for example a triangular shape may be advantageous when scoring a lesion or artery. Additionally, the slender elements 364 may form a circular pattern 368 as shown or a non-circular pattern, and any number of slender elements 364 may be bonded together to form a suitably stable arrangement facilitating the joining of the adapter 360 with a balloon catheter 201, as illustrated in FIGS. 30A, 30B and 30C for example.

FIGS. 30A, 30B and 30C illustrate adapter 360 attached to balloon catheter 201. As shown in FIG. 30A, the balloon 214 is not inflated, which would be the case while medical device 200 and adapter 360 would be tracked to and from the inflation site by the user. The parent module or medical device module, such as the balloon catheter 201, is a physically separate module from the adapter 360, and only the adapter 360 is physically integrated with slender elements 364 through attachment to outer body 363 of adapter 360 as described previously. When the parent module is attached to the adapter 360 of an adapter module, at least a portion of the parent module will reside inside and underneath a circumference defined by the slender elements 364, and such that slender elements 364 are presented on the outside of the assembled parent and adapter 360 module. In an example where the parent module or medical device module is a balloon catheter 201, once connected to adapter 360, the balloon 214 is placed underneath or inside a circumference defined by the slender elements 364, and while an inner lumen 211 of balloon 214 will be coupled to adapter 360 such as via coils 370, 371 or other mechanisms as described previously, the balloon's outer surface will not be physically joined or otherwise directly integrated with the slender elements 364, though the elements may or may not be in physical contact or communication with the outer surface when the balloon 214 is in a deflated state. This enables, as shown in FIGS. 30B and 30C, the slender elements 364 to flexibly and freely separate and space apart from each other equidistantly around the outer surface of balloon 214 when it is inflated, through the action of the outer surface of balloon 214 radially pushing against the slender elements 364 equally in all directions. In another example, depending on the number and positioning of the slender elements 364, one or more of the slender elements 364 may flexibly but unevenly distribute around the outer surface of balloon 214 when it is inflated. Either configuration may have utility depending on the type of tissue scoring or cutting desired.

Figure 31A:
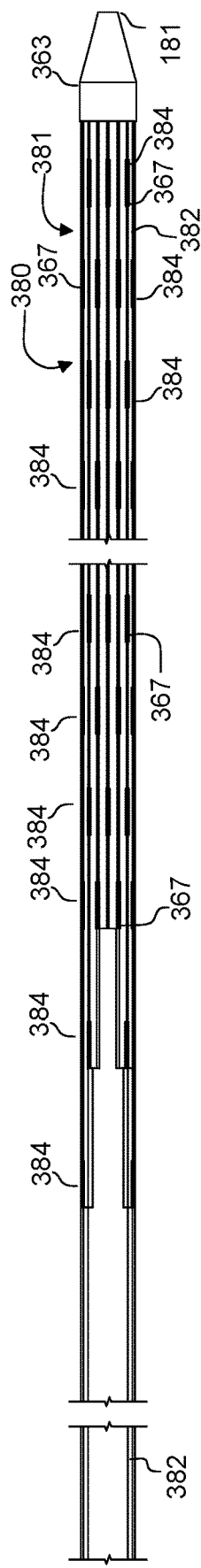
FIG. 31A is a schematic longitudinal orthographic view of an adapter according to an embodiment of the invention, where the adapter includes slender elements running longitudinal from the distal end of the adapter. This view is an orthographic projection of the longitudinal orthographic view shown in FIG. 31B. Break line symbols are utilized to reduce the size of the drawing for clarity. Some adapter elements are obscured by the slender elements.
Figure 31B:
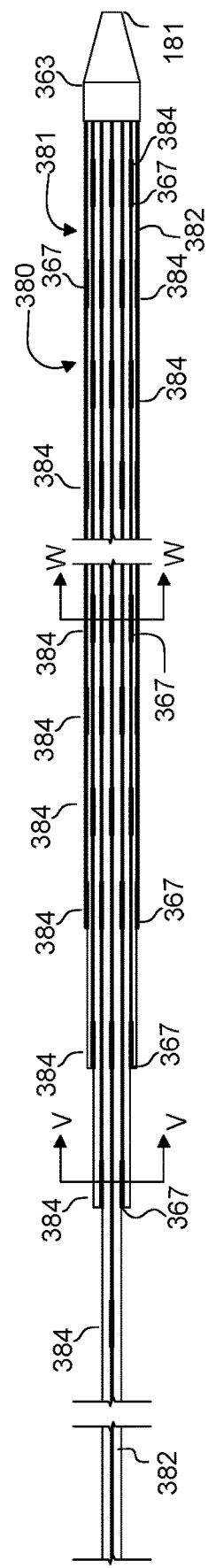
FIG. 31B is a schematic longitudinal orthographic view of an adapter according to an embodiment of the invention, where the adapter includes slender elements running longitudinal from the distal end of the adapter.

FIGS. 31A, 31B, 31C, 31D, and 31E illustrate an adapter 380 prior to being attached to balloon catheter 201. Adapter 380 is similar to adapter 360 which includes distal portion 381, similar to distal portion 361, and proximal portion 362 (obscured/not shown) which is the same proximal portion of adapter 360. As shown in FIGS. 31A and 31B, adapter 380 includes a plurality of slender elements 382 that extend proximally from the outer body 363 of the distal portion 381 past the proximal end 120 of proximal portion 362 of adapter 380. Slender elements 382 obscure some of the elements of adapter 380, and in this example comprise a rectangular cross-sectional geometry as opposed to the circular geometry of slender elements 364. For example, this rectangular cross-sectional geometry may further facilitate the cutting or scoring of target tissue. It may be appreciated that other cross-sectional geometries, including triangular, etc. are possible.

As shown in the orthographic views of FIGS. 31A, 31B and 31C and cross sections V-V and W-W of FIGS. 31D and 31E, slender elements 382 are attached to each other by a plurality of bonding elements 367. As shown in FIGS. 31D and 31E, the slender elements 382 are attached to each other by bonding elements 367 in a bond pattern 384 around the adapter 380. As shown in FIGS. 31A, 31B, and 31C, a bond pattern 384 of bonding elements 367 connecting or attaching slender elements 382 around the adapter 380 occurs at different points along the length of the adapter 380. As shown, the bond pattern 384 alternates along the length of the adapter 380 which encourages the slender elements 382 to remain approximately evenly disposed around the balloon as the balloon is inflated, i.e. not gathered on one side of the balloon, similar to as shown in FIG. 30C.

As shown in FIGS. 31A and 31B, the slender elements 382 extend proximally from the outer body 363 in lengths that create a gradual reduction in the number of slender elements 382 extending proximally. Two pairs of orthogonal slender elements 382 extend completely proximal, such that they would extend out of the patient body. As shown, a slender element 382 extension stops at a bonding element 367. This eliminates free proximal edges of the slender elements 382, which could inhibit withdrawing the target medical device catheter 201 and attached adapter 380 from the patient body. In the illustrative embodiment of FIGS. 31A, 31B, 31C, 31D, and 31E, there are shown an example of sixteen (16) slender elements 382 disposed around the central tube 365 of the adapter 380. As shown in FIG. 31E, every other slender element 382 is attached to a neighboring slender element 382 by a bonding element 367, for a total of eight (8) bond joints for a full complement of slender elements to create a bond pattern 384. The longitudinally adjacent bond pattern 384 of bonding elements 367, or bond joints, have an alternating pattern of side by side slender element 382 connections or bonds via bonding element 367 around the adapter 380. In the longitudinal position along the adapter as depicted in FIG. 31D, Section V-V, there is shown an example of eight (8) slender elements 382 attached in pairs by four (4) bonding elements 367. However, any suitable number of bonds is envisioned to optimize the functionality of adapter 380 with a balloon catheter 201 such that slender elements 382 are sufficiently stable and organized during use. In alternate embodiments, the slender elements 360, 382 could be replaced by a mesh structure or weave/braid of fibers. The described slender element 360, 382 bonding element 367 configuration could include varied bond patterns 384 organized along the length of the adapter 380.

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

For example, the nitinol coil structure could be replaced by a braided wire structure as it could readily change size by elongating to facilitate insertion into medical device 200. A braided wire structure can be manufactured from nitinol and have similar thermal-mechanical properties as the nitinol coil or can be made from a more traditional alloy, such as stainless steel and be designed to collapse to a smaller diameter as it is inserted or prior to insertion into medical device 200. A braid structure could be designed to have a similar wedge geometry when inserted into the lumen of a target catheter.

Further, instead of the user reducing the size of the nitinol coil or similar, the adapter can be manufactured and delivered to the customer pre-constrained in that shape and ready to be inserted into the target catheter or device. This would remove some of the burden from the user and possibly make it easier to use. The coil could also be a more traditional alloy without shape memory or superelastic thermal-mechanical properties such as stainless steel. The coil could be manufactured from a polymer such as PEEK or polyimide. The coil itself could be coated with a polymer.

Additionally, for configurations where the nitinol coil is coupled to the distal portion of adapter, the tube could be optional.

Although the distal portion of the adapter described herein is generally shown to be a similar size as the target catheter or device, this is not required, but may be desired. Similarly, the distal portion of the adapter can be smaller than the inner lumen of the target medical device or parent and be inserted completely within the parent device, not extending distally from the target medical device or parent at all.

If a second lumen or central lumen is not required, the elongated element that the proximal portion of coil structure is attached to could be solid as in a wire or mandrel instead of a tube. The tube, wire or mandrel could extend proximally all the way out the proximal end of the target catheter or device. Further, the outer body of the distal portion could have multiple and varied profiles. Lumens exiting outer body of the distal portion could be at varied angles instead of 180 degrees opposite each other, including on the same side of the outer body of the distal portion.

What is claimed is:

1. A modular medical device catheter system comprising: a parent module and an adapter module, the adapter module comprising a coil configured to engage an inner lumen of a distal end of the parent module to couple the adapter module with the parent module, wherein the adapter module comprises a slender element extending proximally from a distal portion of the adapter module along an outer surface of the parent module when the parent module is coupled to the adapter module.

2. The modular medical device catheter system of claim 1, wherein the adapter module further comprises an elongated element, and wherein at least a portion of the coil is attached to a portion of the elongated element at an outside surface of the elongated element.

3. The modular medical device catheter system of claim 2, wherein the elongated element connects to a distal portion of the adapter module.

4. The modular medical device catheter system of claim 3, wherein the distal portion of the adapter module extends beyond a distal end of the parent module when the adapter module and parent module are coupled together.

5. The modular medical device catheter system of claim 1, wherein the adapter module further comprises a plurality of the slender elements that are circumferentially spaced around the outer surface of the parent module when the parent module is coupled to the adapter module.

6. The modular medical device catheter system of claim 5, wherein the parent module comprises a balloon.

7. The modular medical device catheter system of claim 6, wherein the plurality of slender elements flexibly space apart from each other around the outer surface of the balloon when it is inflated.

8. The modular medical device catheter system of claim 7, wherein the plurality of slender elements flexibly space apart from each other equidistantly around the outer surface of the balloon when it is inflated.

9. The modular medical device catheter system of claim 1, wherein the slender element is only attached to the distal portion of the adapter module.

10. The modular medical device catheter of claim 5, wherein at least two of the plurality of the slender elements are bonded together at a location other than the distal portion of the adapter module.

11. The modular medical device catheter system of claim 10, further comprising multiple locations wherein at least two of the plurality of the slender elements are bonded together to thereby form an organized bonding pattern.

12. The modular medical device catheter system of claim 11, wherein the relative number of the plurality of the slender elements that are bonded together decreases proximally from the distal portion of the adapter module.

13. The modular medical device catheter system of claim 1, wherein the slender element comprises a wire or fiber.

14. A modular medical device catheter system comprising:
a parent module and an adapter module, the adapter module configured to engage an inner lumen of a distal end of the parent module to couple the adapter module with the parent module via an interference fit, and wherein the adapter module comprises a wire or fiber extending proximally from a distal portion of the adapter module along an outer surface of the parent module when the parent module is coupled to the adapter module.

15. The modular medical device catheter system of claim 14, wherein the adapter module further comprises an elongated element.

16. The module medical device catheter system of claim 15, wherein the elongated element connects to a distal portion of the adapter module.

17. The modular medical device catheter system of claim 16, wherein the distal portion of the adapter module extends beyond a distal end of the parent module when the adapter module and parent module are coupled together.

18. The modular medical device catheter system of claim 14, wherein the adapter module further comprises a plurality of the wires or fibers surrounding the outer surface of the parent module when the parent module is coupled to the adapter module.

19. A modular medical device catheter system comprising:
a parent module and an adapter module, the adapter module comprising a coil configured to engage an inner lumen of a distal end of the parent module to couple the adapter module with the parent module, wherein the adapter module comprises a slender element extending proximally from a distal portion of the adapter module, and wherein the slender element is only attached to the distal portion of the adapter module.

* * * * *